US010280230B2

(12) United States Patent
Goletz et al.

(10) Patent No.: US 10,280,230 B2
(45) Date of Patent: *May 7, 2019

(54) USE OF HUMAN CELLS OF MYELOID LEUKEMIA ORIGIN FOR EXPRESSION OF ANTIBODIES

(71) Applicant: Glycotope GmbH, Berlin (DE)

(72) Inventors: Steffen Goletz, Berlin (DE); Antje Danielczyk, Berlin (DE); Hans Baumeister, Berlin (DE); Renate Stahn, Berlin (DE); Anja Loeffler, Eichhorst (DE); Lars Stoeckl, Berlin (DE)

(73) Assignee: Glycotope GmbH, Berlin (DE)

( * ) Notice: Subject to any disclaimer, the term of this patent is extended or adjusted under 35 U.S.C. 154(b) by 278 days.

This patent is subject to a terminal disclaimer.

(21) Appl. No.: 14/703,498

(22) Filed: May 4, 2015

(65) Prior Publication Data

US 2015/0368363 A1 Dec. 24, 2015

Related U.S. Application Data

(63) Continuation of application No. 12/440,562, filed as application No. PCT/EP2007/007877 on Sep. 10, 2007, now Pat. No. 9,051,356.

(30) Foreign Application Priority Data

| Sep. 10, 2006 | (EP) | 06090162 |
| Sep. 18, 2006 | (EP) | 06090171 |
| Oct. 13, 2006 | (EP) | 06090190 |
| May 4, 2007 | (EP) | 07090094 |

(51) Int. Cl.
| C07K 14/59 | (2006.01) |
| C07K 16/00 | (2006.01) |
| C07K 16/28 | (2006.01) |
| C07K 16/30 | (2006.01) |
| C07K 16/46 | (2006.01) |

(52) U.S. Cl.
CPC ............ *C07K 16/461* (2013.01); *C07K 14/59* (2013.01); *C07K 16/00* (2013.01); *C07K 16/2863* (2013.01); *C07K 16/3092* (2013.01); *C07K 2317/24* (2013.01); *C07K 2317/41* (2013.01); *C07K 2317/72* (2013.01); *C07K 2317/732* (2013.01); *C07K 2317/734* (2013.01)

(58) Field of Classification Search
None
See application file for complete search history.

(56) References Cited

U.S. PATENT DOCUMENTS

| 4,931,275 | A | 6/1990 | Shinitzky et al. |
| 5,506,343 | A | 4/1996 | Kufe |
| 5,547,933 | A | 8/1996 | Lin |
| 5,596,088 | A * | 1/1997 | Boucher ............ C07K 14/705 435/252.3 |
| 5,683,674 | A | 11/1997 | Taylor-Papadimitriou et al. |
| 5,739,277 | A | 4/1998 | Presta et al. |
| 5,795,779 | A | 8/1998 | McCormick et al. |
| 5,804,187 | A | 9/1998 | do Couto et al. |
| 5,888,773 | A * | 3/1999 | Jost ................. C07K 16/44 424/133.1 |
| 5,948,646 | A | 9/1999 | Srivastava |
| 5,961,979 | A | 10/1999 | Srivastava |
| 6,168,793 | B1 | 1/2001 | Srivastava |
| 6,315,997 | B1 | 11/2001 | do Couto et al. |
| 6,602,684 | B1 | 8/2003 | Umana et al. |
| 6,946,292 | B2 | 9/2005 | Kanda et al. |
| 6,984,384 | B1 | 1/2006 | Subjeck et al. |
| 7,268,120 | B1 | 9/2007 | Horton et al. |
| 7,595,192 | B2 | 9/2009 | Goletz et al. |
| 8,017,388 | B2 | 9/2011 | Goletz et al. |
| 8,088,357 | B2 | 1/2012 | Goletz et al. |
| 8,283,161 | B2 | 10/2012 | Goletz et al. |
| 8,592,165 | B2 | 11/2013 | Goletz et al. |
| 8,609,370 | B2 | 12/2013 | Goletz et al. |
| 8,617,846 | B2 | 12/2013 | Goletz et al. |
| 8,741,365 | B2 | 6/2014 | Goletz et al. |
| 9,051,356 | B2 | 6/2015 | Goletz et al. |
| 9,345,794 | B2 | 5/2016 | Goletz et al. |
| 9,494,587 | B2 | 11/2016 | Goletz et al. |

(Continued)

FOREIGN PATENT DOCUMENTS

| DE | 4329004 A1 | 3/1995 |
| EP | 0117060 A2 | 8/1984 |

(Continued)

OTHER PUBLICATIONS

Adams et al (Journal of Nuclear Medicine, 1995, vol. 36, pp. 2276-2281).*
Raju et al, Glycobiology, 2000, vol. 10, pp. 477-486.*
Savvidou et al, Biochemistry, 1984, vol. 23, pp. 3736-3740.*
Kinoshita et al, Cancer Research, 1991, vol. 51, pp. 5888-5892.*
Dictionary of Immunology, pp. 3, 7, 46, 87-88, 94, 97, 105,116.
Dorai, H., et al., "The Effect of Dihydrofolate Reductase-Mediated Gene Amplification on the Expression of Transfected Immunoglobulin Genes," Journal of Immunology (Baltimore, Md. 1950), Dec. 15, 1987, vol. 139, No. 12, pp. 4232-4241.
Dressel, "Heat Shock Protein 70 Is Able to Prevent Heat Shock-Induced Resistance of Target Cells to CTL," J. Immunol., 164:2362-2371 (2000).

(Continued)

*Primary Examiner* — Karen A. Canella
(74) *Attorney, Agent, or Firm* — Nelson Mullins Riley & Scarborough LLP; Jane E. Remillard, Esq.; Jill Gorny Sloper, Esq.

(57) ABSTRACT

The invention relates to a method for producing a protein molecule composition having a defined glycosylation pattern, comprising (a) introducing in a host cell which is an immortalized human blood cell at least one nucleic acid encoding at least a part of said protein; and (b) culturing said host cell under conditions which permit the production of said protein molecule composition; and (c) isolating said protein molecule composition.

37 Claims, 19 Drawing Sheets

Specification includes a Sequence Listing.

(56) References Cited

U.S. PATENT DOCUMENTS

| | | |
|---|---|---|
| 2002/0132771 A1 | 9/2002 | Madiyalakan |
| 2003/0115614 A1 | 6/2003 | Kanda et al. |
| 2004/0029127 A1 | 2/2004 | Postaire et al. |
| 2004/0265998 A1 | 12/2004 | Goletz et al. |
| 2005/0187378 A1 | 8/2005 | Kim |
| 2005/0203010 A1 | 9/2005 | Kim |
| 2006/0127419 A1 | 6/2006 | Goletz et al. |
| 2006/0251668 A1 | 11/2006 | Goletz et al. |
| 2006/0292129 A1 | 12/2006 | Goletz et al. |
| 2006/0292643 A1 | 12/2006 | Goletz et al. |
| 2007/0015239 A1 | 1/2007 | Bihoreau et al. |
| 2007/0116704 A1 | 5/2007 | Goletz et al. |
| 2008/0226681 A1 | 9/2008 | Goletz et al. |
| 2009/0046556 A1 | 2/2009 | Vlutters |
| 2010/0028947 A1 | 2/2010 | Goletz et al. |
| 2010/0158952 A1 | 6/2010 | Goletz |
| 2010/0303837 A1 | 12/2010 | Goletz et al. |
| 2011/0129570 A1 | 6/2011 | Goletz |
| 2011/0319590 A1 | 12/2011 | Goletz et al. |
| 2012/0128676 A1 | 5/2012 | Goletz et al. |
| 2012/0128678 A1 | 5/2012 | Aburatani et al. |
| 2012/0149877 A1 | 6/2012 | Goletz et al. |
| 2014/0099259 A1 | 4/2014 | Goletz et al. |

FOREIGN PATENT DOCUMENTS

| | | |
|---|---|---|
| EP | 1167537 A1 | 1/2002 |
| EP | 1176195 A1 | 1/2002 |
| EP | 1371735 A1 | 12/2003 |
| EP | 1900750 A1 | 3/2008 |
| EP | 1911766 A1 | 4/2008 |
| EP | 1920781 A1 | 5/2008 |
| WO | 9215682 A1 | 9/1992 |
| WO | 93/20841 A1 | 10/1993 |
| WO | 9429469 A2 | 12/1994 |
| WO | 9700957 A1 | 1/1997 |
| WO | 97/30087 A1 | 8/1997 |
| WO | 9740182 A1 | 10/1997 |
| WO | 9929834 A1 | 6/1999 |
| WO | 0041576 A1 | 7/2000 |
| WO | 0052135 A2 | 9/2000 |
| WO | 00/61739 A1 | 10/2000 |
| WO | 01/12217 A1 | 2/2001 |
| WO | 0230954 A1 | 4/2002 |
| WO | 02/44217 A2 | 6/2002 |
| WO | 03016329 A2 | 2/2003 |
| WO | 03/023023 A1 | 3/2003 |
| WO | 03/035686 A2 | 5/2003 |
| WO | 03035636 A2 | 5/2003 |
| WO | 03044051 A1 | 5/2003 |
| WO | 2004009632 A2 | 1/2004 |
| WO | 2004018659 A1 | 3/2004 |
| WO | 2004/050707 A2 | 6/2004 |
| WO | 2004065423 A2 | 8/2004 |
| WO | 2005016962 A2 | 2/2005 |
| WO | 2005017130 A2 | 2/2005 |
| WO | 2005040221 A1 | 5/2005 |
| WO | 2005080585 A1 | 9/2005 |
| WO | 2005108423 A1 | 11/2005 |
| WO | 2006012616 A2 | 2/2006 |
| WO | 2007124992 A1 | 11/2007 |
| WO | 2008/028686 A2 | 3/2008 |
| WO | 2008/055703 A2 | 5/2008 |
| WO | 2008055702 A1 | 5/2008 |
| WO | 2011012309 A1 | 2/2011 |
| WO | 2014111509 A2 | 7/2014 |
| WO | 2015/111509 A1 | 7/2015 |

OTHER PUBLICATIONS

Duk et al., "Purification of Human Anti-TF (Thomsen-Friedenrelch) and Antl-Tn Antibodies by Affinity Chromatography on Glycophorin a Derivatives and Characterization of the Antibodies by Microtiter Plate ELISA", Archivum Immunologiae et TherapiaeExperimentalis, vol. 46, No. 2, pp. 69-77, XP-008045186, (1998).

Elbashir, et al. "Duplexes of 21-nucleotide RNAs mediate RNA interference in cultured mammalian cells". Nature, vol. 411, 2001, pp. 494-498.

Euhus, D. et al., "Appraisal of Anti-Idiotypic Antibodies in the Treatment of Solid Tumors in Humans," Surgery, Gynecology & Obstetrics, vol. 175, pp. 89-96 (1992).

European Office Action dated Jul. 20, 2011 for European Patent Application No. 09 745 554.7-1221.

European Patent Office communication for European Patent Application No. 07 818 090.8-2406 dated Nov. 23, 2012 (5 pgs).

European Search Report for Application No. 11 17 6193.8, dated Apr. 16, 2012.

European Search Report for Application No. 11 17 6197.9, dated Apr. 12, 2012.

European Search Report for Application No. 11 17 6200.1, dated Apr. 12, 2012.

Feng, "Stressed apoptotic tumor cells express heat shock proteins and elicit tumor-specific immunity," Blood, 97:3505-3512 (2001).

Ferencik, M. Handbook of Immunochemistry, p. 115-116. Chapman & Hall (1993).

Fiebig, H. et al., "Clonogenic Assay with Established Human Tumour Xenografts: Correlation of In Vitro to In Vivo Activity as a Basis for Anticancer Drug Discovery," European Journal of Cancer, vol. 40, Issue 6, pp. 802-820 (2004).

Fogolin et al. "Choice of the adequate quantification method for recombinant human GM-CSF produced in different host systems," Electronic J. of Biotech. 5: 243-250 (2002).

Franco, A., "CTL-Based Cancer Preventive/Therapeutic Vaccines for Carcinomas: Role of Tumour-Associated Carbohydrate Antigens," Scandinavian Journal of Immunology, vol. 61, No. 5, pp. 391-397 (2005).

Freshney, R., Culture of Animal Cells: A Manual of Basic Technique and Specialized Applications, Alan R. Liss Inc., New York, p. 4 (1983).

Fujiwara, "Establishment of a tumor-specific immunotherapy model utilizing TNP-reactive helper T cell activity and its application to the autochthonous tumor system," J. Immunol. 133:509-514 (1984).

Fukuda, M. et al. "Structures of novel sialyated O-linked oligosaccharides isolated from human erythrocyte glycophorins," The Journal of Biological Chemistry, 262(25): 11952-11957 (1987).

Galluci, "Danger signals: SOS to the immune system," Curr. Opin. Immunol. 13:114-119 (2001).

Galluci, "Natural adjuvants: Endogenous activators of dendritic cells," Nat. Med. 11:1249-1255 (1991).

Geneseq, "DHFR-Synuclein Fusion Protein GST-ATSalpha Seq. ID No. 81," (2005) XP002430726.

Giovanella, "Effects of Elevated Temperatures and Drugs on the Viability of L1210 Leukemia Cells," Cancer Res., 30:1623-1631 (1970).

Goletz et at, "Bacterial-Derived Thomsen-Friedenreich Antigen Activates Specific T Cells via Presentation on Dendritic Cells," Glycobiology, Nov. 2011, 21/11:1525 abstract Only.

Goletz, "Commensal Bacteria Expressing the Carbohydrate Human Tumour-Specific Antigen Gal.beta.1-3GalNAc. alpha.—(Thomsen-Friedenreich) as a Potential Tumour Vaccine," Glycobiology, Nov. 2011, 21/11:1524 abstract only.

Goletz, S. et al., "Binding Patterns of 33 TD-4 (MUC1) Antibodies Towards Single-Chain Fragments and Peptides Mimicking the Conformation of the MUC1 PDTRP Epitope," Tumor Biology, vol. 21, Suppl. 1, p. 142 (2000).

Goletz, S., "Turning Glycomics into Health," (2006) XP00243302.

Goletz, S., et al., "Thomsen-Friedenreich Antigen: The Hidden Tumor Antigen," Advances in Experimental Medicine and Biology, vol. 535, pp. 147-162 (2003).

Gollasch et al., "Identification of Immunogenic Peptide-Mimics for the Thomsen-Friedenreich-Glycoantigen"; Annals of Hematology, Berlin, DE, vol. 77, No. suppl. 2. p. S84, XP-000960533, (1998).

Gough, M.J. et al., "Macrophages Orchestrate the Immune Response to Tumor Cell Death," Cancer Research 61, pp. 7240-7247 (2001).

(56) References Cited

OTHER PUBLICATIONS

Green, D. et al., "Activation-Induced Cell Death in T Cells," Immunological Reviews, vol. 193, Issue 1, pp. 70-81 (2003).
Gura, T., "Systems for Identifying New Drugs are Often Faulty," Science, vol. 278, pp. 1041-1042 (1997).
Henderson et al., "Occurrence of the humor tumor-specific antigen structure GaLbeta.1-3GalNAc.alpha.—(Thomsen-Friedenreich) and related structures on gut bacteria: Prevalence, immunochemical analysis and structural confirmation." vol. 21, No. 10.pp. 1277-1289 (2011).
Herrera, A. et al., "Efficiency of Erythropoietin's Signal Peptide for HIV.sub.MN-1 gp 120 Expression," Biochemical and Biophysical Research Communications, vol. 273, Issue 2, pp. 557-559 (2000).
Hinoda, Y. et al., "Circulating Tumor-Associated Antigens Detected by Monoclonal Antibodies Against the Polypeptide Core of Mucin-Comparison of Antigen MUSE11 with CA15-3," Gastroenterologia Japonica, vol. 27, No. 3, pp. 390-395 (1992).
Hinoda, Y. et al., "Primary Structure of the Variable Regions of a Monoclonal Antibody MUSE11 Recognizing the Tandem Repeat Domain of a Mucin Core Protein, MUC1," Journal of Clinical Laboratory Analysis, vol. 7, pp. 100-104 (1993).
Holm, P. et al., "Functional Mapping and Single Chain Construction of the Anti-Cytokeratin 8 Monoclonal Antibody TS1," Molecular Immunology, vol. 44, Issue 6, pp. 1075-1084 (2007).
Hong, Y. et al. "Lec3 Chinese Hamster Ovary Mutants Lack UPD-N-acetylglucosamine 2-EPimerase Activity Because of Mutations in the Epimerase Domain of the Gne Gene," J. Biol. chem 278(52): 53045-53054 (2003).
Hosse, R. et al., "A New Generation of Protein Display Scaffolds for Molecular Recognition," Protein Science, vol. 15, Issue 1, pp. 14-27 (2006).
Hseih, L. et al., "Controlling Chemical Reactivity with Antibodies," Science, vol. 260, pp. 337-339 (1993).
Huang et al., Cancer Research 60:3435-3439 (2000).
Hufton, S. et al., "Development and Application of Cytotoxic T Lymphocyte-Associated Antigen 4 as a Protein Scaffold for the Generation of Novel Binding Ligands," FEBS Letters, vol. 475, Issue 3, pp. 225-231 (2000).
Ichiyama, "Induction of Non-HLA Restricted Anti-Tumor Effector Cells with Strong Cytoxic Activity Using MUC1/B7 Cotransfected K562 Cells," Cell Resource Center for Biomedical Research, Institute of Development, Aging, and Cancer, Tohoku University,Sendai, Japan, vol. 51, No. 3-4, pp. 93-110, XP-001182213 (2000).
International Search Report for PCT Application No. PCT/EP2005/01593 (WO 2005/080585) dated Jul. 15, 2005.
International Search Report for PCT Application No. PCT/EP2007/007877 (WO 2008/028686 A3) dated Apr. 18, 2008.
International Search Report for PCT Application No. PCT/EP2007/009765 (WO 2008/055702 A1) dated Apr. 15, 2008.
International Search Report for PCT Application No. PCT/EP2007/009766 (WO 2008/055703 A2) dated Oct. 7, 2008.
International Search Report for PCT/DE2003/003994 (WO2004/050707) dated Aug. 10, 2004.
International Search Report for PCT/EP03/09140, (WO/2004/018659) dated Feb. 9, 2004.
International Search Report for PCT/EP2004/009281, (WO/2005/017130) dated Apr. 15, 2005.
Todryk, "Heat shock protein 70 induced during tumor cell killing induces Th1 cytokines and targets immature dendritic cell precursors to enhance antigen uptake," The Journal of Immunology, 163:1398-1408 (1999).
Vajdos, F. et al., "Comprehensive Functional Maps of the Antigen-Binding Site of an Anti-ErbB2 Antibody Obtained with Shotgun Scanning Mutagenesis," Journal of Molecular Biology, vol. 320, Issue 2, pp. 415-428 (2002).
Van Rinsum, et al., "Specific inhibition of human natural killer cell-mediated cytotoxicity by sialic acid and sialo-oligosaccharides." Int. J. Cancer, 38:915-922 (1986).
Verma, et al. "Gene therapy—promises, problems and prospects". Nature, vol. 389, 1997, pp. 239-242.
Vermes, "A novel assay for apoptosis. Flow cytometric detection of phosphatidylserine expression on early apoptotic cells using fluorescein labelled Annexin V," J. Immunol. Meth., 184:39-51 (1995).
Viswanatha, K. et al. "Engineering sialic acid synthetic ability into insect cells: identifying metabolic bottlenecks and devising strategies to overcome them," Biochemistry 42(51): 15215-15225 (2003).
Voshol, H. et al., "Cell Surface Glycoconjugates as Possible Targets for Human Natural Killer Cells: Evidence Against the Involvement of Glycolipids an N-Linked Carbohydrate Chains," Gylcobiology, vol. 3, No. 1, pp. 69-76 (1993).
Wacker et al (European Journal of Pharmaceutics and Biopharmaceutics, 2011, vol. 79, pp. 503-507).
Wang, Q. et al., "Second-Generation Adenovirus Vectors," Nature Medicine, vol. 2, No. 6, pp. 714-716 (1996).
Weikert et al., "Engineering Chinese hamster ovary cells to maximize sialic acid content of recombinant glycoproteins," Nature Biotechnology, vol. 17, pp. 1116-1121 (Nov. 1999).
Wells, "Heat shock proteins, tumor immunogenicity and antigen presentation: an integrated view," Immunol. Today, 21:129-132 (2000).
Werkmeister, J. et al., "Modulation of K562 Cells with Sodium Butyrate. Association of Impaired NK Susceptibility with Sialic Acid and Analysis of Other Parameters," International Journal of Cancer, vol. 32, pp. 71-78 (1983).
Wu, H. et al., "Humanization of a Murine Monoclonal Antibody by Simultaneous Optimization of Framework and CDR Residues," Journal of Molecular Biology, vol. 294, Issue 1, pp. 151-162 (1999).
Wu, S. et al., "Conformation of Complementarity Determining Region L1 Loop in Murine IgG .lamda. Light Chain Extends the Repertoire of Canonical Forms," Journal of Molecular Biology, vol. 229, Issue 3, pp. 597-601 (1993).
Yoshima et al., J Biol Chem 273(39):25466-25471 (1998).
Yu, J-Y. et al., "RNA Interference by Expression of Short-Interfering RNAs and Hairpin RNAs in Mammalian Cells," Proceedings of the National Academy of Sciences, vol. 99, No. 9, pp. 6047-6052 (2002).
Zhang et al (Biochimica et Biophysica Acta, 1998, vol. 1425, pp. 441-452).
Zhang, S. et al., "Selection of Tumor Antigens as Targets for Immune Attack Using Immunohistochemistry: II. Blood Group-Related Antigens," International Journal of Cancer, vol. 73, pp. 50-56 (1997).
Irazoqui et al., "Thomsen-Friedenreich Disaccharide Immunogenicity," Current Cancer Drug Targets, 2003, 3:433-443.
Isner, et al. "Clinical evidence of angiogenesis after arterial gene transfer of phVEGFI 65 in patient with ischaemic limb". The Lancet, vol. 348, 1996, pp. 370-374.
Jacobs, C. L.,et al., "Substrate specificity of the sialic acid biosynthetic pathway," Biochemistry, 40:12864-12874 (2001).
Jager, G. et al., "Treatment of Extranodal Marginal Zone B-Cell Lymphoma of Mucosa-Associated Lymphoid Tissue TYpe with Cladribine: A Phase II Study," Journal of Clinical Oncology, vol. 20, Issue 18, pp. 3872-3877 (2002).
Jensen, K. et al., "Functional Improvement of Antibody Fragments Using a Novel Phage Coat Protein III Fusion System," Biochemical and Biophysical Research Communications, vol. 298, Issue 4, pp. 566-573 (2002).
Jeschke, U. et al., "Expression of the Thomsen-Friedenreich Antigen and of its Putative Carrier Protein Mucin 1 in the Human Placenta and in Trophoblast Cells In Vitro," Histochemistry and Cell Biology, vol. 117, No. 3, pp. 219-226 (2002).
Jones, M. et al. "Characterization of the cellular uptake and metabolic conversion of acetylated N-acetylmannosamine (ManNAc) analogues to sialic acids," Biotechnology and Bioengineering, 85 (4): 394-405 (2004).
Kalka-Moll, W. et al., "Zwitterionic Polysaccharides Stimluate T Cells by MHC Class II-Dependent Interactions," The Journal of Immunology, vol. 169, pp. 6149-6153 (2002).
Kanda Yutaka, et al., "Comparison of Cell Lines for Stable Production of Fucose-Negative Antibodies with Enhanced ADCC," Biotechnology and Bioengineering, Jul. 2006, vol. 94, No. 4, pp. 680-688.

(56) References Cited

OTHER PUBLICATIONS

Kaneko, Y., et al., "Anti-Inflammatory Activity of Immunogloubulin G Resulting from FC Sialylation," Science, American Association for the Advancement of Science, Aug. 2006, vol. 313, No. 5787, p. 671.
Karsten et al., "Enhanced Binding of Antibodies to the DTR Motif of MUC1 Tandem Repeat Peptide is Mediated by Site-Specific Glycosylation", Cancer Research, American Association for Cancer Research, Baltimore, MD, US, vol. 58, No. 12, pp. 2541-2549,XP-002112486, (Jun. 15, 1998).
Karsten, U. et al., "A New Monoclonal Antibody (A78-G/A7) to the Thomsen-Friedenreich Pan-Tumor Antigen," Hybridoma, vol. 14, No. 1, pp. 37-44 (1995).
Keppler, O. et al. "UDP-GlcNac 2-Epimerase: A Regulator of Cell Surface," Science 284: 1372-1376 (1999).
Klaamas, K., et al., "Expression of Tumor-Associated Thomsen-Friedenreich Antigen (T AG) in Helicobacter Pylori and Modulation of T AG Specific Immune Response in Infected Individuals," Immunological Investigations, vol. 31, No. 3/4, pp. 191-204(2002).
Kotera, Y. et al., "Comparative Analysis of Necrotic and Apoptotic Tumor Cells as a Source of Antigen(s) in Dendritic Cell-Based Immunization," Cancer Research, vol. 61, No. 22, pp. 8105-8109 (2001).
Kozak, R. et al., "Nature of the Bifunctional Chelating Agent Used for Radioimmunotherapy with Yttrium-90 Monoclonal Antibodies: Critical Factors in Determining In Vivo Survival and Organ Toxicity," Cancer Research, vol. 49, pp. 2639-2644 (1989).
Kunz, "Synthetic Glycopeptides for the Development of Tumour-selective Vaccines", Journal of Peptide Science: an Official Publication of the European Peptide Society, vol. 9, No. 9, pp. 563-573, XP-00845163, (Sep. 2003).
Kurtenkov, O., et al., "Better Survival of Helicobacter Pylori Infected Patients With Early Gastric Cancer Is Related to a Higher Level of Thomsen-Friedenreich Antigen-Specific Antibodies," Immunological Investigations, vol. 32, No. 1-2, pp. 89-93(2003).
Lazar, E. et al., "Transforming Growth Factor Alpha: Mutation of Aspartic Acid 47 and Leucine 48 Results in Different Biological Activities," Molecular and Cellular Biology, vol. 8, pp. 1247-1252 (1988).
Leffell, Mary S., "An Overview of the Immune System: The Molecular Basis for Immune Responses", Human Immunology Handbook, 1:1-45 (1997).
Liao, K-W.et al., "Design of Transgenes for Efficient expression of Active Chimeric Proteins on Mammalian Cells," Biotechnology and Bioengineering, vol. 73, Issue 4, pp. 313-323 (2001).
Libyh, M. et al., "A Recombinant Human scFv Anti-Rh(D) Antibody with Multiple Valences Using a C-Terminal Fragment of C4-Binding Protein," Blood, vol. 90, No. 10, pp. 3978-3983 (1997).
Linardou, Abstract, "Deoxyribonuclease I (DNAse I). A Novel Approach for Targeted Cancer Therapy," Cell Biophys., vol. 24-25, 243-248 (1994).
Lozzio and Lozzio, Blood 45(3):321-334 (1975).
Luftig, R.B., Microbiology and Immunology, pp. 228-229, Lippincott-Raven Pub, Phila. (1998).
MacCallum, R. et al., "Antibody-Antigen Interactions: Contact Analysis and Binding Site Topography," Journal of Molecular Biology, vol. 262, Issue 5, pp. 732-745 (1996).
Mach, "Cytokine-secreting tumor cell vaccines," Curr. Opin. Immunol. 12, 571-575 (2000).
MacLean, G.D., et al., "Active Immunization of Human Ovarian Cancer Patients Against a Common Carcinoma (Thomsen-Friedenreich) Determinant Using a Synthetic Carbohydrate Antigen," Journal of Immunotherapy, vol. 11, pp. 292-305 (1992).
Mantey, L. R., et al., "Efficient biochemical engineering of cellular sialic acids using an unphysiological sialic acid precursor in cells lacking UPD-N-acetylglucosamine 2-epimerase," FEBS Letters, 503:80-84 (2001).
Marshall, "Gut-Derived Organisms for Milk Fermentations," Centre for Sciences of Food and Nutrition, Oxford Polytechnic, Headington. Oxford OX30BP, UK, pp. 548-553, (1991).

Martin, A. et al.,"Structural Families in Loops of Homologous Proteins: Automatic Classification, Modelling and Application to Antibodies," Journal of Molecular Biology, vol. 263, Issue 5, pp. 800-815 (1996).
Matsumoto-Takasaki et al., "Isolation and characterization of anti-T-antigen single chain antibodies from a phage library," BioScience Trends 2009; 3(3):87-95.
Matsuzaki, T., et al., "Antitumor Effect of Intrapleural Administration of Lactobacillus casei in Mice," Cancer Immunology Immunotherapy, vol. 26, No. 3, pp. 209-214 (1988).
Matzinger, P., "Tolerance, Danger, and the Extended Family," Annual Review in Immunology, vol. 12, pp. 991-1045 (1994).
Mazmanian, S. et al., "The Love-Hate Relationship Between Bacterial Polysaccharides and the Host Immune System," Nature Reviews, vol. 6, pp. 849-858 (2006).
Melcher, "Apoptosis or necrosis for tumor immunotherapy: what's in a name?" J. Mol. Med, 77:824-833 (1999).
Melcher, "Tumor immunogenicity is determined by the mechanism of cell death via induction of heat shock protein expression," Nat Med. 4:581-587 (1998).
Mise, "Effect of Heat Treatment on Tumor Cells and Antitumor Effector Cells," Cancer Res., 50:6199-6202(1990).
Mitchell, M. et al., "Active Specific Immunotherapy for Melanoma: Phase I Trial of Allogeneic Lysates and a Novel Adjuvant," Cancer Research, vol. 48, pp. 5883-5893 (1988).
Mivechi, Cancer Research 49:1954-1958 (1989).
Mondovi, "Increased immunogenicity of Ehrlich ascites cells after heat treatment," Cancer, (30)4:885-888 (1972).
Morrison, S. et al., "Complement Activation and Fc Receptor Binding by IgG," Protein Engineering of Antibody Molecules for Prophylactic and Therapeutic Applications in Man, Clark, M., Ed., pp. 101-113 (1993).
MSNBC News Services, "Mixed Results on New Cancer Drug," Nov. 9, 2000.
Muramatsu et al., "Glycoprotein-Bound Large Carbohydrates of Early Embryonic Cells: Structural Characteristic of the Glycan Isolated from F9 Carcinoma Cells," J. Biochem. 94:799-810 (1983).
Natali, et al., Heterogeneity in the expression of HLA and tumor-associated antigens by surgically removed and cultured breast carcinoma cells. Cancer Res 1983; 43:660-668.
Nicaise, M. et al., "Affinity Transfer by CDR Grafting on a Nonimmunoglobulin Scaffold," Protein Science, vol. 13, Issue 7, pp. 1882-1891 (2004).
Novina, et al. "siRNA-directed inhibition of HIV-1 infection". Nature Medicine, vol. 8, No. 7,2002, pp. 681-686.
Nuttall, S. et al., "Design and Expression of Soluble CTLA-4 Variable Domain as a Scaffold for the Display of Functional Polypeptides," Proteins: Structure, Function, and Genetics, vol. 36, Issue 2, pp. 217-227 (1999).
Nygren, P-A. et al., "Scaffolds for Engineering Novel Binding Sites in Proteins," Current Opinion in Structural Biology, vol. 7, Issue 4, pp. 463-469 (1997).
Ohyama, et al. "Dual roles of sialyl Lewis X oligosaccharides in tumor metastasis and rejection by natural killer cells". The EMBO Journal, vol. 18, No. 6, 1999, pp. 1516-1525.
U.S. Appl. No. 10/524,738, filed Sep. 15, 2005, Steffen Goletz.
U.S. Appl. No. 10/536,834, filed Mar. 20, 2006, Steffen Goletz.
U.S. Appl. No. 10/568,098, filed Jun. 20, 2006, Steffen Goletz.
U.S. Appl. No. 10/589,447, filed Feb. 7, 2008, Steffen Goletz.
U.S. Appl. No. 12/514,200, filed Nov. 11, 2009, Steffen Goletz.
U.S. Appl. No. 12/514,248, filed Nov. 25, 2009, Steffen Goletz.
U.S. Appl. No. 12/991,827, filed Jan. 28, 2011, Steffen Goletz.
U.S. Appl. No. 12/440,562, filed May 14, 2009, Steffen Goletz.
U.S. Appl. No. 10/524,738, May 19, 2009.
U.S. Appl. No. 10/524,738, Aug. 4, 2008.
U.S. Appl. No. 10/524,738, Feb. 6, 2008.
U.S. Appl. No. 10/524,738, Aug. 10, 2007.
U.S. Appl. No. 10/524,738, Sep. 15, 2005.
U.S. Appl. No. 10/536,834, Aug. 25, 2011.
U.S. Appl. No. 10/536,834, Feb. 20, 2011.
U.S. Appl. No. 10/536,834, Aug. 5, 2010.
U.S. Appl. No. 10/536,834, Nov. 10, 2009.
U.S. Appl. No. 10/536,834, Feb. 19, 2009.

(56) References Cited

OTHER PUBLICATIONS

U.S. Appl. No. 10/536,834, Jun. 23, 2008.
U.S. Appl. No. 10/568,098, May 12, 2011.
U.S. Appl. No. 10/568,098, Sep. 29, 2010.
U.S. Appl. No. 10/568,098, Jul. 23, 2009.
U.S. Appl. No. 10/568,098, Jan. 27, 2009.
U.S. Appl. No. 10/568,098, May 9, 2008.
U.S. Appl. No. 10/589,447, Aug. 7, 2013.
U.S. Appl. No. 10/589,447, Feb. 25, 2013.
U.S. Appl. No. 10/589,447, Apr. 9, 2012.
U.S. Appl. No. 10/589,447, Aug. 26, 2011.
U.S. Appl. No. 10/589,447, Feb. 3, 2011.
U.S. Appl. No. 12/514,200, Jun. 21, 2013.
U.S. Appl. No. 12/514,200, Feb. 22, 2013.
U.S. Appl. No. 12/514,200, Sep. 18, 2012.
U.S. Appl. No. 12/514,200, Nov. 30, 2011.
U.S. Appl. No. 12/514,248, Dec. 26, 2014.
U.S. Appl. No. 12/514,248, Jun. 27, 2013.
U.S. Appl. No. 12/514,248, Apr. 11, 2013.
U.S. Appl. No. 12/514,248, Sep. 21, 2012.
U.S. Appl. No. 12/991,827, Jan. 30, 2014.
U.S. Appl. No. 12/991,827, Nov. 19, 2013.
U.S. Appl. No. 12/991,827, Mar. 18, 2013.
U.S. Appl. No. 12/440,562, Feb. 6, 2015.
U.S. Appl. No. 12/440,562, Jul. 15, 2014.
U.S. Appl. No. 12/440,562, Oct. 13, 2011.
U.S. Appl. No. 12/440,562, Oct. 28, 2010.
U.S. Appl. No. 12/514,248, Steffen Goletz, filed Nov. 25, 2009, Oct. 1, 2015.
Boyd, P.N. et al., "The effect of the removal of sialic acid, galactose and total carbohydrate on the functional activity of Campath-1H," Molecular Immunology, vol. 23(17/18) pp. 1311-1318 (1995).
Cant, D. et al., "Glycosylation and functional activity of anti-D secreted by two human lymphoblastoid cell lines," Cytotechnology, vol. 15(1-3), pp. 223-228. (1994).
Danielczyk, A. et al., "PankoMab: a potent new generation anti-tumour MUC1 antibody," Cancer Immunol Immunother, vol. 55, pp. 1337-1347 (2006).
Delwel, G. et al., "Expression and function of the cytoplasmic variants of the integrin alpha 6 subunit in transfected K562 cells. Activation-dependent adhesion and interaction with isoforms of laminin," The Journal of Biological Chemistry, vol. 268 (34), pp. 25865-25875 (1993).
European Patent EP2073842B1, "Data obtained by the opponent on the lines NM-H9D8-E6 and NM-H9D8-E6Q12," filed Feb. 16, 2015, pp. 1-22 (2015).
Hajirezaei, M. et al., "Cloning and expression of the functional human anti-vascular endothelial growth factor (VEGF) using the pcDNA3.1 vector and the human chronic myelogenous leukemia cell line K562," Protein J., vol. 33(1), pp. 100-109 (2014).
Jefferis, R. et al., Glycosylation of Recombinant Antibody Therapeutics, Biotechnology Prog., vol. 21(1), pp. 11-16 (2005).
Lifely, M.R., et al., "Glycosylation and Biological Activity of CAMPATH-1H expressed in Different Cell Lines and Grown Under Different Culture Conditions," Glycobiology, vol. 5(8), pp. 813-822 (1995).
Mori, K. et al., "Engineering Chinese Hamster Ovary Cells to Maximize Effector Function of Produced Antibodies Using FUT8 siRNA," Biotechnology and Bioengineering, vol. 88 (7) pp. 901-908 (2004).
Notice of Opposition filed in European Patent No. EP2073842B1,English Translation, dated Sep. 29, 2015, 184 pages.
Printout of the page of the ATCC site "General information" for the line K562 bearing the No. ATCC CCL-243, Apr. 8, 2015, 1 page.
Raju, T. S. et al., "Species-specific variation in glycosylation of IgG: evidence for the species-specific sialylation and branch-specific galactosylation and importance for engineering recombinant glycoprotein therapeutics," Glycobiology, vol. 10(5), pp. 477-486 (2000).
Reitman, Marc L. et al., "Mouse lymphoma cell lines resistant to pea lectin are defective in fucose metabolism," The Journal of Biological Chemistry, vol. 255 (20) pp. 9900-9906 (1983).
Ripka, J. et al., "Lectin Resistant CHO Cells: Selection of Four New Pea Lectin-Resistant Phenotypes," Somatic Cell and Molecular Genetics, vol. 12 (1), pp. 51-62(1986).
Running Deer, A. et al., "High-level Expression of Proteins in Mammalian Cells Using Transcription Regulatory Sequences from the Chinese Hamster EF-1alpha Gene," Biotechnol. Prog., vol. 20 (3), pp. 880-889 (2004).
Shields, RL et al., "Lack of fucose on human IgG1 N-linked oligosaccharide improves binding to human Fcgamma RIII and antibody-dependent cellular toxicity," The Journal of Biological Chemistry, vol. 277 (30) pp. 26733-26740 (2002).
Van Der Heyde, H. et al., "Platelet depletion by anti-CD41 (alphaIIb) mAb injection early but not late in the course of disease protects against Plasmodium berghei pathogenesis by altering the levels of pathogenic cytokines," Blood, vol. 105(5) pp. 1956-1963 (2005).
Westlin, W. et al., Alleviation of myocardial stunning by leukocyte and platelet depletion, Circulation, vol. 80 (6) pp. 1828-1836 (1989).
Yamane-Ohnuki, N. et al., Establishment of FUTB Knockout Chinese Hamster Ovary Cells: An Ideal Host Cell Line for Producing Completely Defucosylated Antibodies With Enhanced Antibody-Dependent Cellular Cytotoxicity, biotechnology and Bioengineering, vol. 87(5), pp. 614-622 (2004).
Zarbock, A. et al., "Complete reversal of acid-induced acute lung injury by blocking of platelet-neutrophil aggregation," The Journal of Clinical Investigation, vol. 116 (12), pp. 3211-3219 (2006).
U.S. Appl. No. 13/208,253, filed Aug. 11, 2011, Steffen Goletz.
U.S. Appl. No. 13/302,698, filed Nov. 22, 2011, Steffen Goletz.
U.S. Appl. No. 14/102,214, filed Dec. 10, 2013, Steffen Goletz.
U.S. Appl. No. 12/514,248, Jul. 1, 2016.
U.S. Appl. No. 12/514,248, Apr. 20, 2016.
U.S. Appl. No. 13/208,253, Jun. 18, 2012.
U.S. Appl. No. 13/302,698, Feb. 3, 2012.
U.S. Appl. No. 13/302,698, Nov. 16, 2011.
U.S. Appl. No. 13/302,698, Aug. 23, 2013.
U.S. Appl. No. 13/302,698, May 10, 2013.
U.S. Appl. No. 13/302,698, Nov. 7, 2012.
U.S. Appl. No. 14/102,214, Jan. 20, 2016.
U.S. Appl. No. 14/102,214, Jul. 22, 2015.
U.S. Appl. No. 14/102,214, Jan. 13, 2015.
"Sequence 628 from Patent WO 2005/016962," (2005) XP002430727.
Agrawal, et al. "Cancer-associated MUC1 mucin inhibits human T-cell proliferation, which is reversible by IL-2.", Natl. Med., 4(1):43-9 (1998).
Albert, "Dendritic cells acquire antigen from apoptotic cells and induce class I-restricted CTLs," Nature, 392:86-89 (1998).
Allison A. et al., "The role of cytokines in the action of immunological adjuvants," Vaccine Design the Role of Cytokine Networks. Gregoriadis ed., NATO ASI Series A: Life Sciences, vol. 293, pp. 1-9, Plenum Press, NY (1997).
Anderson. "Human Gene Therapy". Science, vol. 256, 1992, pp. 808-813.
Annex 1 submitted in European Patent Application No. 07 818 090.8, Characterization of the Claimed Host Cell Lines and Associated Advantages When Using These Host Cells for Manufacturing Glycorpoteins, Jan. 14, 2011.
Annex 2 submitted in European Patent Application No. 07 818 090.8, "Advantages Achieved with Antibodies Obtainable by the Claimed Production Method—Induction of Target Cell Lysis," Jan. 14, 2011.
Baca et at, "Antibody Humanization Using Monovalent Phage Display," The Journal of Biological Chemistry, vol. 272, No. 16, Issue of Apr. 18, pp. 10678-10684 (1997).
Bagshawe, K. et al., "Antibody-Directed Enzyme Prodrug Therapy (ADEPT) for Cancer," Expert Opinion on Biological Therapy, vol. 4, No. 11, pp. 1777-1789 (2004).
Bain et al., "Structural Basis for Distinct Binding Properties of the Human Galectins to Thomsen-Friedenreich Antigen," PLoS One, Sep. 2011. vol. 6, Issue 9: e25007 (10 pgs).
Baumeister (PharmaChem, 2006, vol. 5, No. 4, pp. 21-24).

(56) References Cited

OTHER PUBLICATIONS

Baumeister and Goletz, "Voll Funktionsfahige Humane Dendritische Zelllinie," Laborwelt [online], vol. 6, 2005, url:http://www.nemod.com/downloads/nemoddc%20IN%20laborwelt%207.2.05.pdf.
Baumeister et al (Specialty Chemicals Magazine, 2005, vol. 25, pp. 46-48).
Baumeister, H., "Glycoengineering—a Technology for Production of Glycoproteins," Journal of Biotechnology, Nov. 2004, pp. 10-11.
Benoist, H. et al., "Studies on the Susceptibility to NK-Mediated Lysis and the Simultaneous Expression of Various Surface Molecules in Anthracyclin-Treated K562 Cells and in Four K562 Cell Clones," Immunology Letters, vol. 34, pp. 45-55 (1992).
Berd, "Autologous hapten-modified melanoma vaccine as postsurgical adjuvant treatment after resection of nodal metastases," J. Clin. Oncol., 15:2359-2370 (1997).
Berthier-Vergnes, "Induction of IgG Antibodies Directed to a M.sub.r 31,000 Melanoma Antigen in Patients Immunized with Vaccinia Virus Melanoma Oncolysates," Cancer Res. 54:2433-2439 (1994).
Binder, "Cutting Edge: Heat Shock Protein gp96 Induces Maturation and Migration of CD11c* Cells In Vivo," J. Immunol.; 165:6029-6035 (2000).
Boel, E. et al., "Functional Human Monoclonal Antibodies of All Isotypes Constructed from Phage Display Library-Derived Single-Chain Fv Antibody Fragments," Journal of Immunological Methods, vol. 239, Issues 1-2, pp. 153-166 (2000).
Bohm et al., "Carbohydrate Recognition on MUC1-Expressing Targets Enhances Cytoxicity of a T cell Subpopulatlon", Scandinavian Journal of Immunology, vol. 46. No. 1, pp. 27-34. XP-002323076 (1997).
Bomford et al., "The control of the antibody isotype responses to recombinant human immunodeficiency virus gp120 antigen by adjuvants," Aids Res. Hum. Retroviruses, 8:1765 et seq. (1992).
Bonig et al. "Gylcosylated vs non-glycosylated granulocyte colony-stimulating factor (G-CSF)—results of a prospective randomised mononcentre study," Bone Marrow Trans. 25: 259-264 (2001).
Bourdon, "Inhibition of Tumoral Graft Growth by Pretreatment with Normal or Heat-modified Tumoral Cells," Ann. Immunology 1, 43-63 (1981).
Brechbiel, M. et al., "Synthesis of 1-(p-Isothiocyanatabenzyl) Derivatives of DTPA and EDTA. Antibody Labeling and Tumor-Imaging Studies," Inorganic Chemistry, vol. 25, No. 16, pp. 2772-2781 (1986).
Brummelkamp, et al. "A System for Stable Expression of Short Interfering RNAs in Mammalian Cells". Science, vol. 296, 2002, pp. 550-553.
Burgess, W. et al., "Possible Dissociation of the Heparin-Binding and Mitogenic Activities of Heparin-Binding (Acidic Fibroblast) Growth Factor-1 from its Receptor-Binding Activities by Site-Directed Mutagenesis of a Single Lysine Residue," TheJournal of Cell Biology, vol. 111, No. 5, pp. 2129-2138 (1990).
Butschak, G., et al., "Isolation and Characterization of Thomsen-Friedenreich-Specific Antibodies From Human Serum," Tumor Biology, vol. 23, No. 3, pp. 113-122 (2002).
Cao et al., "Immunodetection of Epithelial Mucin (MUC1, MUC3) and Mucin-associated Glycotopes (TF, Tn, and sialosyl-Tn) in Benign and Malignant Lesions of Colonic Epithelium: Apolar Localization Corresponds to Malignant Transformation", VirchowsArchiv, vol. 431, No. 3, pp. 159-166, XP-002323077, (1997).
Cao, Y. et al., "Expression of CD175 (Tn), CD175s (Sialosyl-Tn) and CD176 (Thomsen-Friedenreich Antigen) on Malignant Human Hernatopoietic Cells," International Journal of Cancer, vol. 123, pp. 89-99 (2008).
Carbone, M. et al., "Multistep and Multifactorial Carcinogenesis: When Does a Contributing Factor Become a Carcinogen?," Seminars in Cancer Biology, vol. 14, pp. 399-405 (2004).
Casset, F. F et al., "A Peptide Mimetic of an Anti-CD4 Monoclonal Antibody by Rational Design," Biochemical and Biophysical Research Communications, vol. 307, Issue 1, pp. 198-205 (2003).
Cavaliere, "Selective heat sensitivity of cancer cells. Biochemical and clinical studies," Cancer 20:1351-1381 (1967).
Check, "Protection against transplanted and spontaneous lymphoma by inoculation of heat-altered syngeneic tumor cells in splenectomized mice," Cancer, 34:197-203 (1974).
Chen Z. et al., "Efficient Antitumor Immunity Derived From Muturation of Dendritic Cells That had Phagocytosed Apoptotic/Necrotic Tumor Cells," International Journal of Cancer, vol. 93. No. 4, pp. 539-548 (2001).
Chen, Y. et al., "Selection and Analysis of an Optimized Anti-VEGF Antibody: Crystal Structure of an Affinity-Matured FAB in Complex with Antigen," Journal of Molecular Biology, vol. 293, Issue 4, pp. 865-881 (1999).
Chothia, C. et al., "Canonical Structures for the Hypervariable Regions of Immunoglobulins," Journal of Molecular Biology, vol. 196, Issue 4, pp. 901-917 (1987).
Chothia, C. et al., "Conformations of Immunoglobulin Hypervariable Regions," Nature, vol. 342, pp. 877-883 (1989).
Chothia, C. et al., "Structural Repertoire of the Human V.sub.h Segments," Journal of Molecular Biology, vol. 227, Issue 3, pp. 799-817 (1992).
Chothia, C. et al., "The Predicted Structure of Immunoglobulin D1.3 and its Comparison with the Crystal Structure," Science, vol. 233, pp. 755-758 (1986).
Clausen, H., et al., "Monoclonal Antibodies Directed to the Blood Group a Associated Structure Galactosyl—A Specificity and Relation to the Thomsen-Friedenreich Antigen," Molecular Immunology, vol. 25, No. 2, pp. 199-204 (1988).
Clayman (ed.). The American Medical Association Encyclopedia of Medicine at 573-574, 576 and 1034 (1989).
Cox et al., "Adjuvants—A classification and review of their modes of action," Vaccine, vol. 15, pp. 248 et seq., (1997).
Cox et al., "Development of an Influenza-ISCOM.TM. Vaccine," in Vaccine Design at pp. 33-49 (1997).
Croce, M.V., et al., "The Use of Carbohydrate Antigens for the Preparation of Vaccines for Therapy in Breast Cancer," Drugs of Today, vol. 38, No. 11, pp. 759-768 (2002).
Cryz, Jr., S.J., Immunotherapy and Vaccines, edited by Stanley J. Cryz, pp. 3-11, VCH, Weinheim, Germany (1991).
Czuczman, M. et al., "Treatment of Patients with Low-Grade B-Cell Lymphoma with the Combination of Chimeric Anti-CD20 Monoclonal Antibody and CHOP Chemotherapy," Journal of Clinical Oncology, vol. 17, No. 1, pp. 268-276 (1999).
Dai, J. et al., "Effect of Desialyation on Binding, Affinity, and Specificity of 56 Monoclonal Antibodies Against MUC1 Mucin," Tumor Biology, vol. 19, pp. 100-110 (1998).
Dall'Olio, et al., "Expression of beta-galactoside alpha 2,6-sialyltransferase does not alter the susceptibility of human colon cancer cells to NK-mediated cell lysis." Glycobiology. 7:507-513 (1997).
Dermer, G., "Another Anniversary for the War on Cancer," Bio/Technology, vol. 12, p. 320 (1994).
Dickson, "Hyperthermia in the treatment of cancer," Lancet, 1:202-205 (1979).
Amit, M. et al. "Derivation and spontaneous differentiation of human embryonic stem cells," Journal of Anatomy, vol. 200: 225-232 (2002).
Additional experimental data, filed in EP2073842B1, (Annex 1), 7 pages (D34) (Feb. 6, 2012).
Advantages achieved with antibodies obtainable by the claimed production method—induction of target cell lysis, filed in EP2073842B1, (Annex 2), 4 pages (D35) (Jan. 14, 2011).
Characterization of the claimed host cell lines and associated advantages when using these host cells for manufacturing glycoproteins, filed in EP2073842B1, (Annex 1), 4 pages (D36) (Jan. 14, 2011).
Confirmation of Withdrawal of Application, European Application No. EP 06 090 171.7, dated Mar. 28, 2008, 1 page. (D8).
Confirmation of Withdrawal of Application, European Patent Application, EP 06 090 190.7, dated Apr. 15, 2008, 1 page. (D9).
CV and Publications of Stephan Hinderlich filed in EP2073842B1, 3 pages (2016).

(56) References Cited

OTHER PUBLICATIONS

Experimental Test of the Cells DSM ACC 2807 (NM-H9D8-E6) and DSM ACC 2856 (NM-H9D8-E6Q12) filed in EP2073842B1 (D25) on Feb. 16, 2015, 22 pages.

Fernandes, D. et al., "Demonstrating comparability of antibody glycosylation during biomanufacturing," Eur Biopharmaceutical Rev., 106-110 (Summer 2005).

Hossler, P. et al., "Optimal and consistent protein glycosylation in mammalian cell culture," Glycobiol., vol. 19(9): 936-949 (2009).

Huang, L. et al.,"Impact of variable domain glycosylation on antibody clearance: An LC/MS characterization," Anal Biochem., vol. 349:197-207 (2006).

Jenkins, N. et al., "Getting the glycosylation right: implications for the biotechnology industry," Nat Biotechnology, vol. 14: 975-981 (1996).

Lipscomb, M. et al., "Effect of production method and gene amplification on the glycosylation pattern of a secreted reporter protein in CHO cells," Biotechnol Prog., vol. 21: 40-49 (2005).

NCI Drug Dictionary anti-TA-MUC1 monoclonal antibody PankoMab filed in EP2073842B1, 1 page.

Nimmerjahn, F. et al., "Agalactosylated IgG antibodies depend on cellular Fc receptros for in vivo activity," PNAS, vol. 104(20): 8433-8437 (2017).

PankoMab HEK / H9D8: Overlay chromatograms filed in EP2073842B1 (D31) 3 pages (2016).

Presta, L. "Selection, Design, and engineering of therapeutic antibodies, Molecular mechanisms in allergy and clinical immunology," J Allergy Clin Immunol., vol. 116:731-736 (2005).

Product Sheet ATCC—293 [HEK-293] (ATCC® CRL-1573TM) filed in EP2073842B1 (D29) 3 pages (2016).

Report on experimental tests of the cells DSM ACC 2807 (NM-H9D8-E6) and ; DSM ACC 2856 (NM-H9D8-E6Q12) filed in EP2073842B1 (D33) 11 pages (2016).

Umana, P. et al., "Engineered glycoforms of an antineuro-blastoma IgG1 with optimized antibody-dependent cellular cytotoxic activity," Nature Biotechnology, vol. 17:176-180 (1999).

Yoshimura, M. et al., "Bisecting N-Acetylglucosamine on K562 Cells Suppresses Natural Killer Cytotoxicity and Promotes Spleen Colonization," Cancer Res., vol. 56:412-418 (1996).

Ohyama, et al. Natural killer cells attack tumor cells expressing high levels of sialyl Lewis x ollgosaccharides. PNAS, vol. 99, No. 21, 2002, pp. 13789-13794.

Olsvik, O. et al., "Magnetic Separation Techniques in Diagnostic Microbiology," Clinical Microbiology Reviews , vol. 7, No. 1, pp. 43-54 (1994).

Ouagari, et al. "Glycophorin a Protects K562 Cells from Natural Killer Cell Attack". The Journal of Biological Chemistry, vol. 270, No. 45, 1995, pp. 26970-26975.

Owens, et al. "Identification of two short internal ribosome entry sites selected from libraries of random oligonucleotides". PNAS, vol. 98, No. 4, 2001, pp. 1471-1476.

Paddison, et al. "Short hairpin RNAs (shRNAs) induce sequence-specific silencing in mammalian cells". Genes & Development, vol. 16, 2002, pp. 948-958.

Pahlsson, et al., "Biochemical characterization of the O-glycans on recombinant glycophorin as expressed in Chinese hamster ovary cells."Glycoconj. J., 11:43-50 (1994).

Panka, D. et al., "Variable Region Framework Differences Result in Decreased or Increased Affinity of Variant Anti-Digoxin Antibodies," PNAS, vol. 85, No. 9, pp. 3080-3084 (1988).

Pascalis, R. et al., "Grafting of 'Abbreviated' Complementarity-Determining Regions Containing Specificity-Determining Residues Essential for Ligand Contact to Engineer a Less Immunogenic Humanized Monoclonal Antibody," The Journal of Immunology,vol. 169, pp. 3076-3084 (2002).

Paul, W. E. (Ed.), Fundamental Immunology, p. 1007-1009, Raven Press, NY (1989).

Peach, R. et al., "Complementarity Determining Region 1 (CDR1)- and CDR3-Analogous Regions in CTLA-4 and CD28 Determine the Binding to B7-1," Journal of Experimental Medicine, vol. 180, No. 6, pp. 2049-2058 (1994).

Peters, L. et al., "Preparation of Immuno-Therapeutic Autologous Tumor Cell Vaccines from Solid Tumors," Cancer Research, vol. 39, pp. 1353-1360 (1979).

Phillips, T., Analytical Techniques in Immunochemistry. pp. 307-310, Marcel Dekker, NY (1992).

Price, "Effect of heat and glutaraldehyde upon the immunogenicity of Meth A sarcoma cells,"Br. J. Cancer 40:663-665 (1979).

Price, M. et al., "Summary Report on the ISOBM TD-4 Workshop: Analysis of 56 Monoclonal Antibodies Against the MUC1 Mucin," Tumor Biology, vol. 19, Suppl. 1, pp. 1-20 (1998).

Raju et al., "Glycoengineering of Therapeutic Clycoproteins: In Vitro Galactosylation and Sialylation of Glycoproteins with Terminal N-Acetylgulocosamine and Galactose Residues," Biochemistry, pp. 8868-8876 (2001).

Raska et at, "Glycosylation Patterns of HIV-1 gp120 Depend on the Type of Expressing Cells and Affect Antbody Recognition," Journal of Biological Chemistry, vol. 285, No. 27, Jul. 2, 2010, pp. 20860-20869.

Ravn at al., "Thomsen-Friedertreich disaccharide as antigen for in vivo tumor targeting with multivalent scFvs," Cancer Immunol Immunother (2007) 56:1345-1357.

Restifo, "Building better vaccines: how apoptotic cell death can induce inflammation and activate innate and adaptive immunity," Curr. Opin. Immunol., 12:597-603 (2000).

Riemer AB et al. "Induction of IgG antibodies against the GD2 carbohydrate tumor antigen by vaccination with peptide mimotopes," European Journal of Immunology, 36(5): 1267-1274 (2006).

Romani et al., "Proliferating dendritic cell progenitors in human blood," J. Exp. Med., 180:83-93 (1994).

Rooman, M. et al., "Amino Acid Sequence Templates Derived from Recurrent Turn Motifs in Proteins: Critical Evaluation of Their Predictive Power," Protein Engineering, vol. 3, No. 1, pp. 23-27 (1989).

Rudikoff, S. et al., "Single Amino Acid Substitution Altering Antigen-Binding Specificity," PNAS, vol. 79, No. 6, pp. 1979-1983 (1982).

Saerens, D. et al., "Identification of a Universal VHH Framework to Graft Non-Canonical Antigen-Binding Loops of Camel Single-Domain Antibodies," Journal of Molecular Biology, vol. 352, Issue 3, pp. 597-607 (2005).

Samali et al., FEBS Letters 461(3):306-310 (1999).

Santegoets, S. et al., "In Vitro Priming of Tumor-Specific Cytotoxic T Lymphocytes Using Allogeneic Dendritic Cells Derived from the Human MUTZ-3 Cell Line," Cancer Immunology Immunotherapy, vol. 55, No. 12, pp. 1480-1490 (2006).

Sauter Birthe et al., "Consequences of Cell Death: Exposure to Necrotic Tumor Cells, but Not Primary Tissue Cells or Apoptotic Cells, Induces the Maturation of Immunostimulatory Dendritic Cells," Journal of Experimental Medicine, vol. 191, No. 3,pp. 423-433 (2000).

Scheibel, T. et al., "Contribution of N- and C-Terminal Domains to the Function of Hsp90 in *Saccharomyces cerevisiae*," Molecular Microbiology, vol. 34, No. 4, pp. 701-713 (1999).

Schild, "gp96—the immune system's Swiss army knife," Nat. Immunol. 1:100-101 (2000).

Schlom, J., "Monoclonal Antibodies: They're More and Less Than you Think," Molecular Foundations of Oncology, Broder, S., Ed., Chapter 6, pp. 95-134 (1991).

Schneider, D. et al., "Thermostability of Membrane Protein Helix-Helix Interaction Elucidated by Statistical Analysis," FEBS Letters, vol. 532, No. 1-2, pp. 231-236 (2002).

Schneider, F. et al., "Overexpression of Sialyltransferase CMP-Sialic Acid: Gal.beta.1,3BaINAc-R .alpha.6-Sialyltransferase is Related to Poor Patient Survival in Human Colorectal Carcinomas," Cancer Research, vol. 61, No. 11, pp. 4605-4611 (2001).

Selawry, "Hyperthermia in Tissue-cultured Cells of Malignant Origin," Cancer Res., 17:785-791 (1957).

(56) References Cited

OTHER PUBLICATIONS

Sensi, "Clonal Expansion of Lymphocytes in Human Metastases after Treatment With a Hapten-modified Autologous Tumor Vaccine," Clin. Invest. 99:710-717 (1997).

Shaif-Muthana, "Dead or Alive: Immunogenicity of Human Melanoma Cells When Presented by Dendritic Cells," Cancer Res., 60:6441-6447 (2000).

Shinkawa, T. et al. "The Absence of Fucose but Not the Presence of Galactose or Bisecting N-Acetylglucosamine of Human IgG1 Complex-type Oligosaccharides Shows the Critical Rile of Enhancing Antibody-dependent Cellular Cytotoxicity," The Journal ofBiological Chemistry, 278(5): 3466-3473 (2003).

Sigma-Aldrich catalog, Granulocyte Macrophage Colony—Stimulating Factor Human, dowloaded 2011.

Sivanandham, et al. "Cancer Vaccines: Clinical Applications". Principles and Practice of the Biologic Therapy of Cancer, Third Edition, S. Rosenberg, 2000, pp. 632-647, Lippincott Williams & Wilkins, Philadelphia, PA.

Skerra, A., "Alternative Non-Antibody Scaffolds for Molecular Recognition," Current Opinion in Biotechnology, vol. 18, Issue 4, pp. 295-304 (2007).

Skerra, A., "Engineered Protein Scaffolds for Molecular Recognition," Journal of Molecular Recognition, vol. 13, Issue 4, pp. 167-187 (2000).

Slovin, S.F., et al., "Thomsen-Friedenreich (TF) Antigen as a Target for Prostate Cancer Vaccine: Clinical Trial Results With TF cluster (c)-KLH Plus QS21 Conjugate Vaccine in Patients With Biochemically Relapsed Prostate Cancer," Cancer ImmunologyImmunotherapy, vol. 54, No. 7, pp. 694-702 (2005).

Snippe et al., "Adjuvant Directed Immune Specificity at the Epitope Level. Implications for Vaccine Development. A Model Study Using Semliki Forest Virus Infection of Mice," Vaccine Design: The Role of Cytokine Networks, pp. 155-166 (1997).

Somersan S. et al., "Primary Tumor Tissue Lysates Are Enriched in Heat Shock Proteins and Induce the Maturation of Human Dendritic Cells," Journal of Immunology, vol. 167, No. 9, pp. 4844-4852 (2001).

Springer, et al., "Immunoreactive T and Tn epitopes in cancer diagnosis, prognosis, and immunotherapy." J. Mol. Med., 75:594-602 (1997).

Springer, G.E, et al., "Origin of Anti Thomsen Friedenreich and TN Agglutinins in Man and in White Leghorn Chicks," British Journal of Haematology, vol. 47, No. 3, pp. 453-460 (1981).

Stimmel, J. et al., "Yttrium-90 Chelation Properties of Tetraazatetraacetic Acid Macrocycles, Diethylenetriaminepentaacetic Acid Analogs, and a Novel Terpyridine Acyclic," Bioconjugate Chemistry, vol. 6, Issue 2, pp. 219-225 (1995).

Suzuki, T. et al., "A Comparison of the Genotoxicity of Ethylnitrosourea and Ethyl Methanesulfonate in IacZ Transgenic Mice (Muta.TM. Mouse)," Mutation Research, vol. 395, pp. 75-82 (1997).

Tachibana et al (Cytotechnology, 1991, vol. 6, pp. 219-226).

Takahashi et al., "Antitumor Effects of the Intravesical Instillation of Heat Killed Cells of the Lactobacillus casei Strain Shirota on the Murine Orthotopic Bladder Tumor MBT-2," Journal of Urology, vol. 166, No. 6, pp. 2506-2511 (2001).

Takano, Y., et al., "Lymph Node Metastasis-Related Carbohydrate Epitopes of Gastric Cancer With Submucosal Invasion," Surgery Today 2000, vol. 30, No. 12, pp. 1073-1082 (2000).

Thatcher, N. et al., "Anti-T Antibody in Malignant Melanoma Patients, Influence of Response Survival Following Chemotherapy—Changes in Serum Levels Following C parvum, BCG Immunization," Cancer, vol. 46, No. 6, pp. 1378-1382 (1980).

\* cited by examiner

```
                        SEQUENCE LISTING

<160> NUMBER OF SEQ ID NOS: 23

<210> SEQ ID NO 1
<211> LENGTH: 187
<212> TYPE: PRT
<213> ORGANISM: Unknown
<220> FEATURE:
<223> OTHER INFORMATION: MTX resistant DHFR variant

<400> SEQUENCE: 1

Met Val Arg Pro Leu Asn Cys Ile Val Ala Val Ser Gln Asp Met Gly
1               5                   10                  15

Ile Gly Lys Asn Gly Asp Leu Pro Trp Pro Pro Leu Arg Asn Glu Trp
                20                  25                  30

Lys Tyr Phe Gln Arg Met Thr Thr Thr Ser Ser Val Glu Gly Lys Gln
            35                  40                  45

Asn Leu Val Ile Met Gly Arg Lys Thr Trp Phe Ser Ile Pro Glu Lys
        50                  55                  60

Asn Arg Pro Leu Lys Asp Arg Ile Asn Ile Val Leu Ser Arg Glu Leu
65                  70                  75                  80

Lys Glu Pro Pro Arg Gly Ala His Phe Leu Ala Lys Ser Leu Asp Asp
                85                  90                  95

Ala Leu Arg Leu Ile Glu Gln Pro Glu Leu Ala Ser Lys Val Asp Met
            100                 105                 110

Val Trp Ile Val Gly Gly Ser Ser Val Tyr Gln Glu Ala Met Asn Gln
        115                 120                 125

Pro Gly His Leu Arg Leu Phe Val Thr Arg Ile Met Gln Glu Phe Glu
    130                 135                 140
```

```
Ser Asp Thr Phe Phe Pro Glu Ile Asp Leu Gly Lys Tyr Lys Leu Leu
145                 150                 155                 160

Pro Glu Tyr Pro Gly Val Leu Ser Glu Val Gln Glu Glu Lys Gly Ile
                165                 170                 175

Lys Tyr Lys Phe Glu Val Tyr Glu Lys Asp
            180                 185

<210> SEQ ID NO 2
<211> LENGTH: 187
<212> TYPE: PRT
<213> ORGANISM: Unknown
<220> FEATURE:
<223> OTHER INFORMATION: MTX resistant DHFR variant

<400> SEQUENCE: 2

Met Val Gly Ser Leu Asn Cys Ile Val Ala Val Ser Gln Asn Met Gly
1               5                   10                  15

Ile Gly Lys Asn Gly Asp Leu Pro Trp Pro Leu Arg Asn Glu Ser
            20                  25                  30

Arg Tyr Phe Gln Arg Met Thr Thr Thr Ser Ser Val Glu Gly Lys Gln
            35                  40                  45

Asn Leu Val Ile Met Gly Lys Lys Thr Trp Phe Ser Ile Pro Glu Lys
50                  55                  60

Asn Arg Pro Leu Lys Gly Arg Ile Asn Leu Val Leu Ser Arg Glu Leu
65                  70                  75                  80

Lys Glu Pro Pro Gln Gly Ala His Phe Leu Ser Arg Ser Leu Asp Asp
                85                  90                  95

Ala Leu Lys Leu Thr Glu Gln Pro Glu Leu Ala Asn Lys Val Asp Met
                100                 105                 110

Val Trp Ile Val Gly Gly Ser Ser Val Tyr Lys Glu Ala Met Asn His
                115                 120                 125

Pro Gly His Leu Lys Leu Phe Val Thr Arg Ile Met Gln Asp Phe Glu
                130                 135                 140

Ser Asp Thr Phe Phe Pro Glu Ile Asp Leu Glu Lys Tyr Lys Leu Leu
145                 150                 155                 160

Pro Glu Tyr Pro Gly Val Leu Ser Asp Val Gln Glu Glu Lys Gly Ile
                165                 170                 175

Lys Tyr Lys Phe Glu Val Tyr Glu Lys Asn Asp
            180                 185

<210> SEQ ID NO 3
<211> LENGTH: 187
<212> TYPE: PRT
<213> ORGANISM: Unknown
<220> FEATURE:
<223> OTHER INFORMATION: MTX resistant DHFR variant

<400> SEQUENCE: 3

Met Val Gly Ser Leu Asn Cys Ile Val Ala Val Ser Gln Asn Met Gly
1               5                   10                  15

Ile Gly Lys Asn Gly Asp Leu Pro Trp Pro Leu Arg Asn Glu Ala
            20                  25                  30

Arg Tyr Phe Gln Arg Met Thr Thr Thr Ser Ser Val Glu Gly Lys Gln
            35                  40                  45

Asn Leu Val Ile Met Gly Lys Lys Thr Trp Phe Ser Ile Pro Glu Lys
50                  55                  60

Asn Arg Pro Leu Lys Gly Arg Ile Asn Leu Val Leu Ser Arg Glu Leu
65                  70                  75                  80
```

```
Lys Glu Pro Pro Gln Gly Ala His Phe Leu Ser Arg Ser Leu Asp Asp
                85                  90                  95

Ala Leu Lys Leu Thr Glu Gln Pro Glu Leu Ala Asn Lys Val Asp Met
            100                 105                 110

Val Trp Ile Val Gly Gly Ser Ser Val Tyr Lys Glu Ala Met Asn His
        115                 120                 125

Pro Gly His Leu Lys Leu Phe Val Thr Arg Ile Met Gln Asp Phe Glu
    130                 135                 140

Ser Asp Thr Phe Phe Pro Glu Ile Asp Leu Glu Lys Tyr Lys Leu Leu
145                 150                 155                 160

Pro Glu Tyr Pro Gly Val Leu Ser Asp Val Gln Glu Glu Lys Gly Ile
                165                 170                 175

Lys Tyr Lys Phe Glu Val Tyr Glu Lys Asn Asp
                180                 185

<210> SEQ ID NO 4
<211> LENGTH: 187
<212> TYPE: PRT
<213> ORGANISM: Unknown
<220> FEATURE:
<223> OTHER INFORMATION: MTX resistant DHFR variant

<400> SEQUENCE: 4

Met Val Gly Ser Leu Asn Cys Ile Val Ala Val Ser Gln Asn Met Gly
1               5                   10                  15

Ile Gly Lys Asn Gly Asp Leu Pro Trp Pro Pro Leu Arg Asn Glu Gly
            20                  25                  30

Arg Tyr Phe Gln Arg Met Thr Thr Thr Ser Ser Val Glu Gly Lys Gln
        35                  40                  45

Asn Leu Val Ile Met Gly Lys Lys Thr Trp Phe Ser Ile Pro Glu Lys
    50                  55                  60

Asn Arg Pro Leu Lys Gly Arg Ile Asn Leu Val Leu Ser Arg Glu Leu
65                  70                  75                  80

Lys Glu Pro Pro Gln Gly Ala His Phe Leu Ser Arg Ser Leu Asp Asp
                85                  90                  95

Ala Leu Lys Leu Thr Glu Gln Pro Glu Leu Ala Asn Lys Val Asp Met
            100                 105                 110

Val Trp Ile Val Gly Gly Ser Ser Val Tyr Lys Glu Ala Met Asn His
        115                 120                 125

Pro Gly His Leu Lys Leu Phe Val Thr Arg Ile Met Gln Asp Phe Glu
    130                 135                 140

Ser Asp Thr Phe Phe Pro Glu Ile Asp Leu Glu Lys Tyr Lys Leu Leu
145                 150                 155                 160

Pro Glu Tyr Pro Gly Val Leu Ser Asp Val Gln Glu Glu Lys Gly Ile
                165                 170                 175

Lys Tyr Lys Phe Glu Val Tyr Glu Lys Asn Asp
                180                 185

<210> SEQ ID NO 5
<211> LENGTH: 187
<212> TYPE: PRT
<213> ORGANISM: Unknown
<220> FEATURE:
<223> OTHER INFORMATION: MTX resistant DHFR variant

<400> SEQUENCE: 5

Met Val Gly Ser Leu Asn Cys Ile Val Ala Val Ser Gln Asn Met Gly
```

```
            1               5                  10                 15
Ile Gly Lys Asn Gly Asp Tyr Pro Trp Pro Leu Arg Asn Glu Phe
                20                  25                 30

Arg Tyr Phe Gln Arg Met Thr Thr Thr Ser Ser Val Glu Gly Lys Gln
            35                  40                 45

Asn Leu Val Ile Met Gly Lys Lys Thr Trp Phe Ser Ile Pro Glu Lys
        50                  55                 60

Asn Arg Pro Leu Lys Gly Arg Ile Asn Leu Val Leu Ser Arg Glu Leu
65                  70                  75                 80

Lys Glu Pro Pro Gln Gly Ala His Phe Leu Ser Arg Ser Leu Asp Asp
                85                  90                 95

Ala Leu Lys Leu Thr Glu Gln Pro Glu Leu Ala Asn Lys Val Asp Met
                100                 105                110

Val Trp Ile Val Gly Gly Ser Ser Val Tyr Lys Glu Ala Met Asn His
            115                 120                125

Pro Gly His Leu Lys Leu Phe Val Thr Arg Ile Met Gln Asp Phe Glu
130                 135                 140

Ser Asp Thr Phe Phe Pro Glu Ile Asp Leu Glu Lys Tyr Lys Leu Leu
145                 150                 155                160

Pro Glu Tyr Pro Gly Val Leu Ser Asp Val Gln Glu Glu Lys Gly Ile
                165                 170                175

Lys Tyr Lys Phe Glu Val Tyr Glu Lys Asn Asp
            180                 185
```

<210> SEQ ID NO 6
<211> LENGTH: 187
<212> TYPE: PRT
<213> ORGANISM: Unknown
<220> FEATURE:
<223> OTHER INFORMATION: MTX resistant DHFR variant

<400> SEQUENCE: 6

```
Met Val Gly Ser Leu Asn Cys Ile Val Ala Val Ser Gln Asn Met Gly
1               5                  10                 15

Ile Gly Lys Asn Gly Asp Arg Pro Trp Pro Leu Arg Asn Glu Phe
                20                  25                 30

Arg Tyr Phe Gln Arg Met Thr Thr Thr Ser Ser Val Glu Gly Lys Gln
            35                  40                 45

Asn Leu Val Ile Met Gly Lys Lys Thr Trp Phe Ser Ile Pro Glu Lys
        50                  55                 60

Asn Arg Pro Leu Lys Gly Arg Ile Asn Leu Val Leu Ser Arg Glu Leu
65                  70                  75                 80

Lys Glu Pro Pro Gln Gly Ala His Phe Leu Ser Arg Ser Leu Asp Asp
                85                  90                 95

Ala Leu Lys Leu Thr Glu Gln Pro Glu Leu Ala Asn Lys Val Asp Met
                100                 105                110

Val Trp Ile Val Gly Gly Ser Ser Val Tyr Lys Glu Ala Met Asn His
            115                 120                125

Pro Gly His Leu Lys Leu Phe Val Thr Arg Ile Met Gln Asp Phe Glu
130                 135                 140

Ser Asp Thr Phe Phe Pro Glu Ile Asp Leu Glu Lys Tyr Lys Leu Leu
145                 150                 155                160

Pro Glu Tyr Pro Gly Val Leu Ser Asp Val Gln Glu Glu Lys Gly Ile
                165                 170                175

Lys Tyr Lys Phe Glu Val Tyr Glu Lys Asn Asp
```

180                 185

<210> SEQ ID NO 7
<211> LENGTH: 187
<212> TYPE: PRT
<213> ORGANISM: Unknown
<220> FEATURE:
<223> OTHER INFORMATION: MTX resistant DHFR variant

<400> SEQUENCE: 7

Met Val Gly Ser Leu Asn Cys Ile Val Ala Val Ser Gln Asn Met Gly
1               5                   10                  15

Ile Gly Lys Asn Gly Asp Phe Pro Trp Pro Pro Leu Arg Asn Glu Phe
            20                  25                  30

Arg Tyr Phe Gln Arg Met Thr Thr Thr Ser Ser Val Glu Gly Lys Gln
        35                  40                  45

Asn Leu Val Ile Met Gly Lys Lys Thr Trp Phe Ser Ile Pro Glu Lys
    50                  55                  60

Asn Arg Pro Leu Lys Gly Arg Ile Asn Leu Val Leu Ser Arg Glu Leu
65                  70                  75                  80

Lys Glu Pro Pro Gln Gly Ala His Phe Leu Ser Arg Ser Leu Asp Asp
                85                  90                  95

Ala Leu Lys Leu Thr Glu Gln Pro Glu Leu Ala Asn Lys Val Asp Met
            100                 105                 110

Val Trp Ile Val Gly Gly Ser Ser Val Tyr Lys Glu Ala Met Asn His
        115                 120                 125

Pro Gly His Leu Lys Leu Phe Val Thr Arg Ile Met Gln Asp Phe Glu
    130                 135                 140

Ser Asp Thr Phe Phe Pro Glu Ile Asp Leu Glu Lys Tyr Lys Leu Leu
145                 150                 155                 160

Pro Glu Tyr Pro Gly Val Leu Ser Asp Val Gln Glu Glu Lys Gly Ile
                165                 170                 175

Lys Tyr Lys Phe Glu Val Tyr Glu Lys Asn Asp
            180                 185

<210> SEQ ID NO 8
<211> LENGTH: 187
<212> TYPE: PRT
<213> ORGANISM: Unknown
<220> FEATURE:
<223> OTHER INFORMATION: MTX resistant DHFR variant

<400> SEQUENCE: 8

Met Val Arg Pro Leu Asn Cys Ile Val Ala Val Ser Gln Asn Met Gly
1               5                   10                  15

Ile Gly Lys Asn Gly Asp Arg Pro Trp Pro Pro Leu Arg Asn Glu Phe
            20                  25                  30

Lys Tyr Phe Gln Arg Met Thr Thr Thr Ser Ser Val Glu Gly Lys Gln
        35                  40                  45

Asn Leu Val Ile Met Gly Arg Lys Thr Trp Phe Ser Ile Pro Glu Lys
    50                  55                  60

Asn Arg Pro Leu Lys Asp Arg Ile Asn Ile Val Leu Ser Arg Glu Leu
65                  70                  75                  80

Lys Glu Pro Pro Arg Gly Ala His Phe Leu Ala Lys Ser Leu Asp Asp
                85                  90                  95

Ala Leu Arg Leu Ile Glu Gln Pro Glu Leu Ala Ser Lys Val Asp Met
            100                 105                 110

```
Val Trp Ile Val Gly Gly Ser Ser Val Tyr Gln Glu Ala Met Asn Gln
        115                 120                 125

Pro Gly His Leu Arg Leu Phe Val Thr Arg Ile Met Gln Glu Phe Glu
130                 135                 140

Ser Asp Thr Phe Phe Pro Glu Ile Asp Leu Gly Lys Tyr Lys Leu Leu
145                 150                 155                 160

Pro Glu Tyr Pro Gly Val Leu Ser Glu Val Gln Glu Lys Gly Ile
                165                 170                 175

Lys Tyr Lys Phe Glu Val Tyr Glu Lys Lys Asp
            180                 185

<210> SEQ ID NO 9
<211> LENGTH: 187
<212> TYPE: PRT
<213> ORGANISM: Unknown
<220> FEATURE:
<223> OTHER INFORMATION: MTX-resistant DHFR variant

<400> SEQUENCE: 9

Met Val Arg Pro Leu Asn Cys Ile Val Ala Val Ser Gln Asn Met Gly
1               5                   10                  15

Ile Gly Lys Asn Gly Asp Tyr Pro Trp Pro Pro Leu Arg Asn Glu Phe
            20                  25                  30

Lys Tyr Phe Gln Arg Met Thr Thr Thr Ser Ser Val Glu Gly Lys Gln
        35                  40                  45

Asn Leu Val Ile Met Gly Arg Lys Thr Trp Phe Ser Ile Pro Glu Lys
    50                  55                  60

Asn Arg Pro Leu Lys Asp Arg Ile Asn Ile Val Leu Ser Arg Glu Leu
65                  70                  75                  80

Lys Glu Pro Pro Arg Gly Ala His Phe Leu Ala Lys Ser Leu Asp Asp
                85                  90                  95

Ala Leu Arg Leu Ile Glu Gln Pro Glu Leu Ala Ser Lys Val Asp Met
            100                 105                 110

Val Trp Ile Val Gly Gly Ser Ser Val Tyr Gln Glu Ala Met Asn Gln
        115                 120                 125

Pro Gly His Leu Arg Leu Phe Val Thr Arg Ile Met Gln Glu Phe Glu
130                 135                 140

Ser Asp Thr Phe Phe Pro Glu Ile Asp Leu Gly Lys Tyr Lys Leu Leu
145                 150                 155                 160

Pro Glu Tyr Pro Gly Val Leu Ser Glu Val Gln Glu Lys Gly Ile
                165                 170                 175

Lys Tyr Lys Phe Glu Val Tyr Glu Lys Lys Asp
            180                 185

<210> SEQ ID NO 10
<211> LENGTH: 18
<212> TYPE: PRT
<213> ORGANISM: Unknown
<220> FEATURE:
<223> OTHER INFORMATION: Secretion peptide signal

<400> SEQUENCE: 10

Met Trp Leu Gly Ser Leu Leu Leu Leu Gly Thr Val Ala Cys Ser Ile
1               5                   10                  15

Ser Ala

<210> SEQ ID NO 11
<211> LENGTH: 117
```

```
<212> TYPE: PRT
<213> ORGANISM: Unknown
<220> FEATURE:
<223> OTHER INFORMATION: Variable heavy chain of the antibody Panko -1

<400> SEQUENCE: 11
```

Glu Val Lys Leu Val Glu Ser Gly Gly Gly Leu Val Gln Pro Gly Gly
1               5                   10                  15

Ser Met Lys Leu Ser Cys Ala Ala Ser Gly Phe Thr Phe Ser Asp Ala
            20                  25                  30

Trp Met Asp Trp Val Arg Gln Ser Pro Glu Lys Gly Leu Glu Trp Val
        35                  40                  45

Ala Glu Ile Arg Ser Lys Ala Asn Asn His Ala Thr Tyr Tyr Ala Glu
50                  55                  60

Ser Val Lys Gly Arg Phe Thr Ile Ser Arg Asp Val Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Thr Arg Gly Gly Tyr Gly Phe Asp Tyr Trp Gly Gln Gly Thr
            100                 105                 110

Thr Leu Thr Val Ser
            115

```
<210> SEQ ID NO 12
<211> LENGTH: 113
<212> TYPE: PRT
<213> ORGANISM: Unknown
<220> FEATURE:
<223> OTHER INFORMATION: Variable light chain of the antibody Panko 1

<400> SEQUENCE: 12
```

Asp Ile Val Leu Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Asp Gly Thr Lys Leu Glu Leu Lys
            100                 105                 110

Arg

```
<210> SEQ ID NO 13
<211> LENGTH: 116
<212> TYPE: PRT
<213> ORGANISM: Unknown
<220> FEATURE:
<223> OTHER INFORMATION: Variable heavy chain of the antibody Panko 2

<400> SEQUENCE: 13
```

Glu Val Lys Leu Val Glu Ser Gly Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

```
Trp Met Asn Trp Val Arg Gln Ser Pro Glu Lys Gly Leu Glu Trp Val
        35                  40                  45

Ala Glu Ile Arg Leu Lys Ser Asn Asn Tyr Thr Thr His Tyr Ala Glu
 50                  55                  60

Ser Val Lys Gly Arg Phe Thr Ile Ser Arg Asp Asp Ser Lys Ser Ser
 65                  70                  75                  80

Val Ser Leu Gln Met Asn Asn Leu Arg Val Glu Asp Thr Gly Ile Tyr
                 85                  90                  95

Tyr Cys Thr Arg His Tyr Tyr Phe Asp Tyr Trp Gly Gln Gly Thr Thr
                100                 105                 110

Leu Thr Val Ser
        115

<210> SEQ ID NO 14
<211> LENGTH: 113
<212> TYPE: PRT
<213> ORGANISM: Unknown
<220> FEATURE:
<223> OTHER INFORMATION: Variable light chain of the antibody Panko 2

<400> SEQUENCE: 14

Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
            20                  25                  30

Asn Gly Ile Thr Tyr Phe Phe Trp Tyr Leu Gln Lys Pro Gly Leu Ser
        35                  40                  45

Pro Gln Leu Leu Ile Tyr Gln Met Ser Asn Leu Ala Ser Gly Val Pro
 50                  55                  60

Asp Arg Phe Ser Ser Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Asn
                85                  90                  95

Leu Glu Leu Pro Pro Thr Phe Gly Gly Gly Thr Lys Leu Glu Ile Lys
                100                 105                 110

Arg

<210> SEQ ID NO 15
<211> LENGTH: 118
<212> TYPE: PRT
<213> ORGANISM: Unknown
<220> FEATURE:
<223> OTHER INFORMATION: Variable heavy chain of the antibody Cetuximab

<400> SEQUENCE: 15

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
 50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95
```

```
Arg Ala Leu Thr Tyr Tyr Asp Tyr Glu Phe Ala Tyr Trp Gly Gln Gly
            100                 105                 110

Thr Leu Val Thr Val Ser
        115

<210> SEQ ID NO 16
<211> LENGTH: 108
<212> TYPE: PRT
<213> ORGANISM: Unknown
<220> FEATURE:
<223> OTHER INFORMATION: Variable light chain of the antibody Cetuximab

<400> SEQUENCE: 16

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg
            100                 105

<210> SEQ ID NO 17
<211> LENGTH: 31
<212> TYPE: DNA
<213> ORGANISM: Artificial
<220> FEATURE:
<223> OTHER INFORMATION: Primer for FSH alpha chain

<400> SEQUENCE: 17
aaaggtacca tggattacta cagaaaatat g                                  31

<210> SEQ ID NO 18
<211> LENGTH: 29
<212> TYPE: DNA
<213> ORGANISM: artificial
<220> FEATURE:
<223> OTHER INFORMATION: Primer for FSH alpha chain

<400> SEQUENCE: 18
aaaggatcct taagatttgt gataataac                                     29

<210> SEQ ID NO 19
<211> LENGTH: 30
<212> TYPE: DNA
<213> ORGANISM: Artificial
<220> FEATURE:
<223> OTHER INFORMATION: Primer for FSH beta chain

<400> SEQUENCE: 19
tttaagctta tgaagacact ccagtttttc                                    30

<210> SEQ ID NO 20
<211> LENGTH: 27
<212> TYPE: DNA
<213> ORGANISM: Artificial
```

```
<220> FEATURE:
<223> OTHER INFORMATION: Primer for FSH beta chain

<400> SEQUENCE: 20
tttggatcct tattctttca tttcacc                                          27

<210> SEQ ID NO 21
<211> LENGTH: 399
<212> TYPE: DNA
<213> ORGANISM: Artificial
<220> FEATURE:
<223> OTHER INFORMATION: cDNA sequence
<220> FEATURE:
<221> NAME/KEY: misc_feature
<222> LOCATION: (1)..(63)
<223> OTHER INFORMATION: TCR leader sequence

<400> SEQUENCE: 21
atggcctgcc ccggcttcct gtgggccctg gtgatcagca cctgcctgga attctccatg      60
gctaacagct gcgagctgac caacatcacc atcgccatcg agaaagagga atgccggttc     120
tgcatcagca tcaacaccac ctggtgcgcc ggctactgct acacccggga cctggtgtac     180
aaggaccccg ccaggcccaa gatccagaaa acctgcacct tcaaagaact ggtgtacgag     240
accgtgcggg tgcccggctg cgcccaccac gccgacagcc tgtacaccta ccccgtggcc     300
acccagtgcc actgcggcaa gtgcgacagc gacagcaccg actgcaccgt gaggggcctg     360
ggccccagct actgcagctt cggcgagatg aaagagtga                            399

<210> SEQ ID NO 22
<211> LENGTH: 5
<212> TYPE: PRT
<213> ORGANISM: Unknown
<220> FEATURE:
<223> OTHER INFORMATION: Epitope on MUC1 (Thr can be glycosylated)

<400> SEQUENCE: 22

Pro Asp Thr Arg Pro
1               5

<210> SEQ ID NO 23
<211> LENGTH: 30
<212> TYPE: PRT
<213> ORGANISM: Unknown
<220> FEATURE:
<223> OTHER INFORMATION: MUC1 peptide

<400> SEQUENCE: 23

Ala Pro Pro Ala His Gly Val Thr Ser Ala Pro Asp Thr Arg Pro Ala
1               5                   10                  15

Pro Gly Ser Thr Ala Pro Pro Ala His Gly Val Thr Ser Ala
            20                  25                  30
```

USE OF HUMAN CELLS OF MYELOID LEUKEMIA ORIGIN FOR EXPRESSION OF ANTIBODIES

CROSS REFERENCE TO RELATED APPLICATIONS

This application is a continuation of U.S. patent application Ser. No. 12/440,562, filed May 14, 2009, which is a national stage filing under 35 U.S.C. § 371 of International Application No. PCT/EP2007/007877, filed on Sep. 10, 2007, and claims the benefit of priority of European Application No. 06090162.6, filed on Sep. 10, 2006; European Application No. 06090171.7, filed on Sep. 18, 2006; European Application No. 06090190.7, filed on Oct. 13, 2006; and European Application No. 07090094.9, filed on May 4, 2007. All of these applications, including International Application No. PCT/EP2007/007877, are incorporated herein by reference in their entirety.

SUMMARY

The invention provides biotechnologically favourable methods for the production of protein molecule compositions and in particular antibody molecule compositions having increased activity and/or increased yield and/or improved homogeneity and a human glycosylation. It further provides novel host cells, nucleic acids, and protein molecule compositions.

INTRODUCTION

A key feature and challenge for the industry is the production of recombinant proteins and productivity, cost, homogeneity, and protein activity are key issues which remain to be optimised. Glycosylation is also a key issue in the production of high yields of homogenous recombinant glycoproteins which poses a series of critical problems for their production. Each current production cell line offers a series of different challenges and problems which are largely due to the complexity and species, tissue and site specificity of the glycosylation. Therefore, the optimisation of production systems in respect to glycosylation remains one of the key aspects for optimisation. This particularly, as differences in the glycosylation pattern often have a considerable impact on activity, immugenicity, bioavailability and half-life of the protein molecules. A detailed overview of glycosylation properties of different cell lines derived from different species and non-mammalian production systems is given in Jenkins et al (Getting the glycosylation right: implications for the biotechnology industry, Nat Biotechnology, 1996, 14: 975-981).

Antibodies are major tools for diagnosis and research, and likely to become the largest family of therapeutics. Over ten recombinant antibody therapeutics are on the market and hundreds in clinical development. A key feature and challenge for the industry is the production of recombinant antibodies ("rMAbs") and productivity, cost, homogeneity, and antibody activity are key issues which remain to be optimised. Nearly all therapeutic rMAbs on the market have been produced in the rodent cell lines from hamster (CHO) and mice (NS0 or Sp2/0). By far most of the rMABs in development are produced in rodent cells, and others are under development, however, none has been sufficient for optimising productivity, cost, homogeneity, and antibody activity.

Glycosylation is also a key issue in the production of high yields of homogenous and potent rMAbs which poses a series of critical problems for the production of rMAbs. Each current production cell line offers a series of different challenges and problems which are largely due to the complexity and species, tissue and site specificity of the glycosylation [Review: Royston Jefferis, CCE IX: Glycosylation of Recombinant Antibody Therapeutics; Biotechnol. Prog. 2005, 21, 11-16].

Therefore the optimisation of protein and in particular antibody production systems in respect to glycosylation remains one of the key aspects for optimisation.

The present invention provides new expression systems based on immortalized human blood cells and in particular based on cells of myeloid leukaemia origin. These cells surprisingly improve the production of glycosylated proteins and in particular antibodies in respect to activity, yield and/or homogeneity.

BRIEF DESCRIPTION OF THE DRAWINGS

The following tables 1 and 8

Table 1: Yield of chimaeric PankoMab expressed in CHOdhfr− and NM-F9 cultured in medium supplemented with FCS.

Table 2: Yield of chimaeric PankoMab expressed in NM-H9D8 [DSM ACC2806] cultured in serum-free medium.

Table 3: Quantification of the sialic acid content in PankoMab and CetuxiMab: The antibodies were produced by the indicated cell line and quantified by integrating the peak area obtained by reverse phase chromatography of the DMB labelled sialic acid variants. NeuGc and NeuAc were differentiated by using a sialic acid standard.

Table 4: Quantification of the differently charges structures in Panko1 and PankoMab: The 2-AB labelled N-glycans were subjected to anion exchange chromatography (Asahi-PAK-column) and the peaks corresponding to the differently charges structures were quantified by integration.

Table 5: The galactosylation degree of the antibodies Panko1 and PankoMab was determined by aminophase HPLC (Luna-NH2-column) of the 2-AB labelled glycans. The peaks were quantified by integration and underlying glycan structure was analysed by mass spectrometry.

Table 6: Quantification of the triantennary and biantennary+bisected structures in Panko1 and PankoMab The potentially bisecting GlcNAc containing fractions from the aminophase-HPLC were collected and subjected to a reverse phase chromatography (RP18-column). By this triantennary and biantennary+bisected structures can be distinguished. The fucosylation degree of the antibodies was determined by aminophase HPLC (Luna-NH2-column) of the 2-AB labelled glycans. The peaks were quantified by integration and underlying glycan structure was analysed by mass spectrometry. The fucosylated and non-fucosylated structures were determined and the integrated peak areas were quantified.

Table 7: Yield of hFSH expressed in CHOdhfr− and GT-2x cultured in medium supplemented with FCS (CHOdhfr−) or serum free medium.

Table 8: Yield of hFSH expressed in NM-H9D8 [DSM ACC2806] cultured in serum-free medium.

Table 9: Suitable glycosylation and activity combinations obtainable with the method according to the present invention.

Table 10: Obtained values of bisecGlcNAc and fucose in different cell lines.

Figure 1:
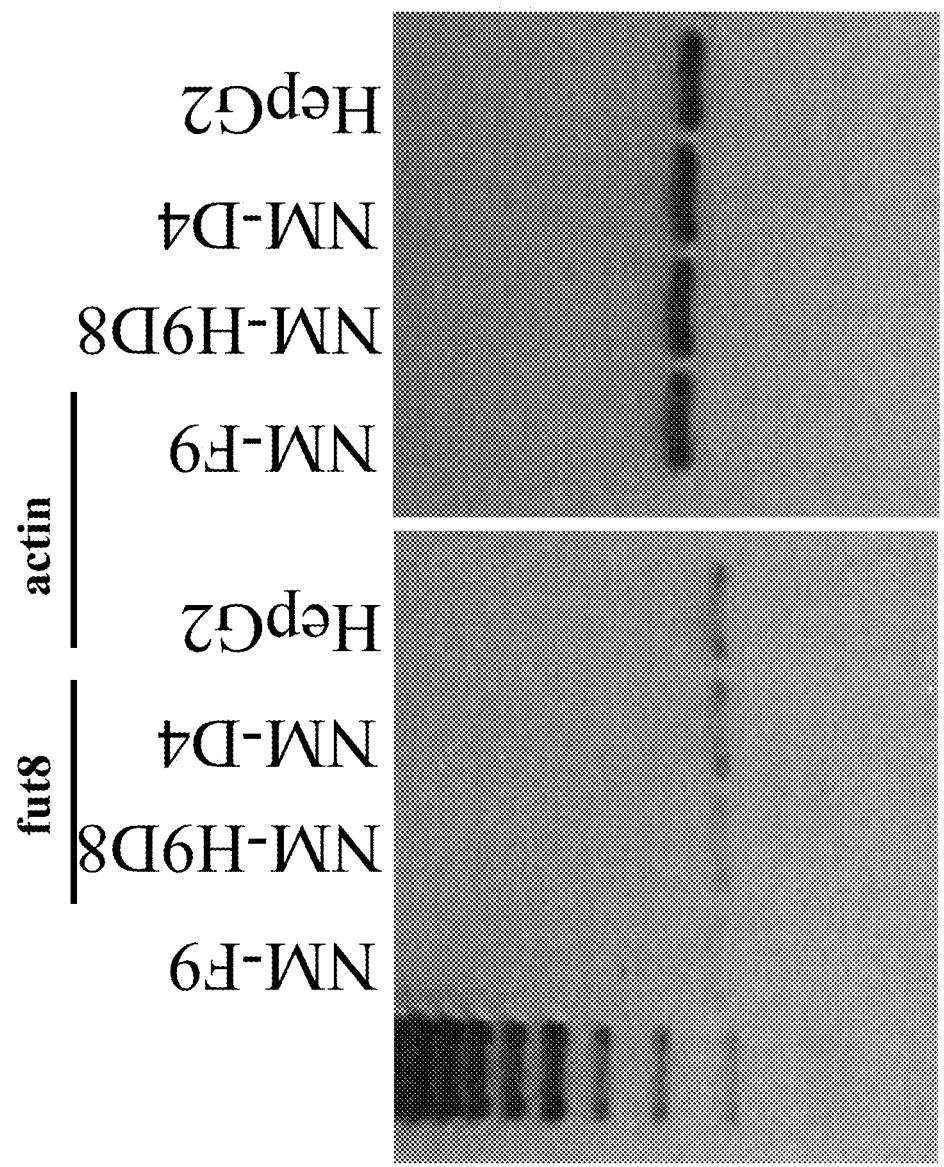
FIGS. 1 to 17 illustrate the present invention.

FIG. 1: fut8 mRNA expression of NM-F9, NM-D4, and NM-H9D8 [DSM ACC2806] cell. As a control HepG2 cells served.

Figure 2:
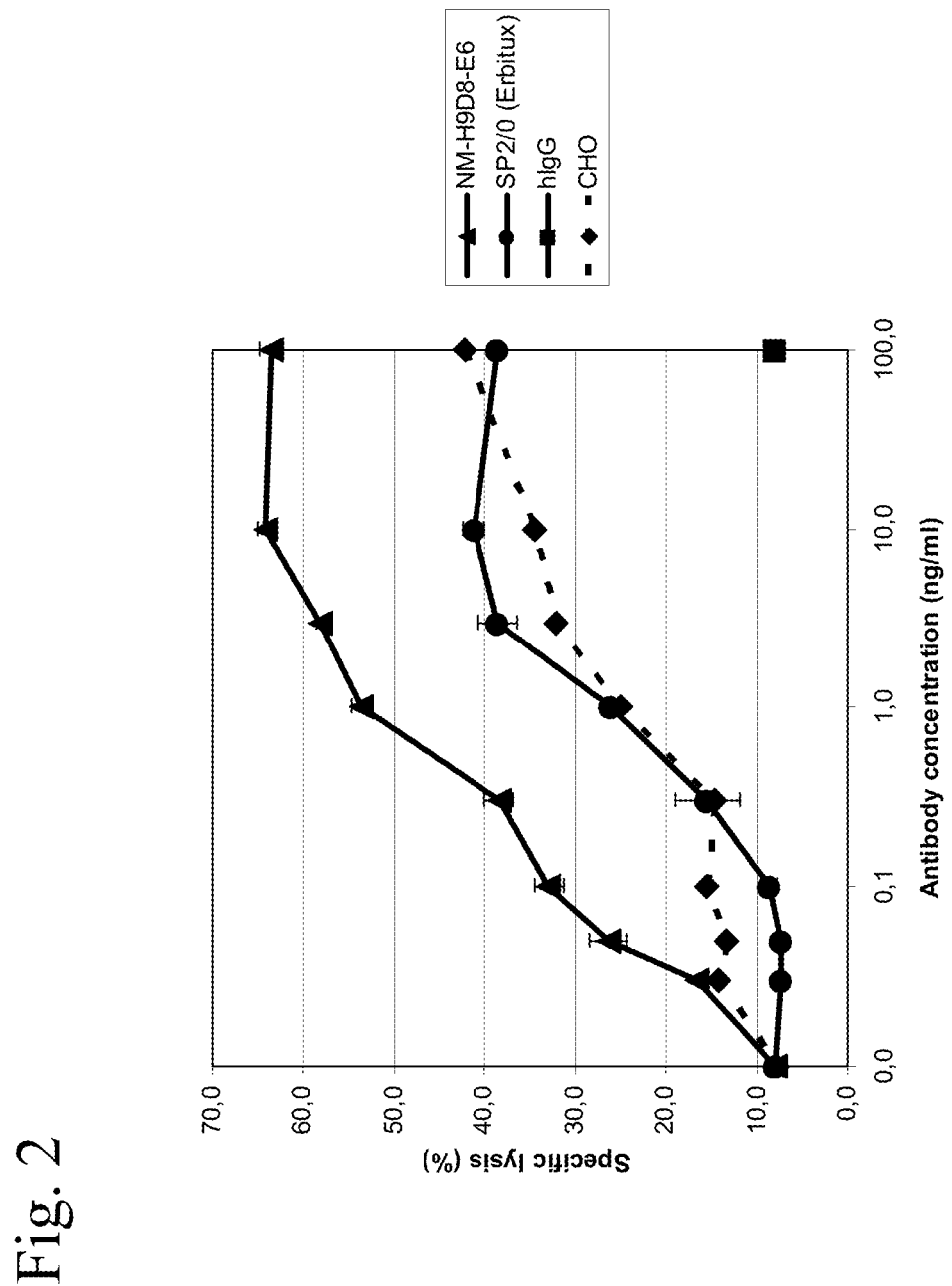

FIG. 2: Europium release assay with Cetuximab isolated from NM-H9D8-E6 cells, CHOdhfr– cells or SP2/0 cells against LS174T cells as target cells.

Assay was incubated for 4 h at an effector to target cell ratio of 50:1 with antibody concentrations from 0 to 100 ng/ml.

Figure 3:
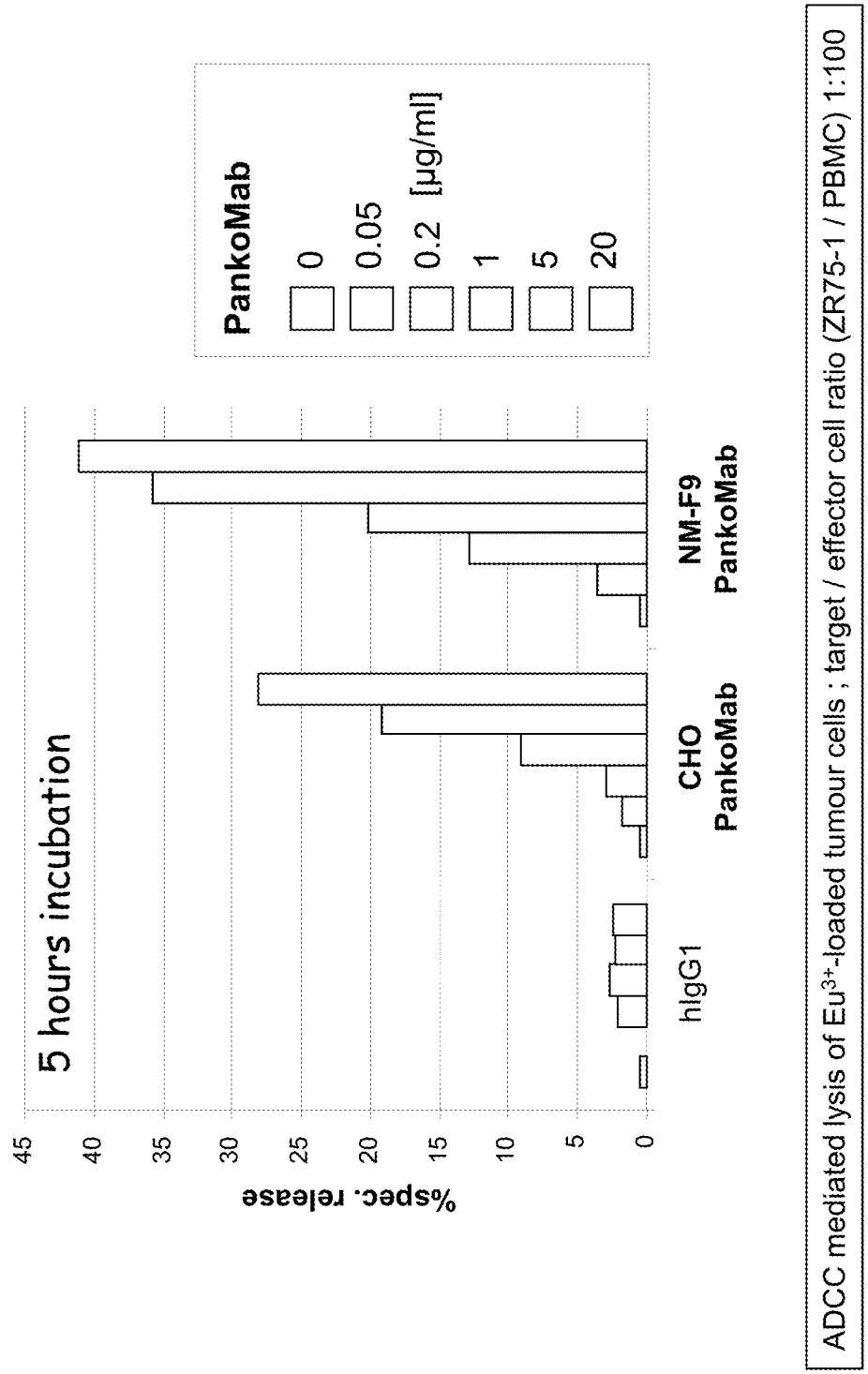

FIG. 3: ADCC activity of chimaeric PankoMab isolated from NM-F9 is ~5 times higher than chimaeric PankoMab isolated from the CHOdhfr– cells.

Figure 4:
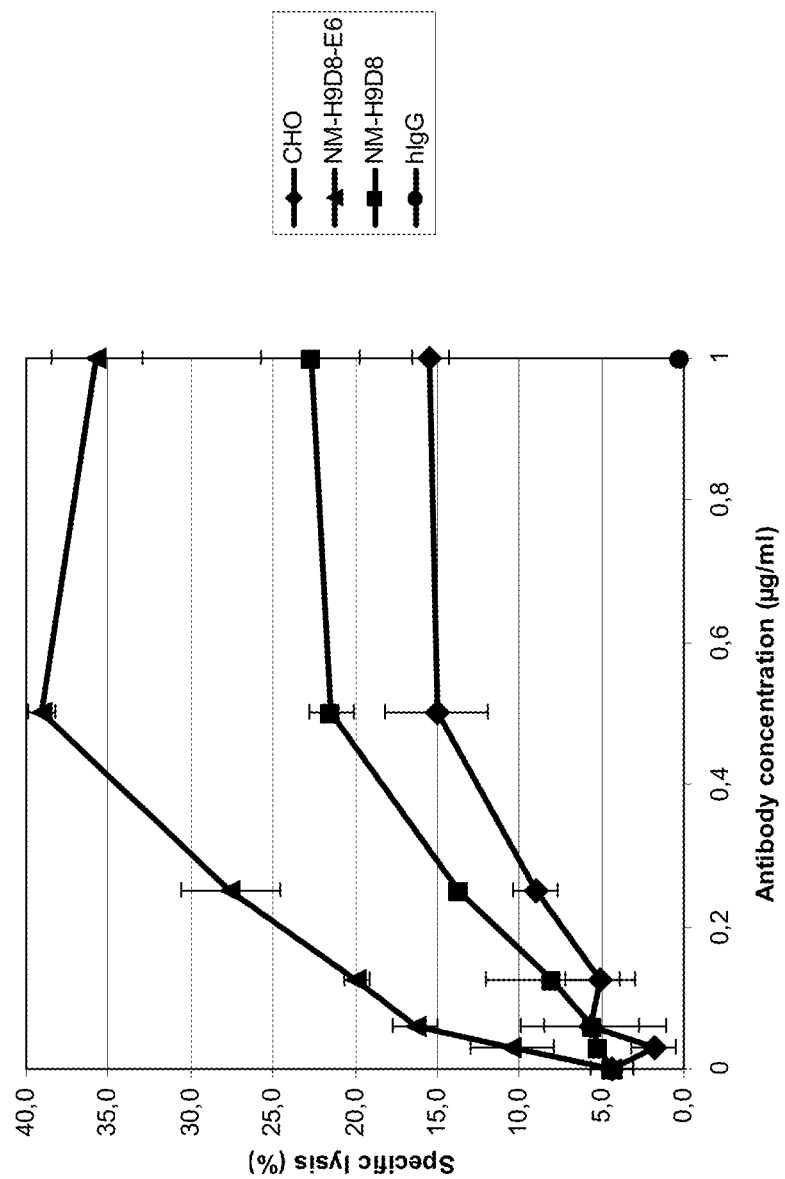

FIG. 4: Europium release assay with chimeric Panko1 isolated from NM-H9D8-E6 cells, CHOdhfr– cells and NM-H9D8 cells against ZR-75-1 cells as target cells. Assay was incubated for 4 h at an effector to target cell ratio of 80:1 with antibody concentrations from 0 to 1 µg/ml.

Figure 5:
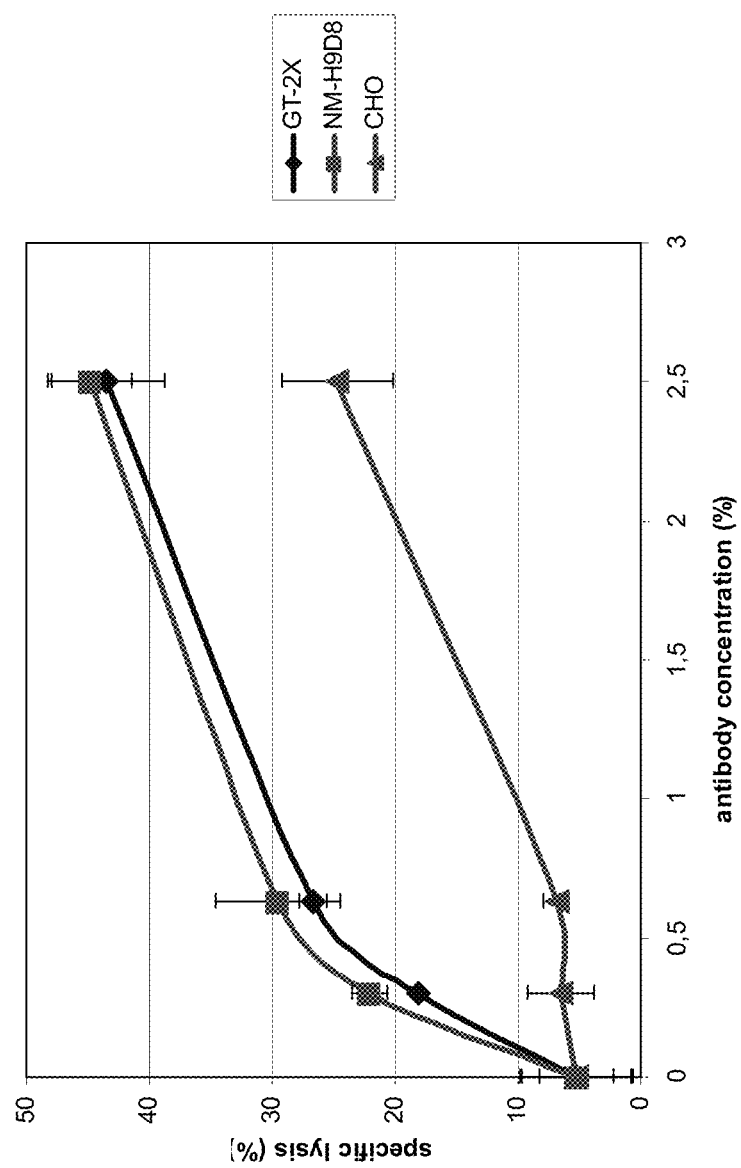

FIG. 5: ADCC activity of chimeric Panko2 in an europium release assay against ZR-75-1 cells after o.n. incubation with an effector to target cell ratio of 50:1 and 5000 target cells per well. Samples were incubated in triplicates.

Figure 6:
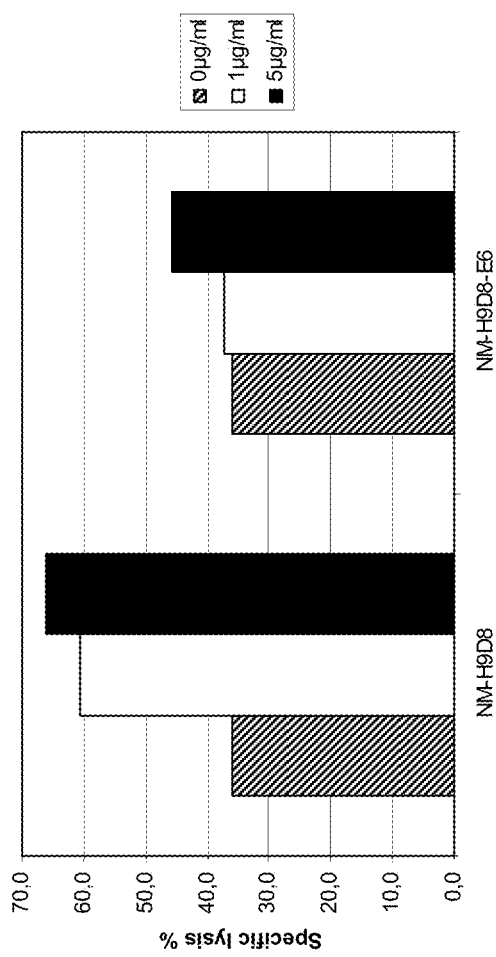

FIG. 6: ADCC activity of chimeric Panko2 in an europium release assay against ZR-75-1 cells after o.n. incubation with an effector to target cell ratio of 50:1 and 10.000 target cells per well. Samples were incubated in triplicates.

Figure 7:
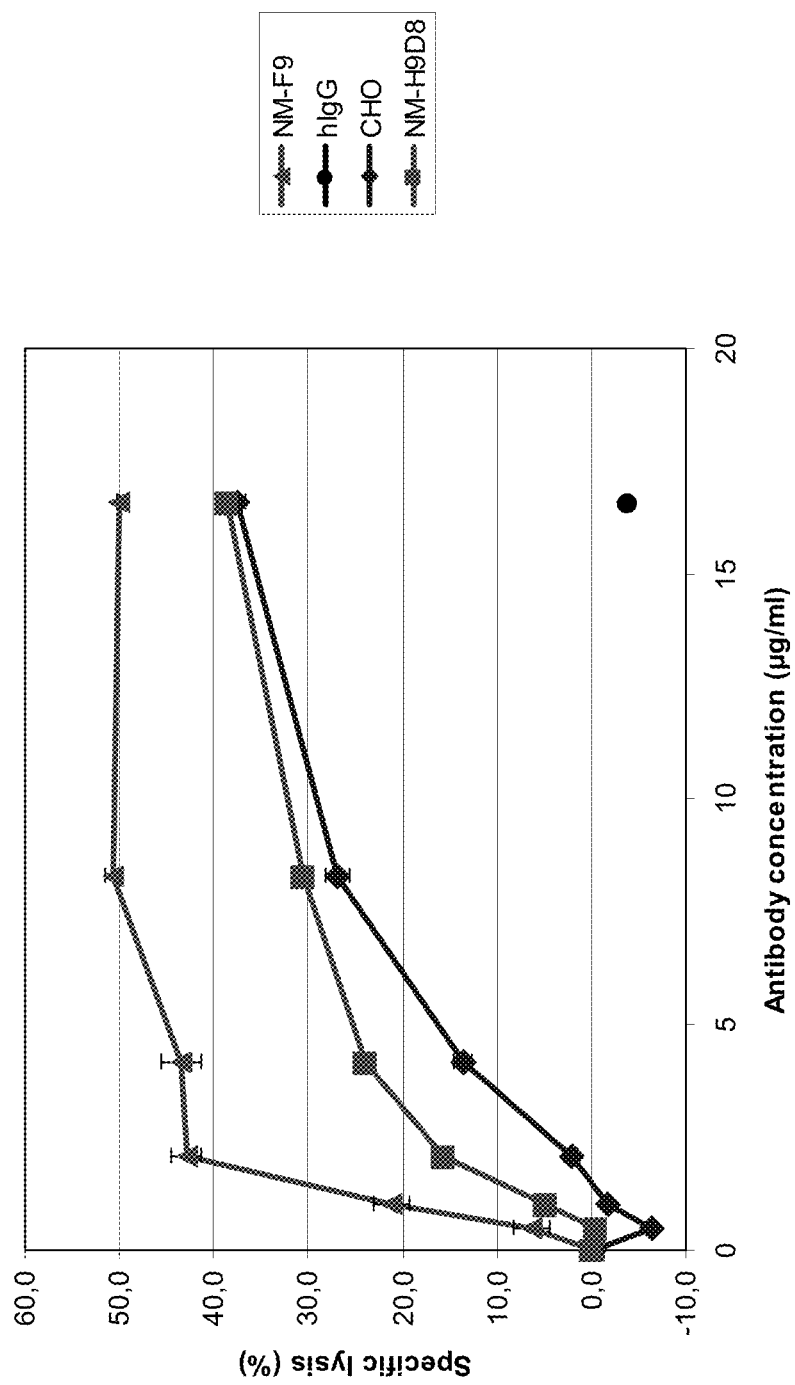

FIG. 7: CDC assay with chimeric PankoMab against ZR-75-1.

Figure 8:
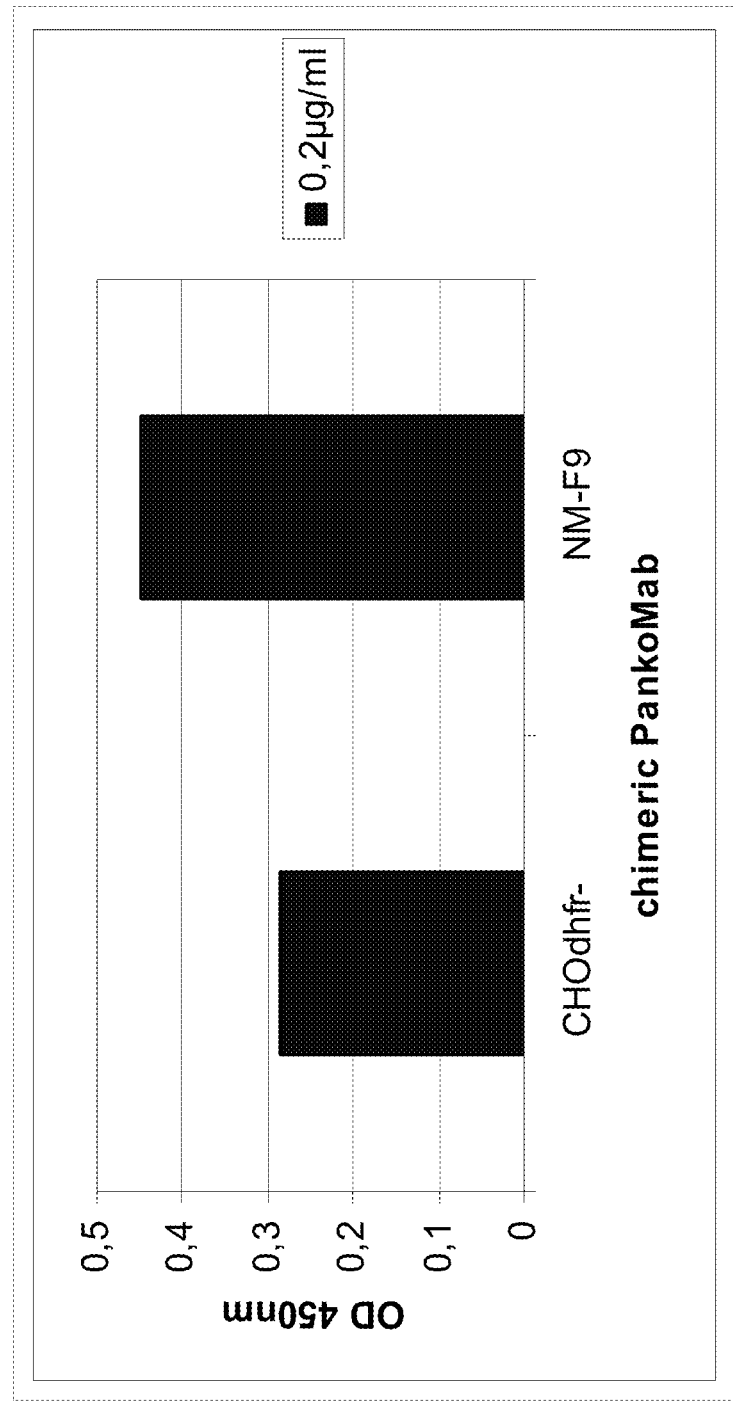

FIG. 8: Binding activity of the chimeric PankoMab isolated from NM-F9 to synthetic glycosylated MUC1 30-mer peptide is about 50% higher than the binding activity of the chimaeric PankoMab isolated from the CHOdhfr– cells.

Figure 9:
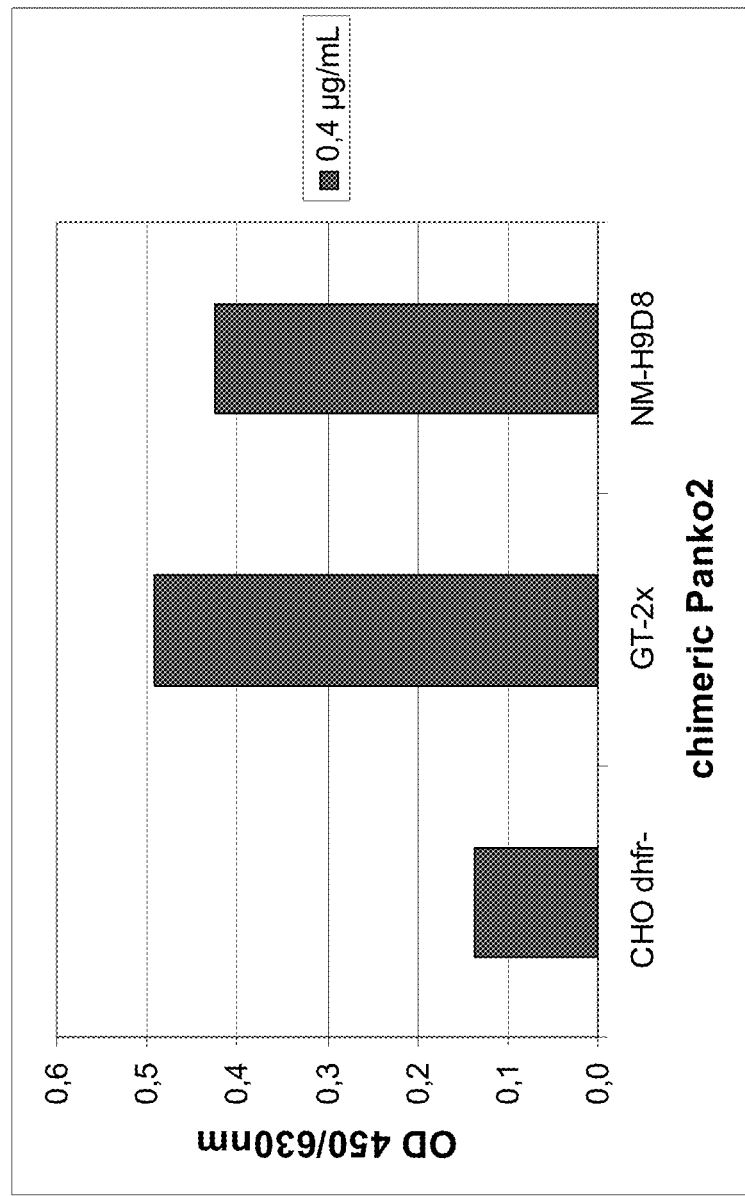

FIG. 9: Binding activity of the chimeric Panko2 isolated from GT-2x and NM-H9D8 to synthetic glycosylated MUC1 30-mer peptide is about 50% higher than the binding activity of the chimeric Panko2 isolated from the CHOdhfr– cells.

Figure 10:
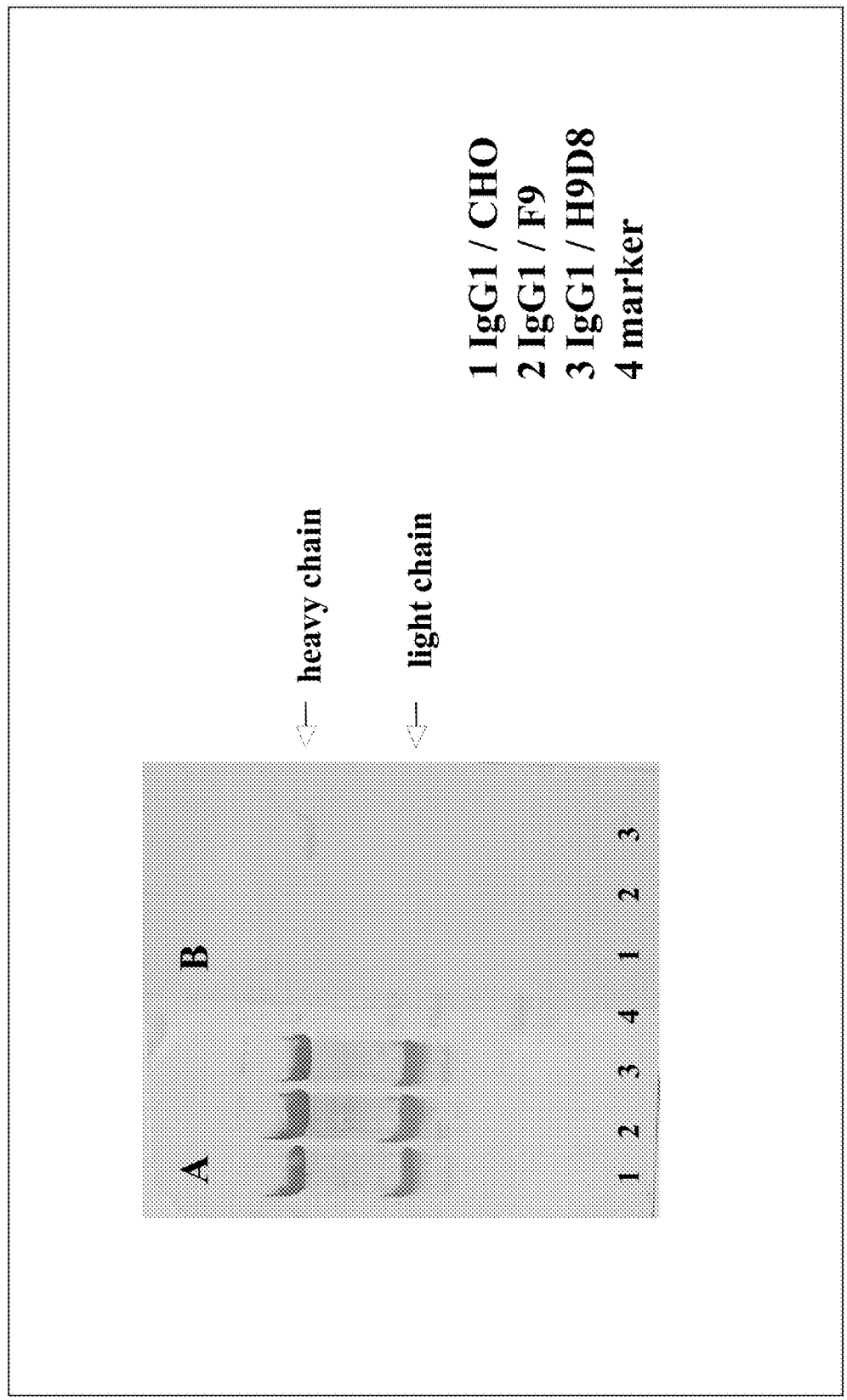

FIG. 10: Western blot analysis was performed to identify the differently sialylated heavy chain of antibody molecule compositions expressed in CHOdhfr–, NM-F9, or NM-H9D8 [DSM ACC2806]. Proteins were transferred to nitrocellulose and visualized either by secondary anti-human IgG antibodies (A) or SNA (B) which detects 2-6 sialylation.

Figure 11:
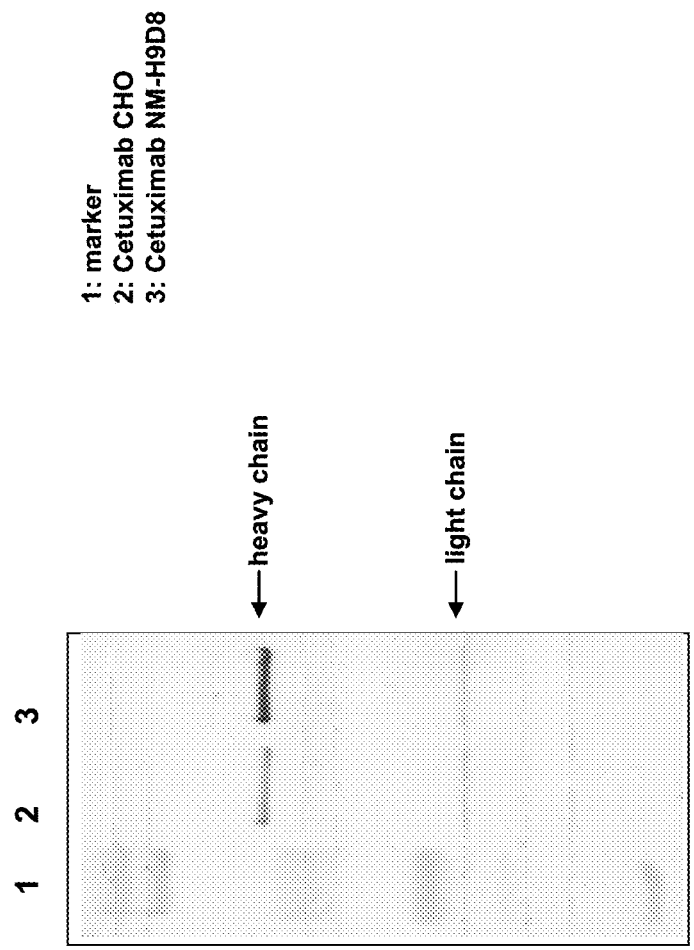

FIG. 11: Western blot analysis was performed to identify the differently sialylated heavy chain of antibody molecule compositions expressed in CHOdhfr– or NM-H9D8. Proteins were transferred to nitrocellulose and visualized by SNA which detects 2-6 sialylation.

Figure 12:
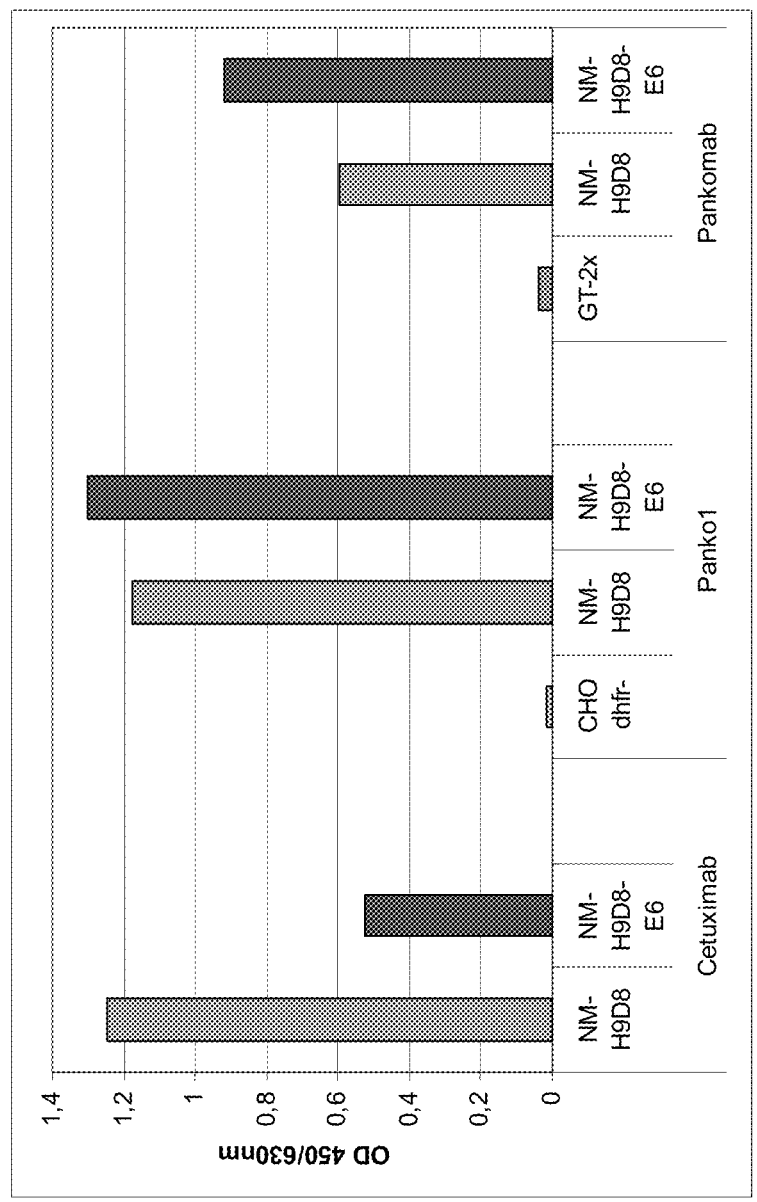

FIG. 12: ELISA analysis was performed to identify the differently sialylated antibody molecule compositions expressed in CHOdhfr–, GT-2x, NM-H9D8, or NM-H9D8-E6.

Figure 13A:
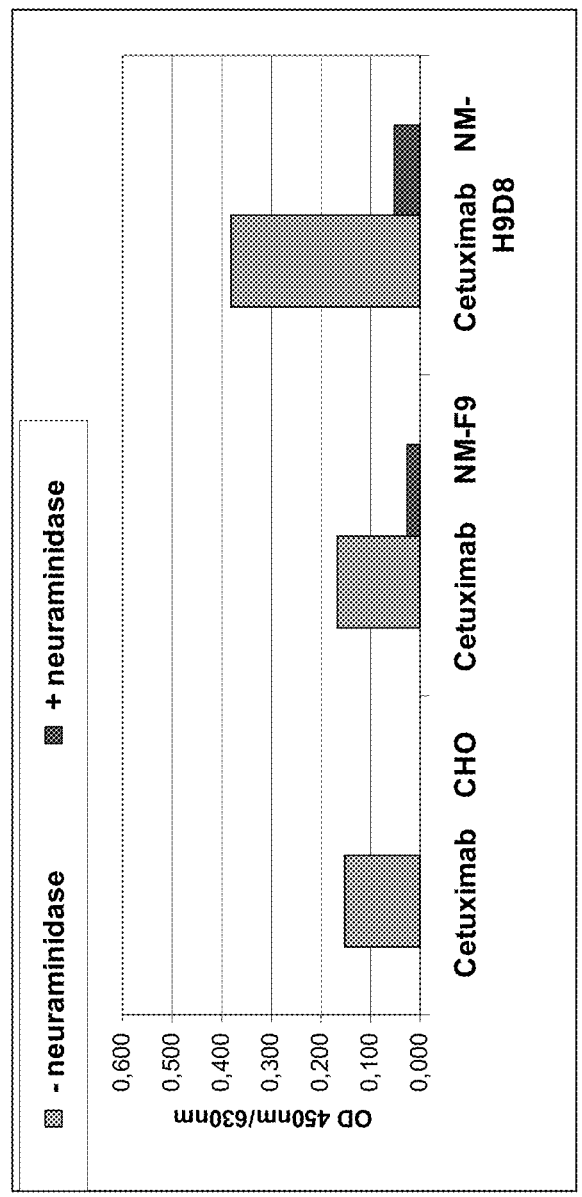
Figure 13B:
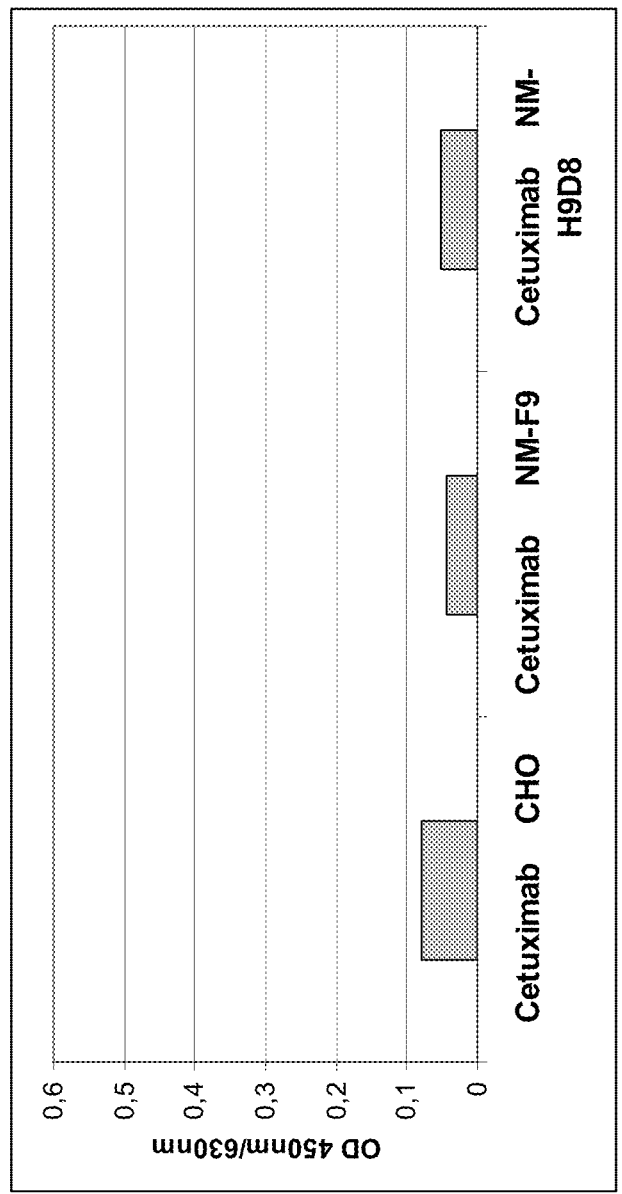

FIGS. 13A and 13B: ELISA analysis was performed to identify the differently sialylated antibody molecule compositions of Cetuximab expressed in CHOdhfr–, NM-F9, or NM-H9D8. Sialylation was analysed (FIG. 13A) by SNA which detects alpha2-6 sialylation with or without neuraminidase treatment and (FIG. 13B) by MAL I which detects alpha2-3 sialylation.

Figure 14:
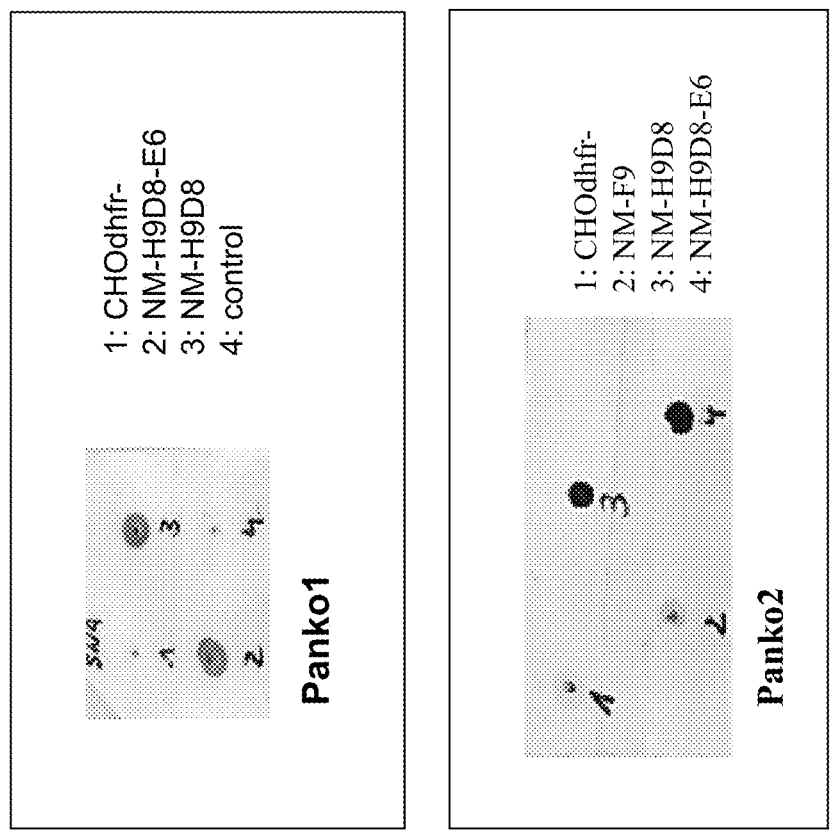

FIG. 14: Dot blots stained by SNA of the chimeric antibodies Panko1 and Panko2 isolated from CHOdhfr–, NM-F9, NM-H9D8, or NM-H9D8-E6 cells.

Figure 15:
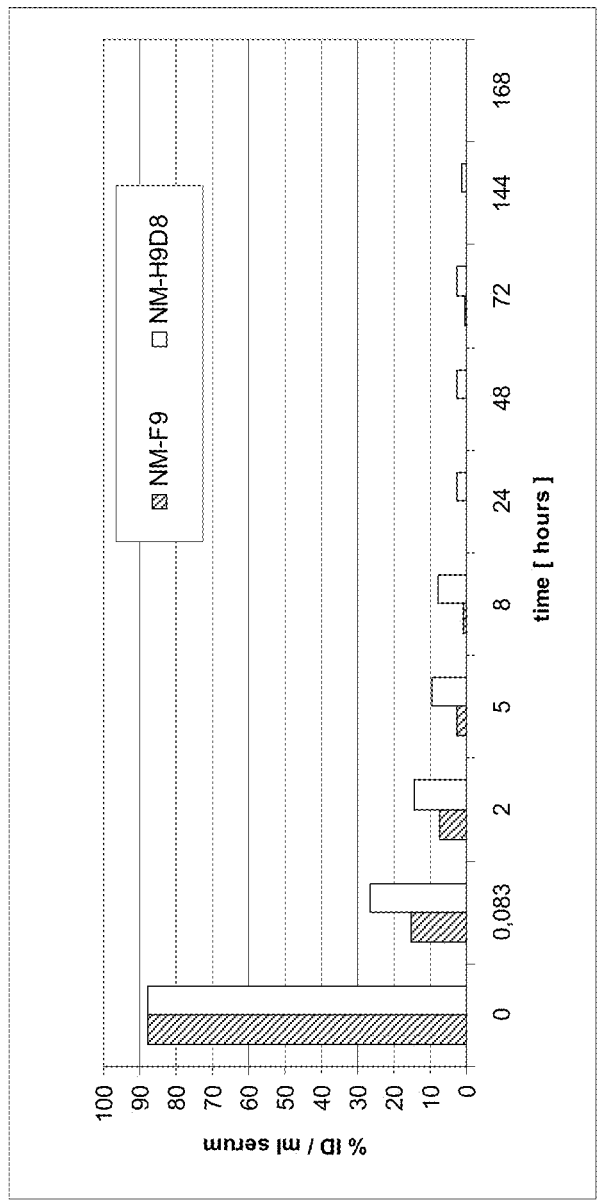

FIG. 15: The chimeric PankoMab isolated from NM-H9D8 cells is longer available in the serum of nude mice than that isolated from NM-F9.

Figure 16:
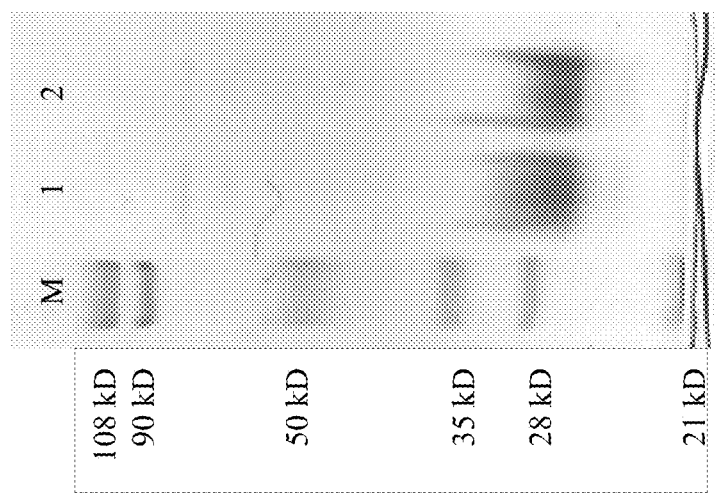

FIG. 16: SDS-Page Analysis of hFSH produced in NM-H9D8 (lane 1) and GT-2x (lane 2). 5 µg of purified hFSH was separated by SDS-PAGE under reducing conditions per lane and stained by Coomassie Brilliant Blue. The Marker indicates a range of 21-108 kD.

Figure 17:
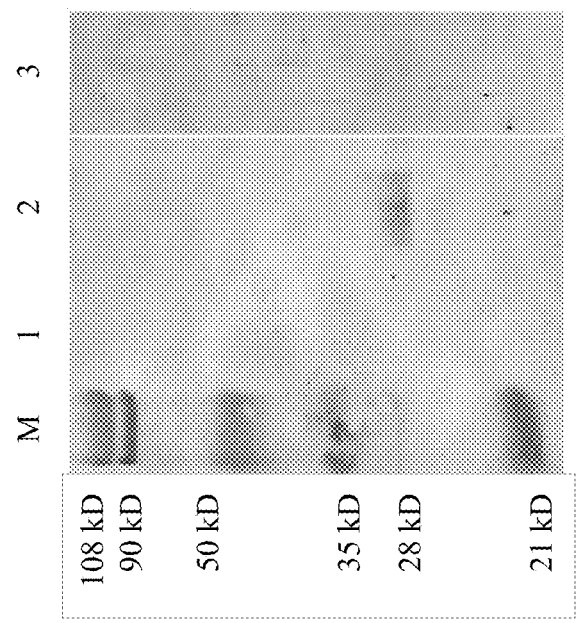

FIG. 17: Western blot analysis was performed to identify the differentially sialylated hFSH molecule compositions. 1 µg of hFSH molecule composition from CHO (lane1), NM-H9D8 (lane 2) and GT-2x (lane 3) were separated by SDS-Page in a 10% acrylamide gel under reducing conditions. Proteins were transferred to nitrocellulose and visualized SNA which detects 2-6 sialylation.

Figure 18:
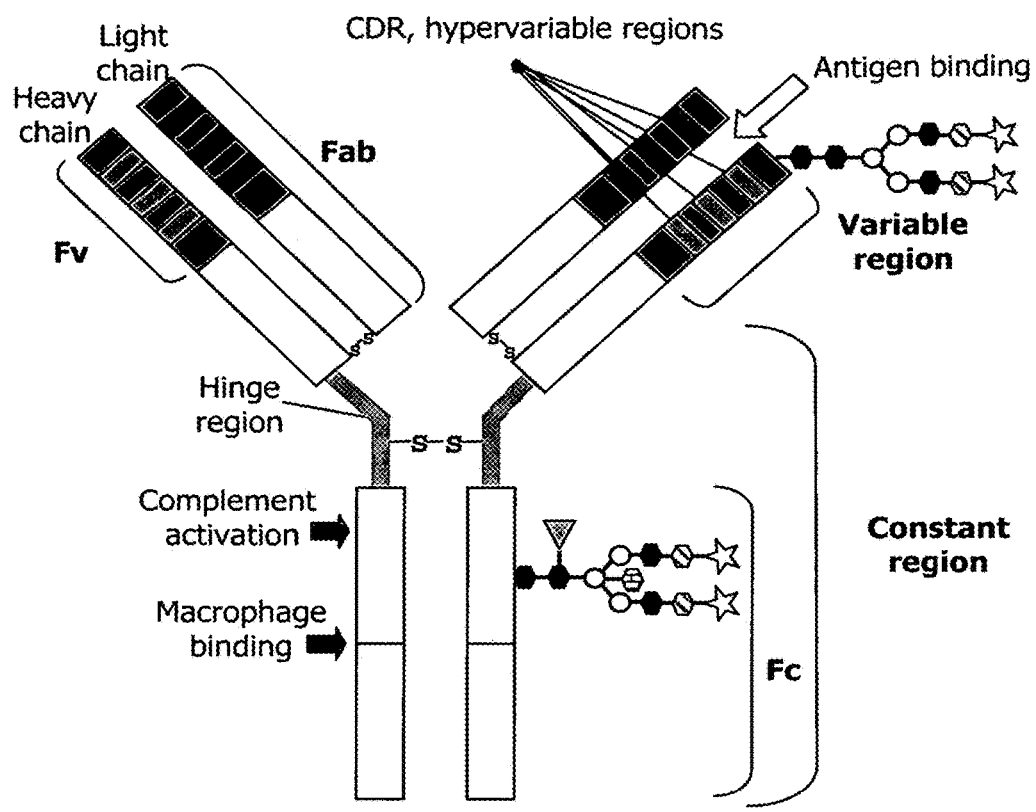

FIG. 18: Shows an IgG antibody, wherein N-glycans are covalently attached at a conserved Asn 297 residue in the $C_H2$ domain of Fc. As indicated, there may be additional N-linked oligosaccharides in the Fab domain, which can even influence the binding activity of the antibody. The glycan structures only on one half of the antibody are shown. The Fc carbohydrate is a branched chain structure which lies mainly within the two $C_H2$ domains, with one arm/antenna of each oligosaccharide interacting with the hydrophobic areas of the $C_H2$ domains. Structural analysis of polyclonal and myeloma human IgGs has demonstrated that the Fc contains various amounts of a base biantennary core structure as is demonstrated in FIG. 18. The meaning of the symbols is shown in the corresponding table. Said core structure may contain none (G0), one (G1) or two (G2) terminal galactose residues and/or a bisecting GlcNAc and/or a fucose residue at the proximal GlcNAc. Further fucose molecules may also be present at the other GlcNAc residues or the galactose residues. The diversity is even increased, as the terminal sialic acid may or may not be present depending on the properties of the antibody, as sialic acid was reported to have a negative impact on ADCC.

BACKGROUND ART

Proteins are a diverse group of which the function and occurrence vary widely among each other. Among the proteins of therapeutic potential most proteins are glycosylated, such as many hormones (e.g. Growth hormone, Glycagon, FSH and LH), growth factors (e.g. GM-CSF, G-CSF, VEGF and Erythopoietin), cytokines (e.g. IL-2, IL-7, Interferon-alpha and -beta, TNF-alpha), anti-coagulantia (e.g. Lepirudin, Desirudin), blood clotting factors (e.g. factors VII, VIII and IX), vaccines (e.g. Hepatitis B antigen) and antibodies. The established cellular production systems are unable to produce proteins with the original human glycosylation. Prokaryotic (e.g. bacteria) and most eukaryotic cell systems (e.g. yeast, insect and plant cell) synthesize proteins that lack glycosylation or carry glycans which largely differ from human carbohydrate chains. Chinese hamster ovary (CHO) cells are a commonly used production system that is able to glycosylate proteins in a similar way as human cells. However, important differences remain, such as in galactosylation, fucosylation, particular glycosylation with N-acetylglucosamines, and especially in various aspects of sialylation. These differences influence the activity, the bioavailability, the immunogenicity and the half-life.

At the time these production systems were established, it was sufficient to produce therapeutic proteins that were at least to some degree active. However, today large efforts concentrate to improve the activity of a therapeutic protein with the aim (i) to reduce the number and concentration of the applied doses of the therapeutic proteins, (ii) to reduce the costs of a therapy, and (iii) to reduce the side effects.

The major strategy to improve the bioactivity of proteins is to elongate their serum-half life and hence their bioavailability. This can be done e.g. by the process called PEGylation where certain forms of polyethyleneglycol are added/linked chemically to the produced protein. PEG increases the molecular weight and hence the serum half-life. However, several problems are associated with this process. For example, in nearly all cases PEGylation decreases the activity of a protein by its cellular effector function, repetitive administration in humans often results in an adverse immune response as neutralizing antibodies, and/or the production process needs additional chemical modification resulting in a multistep process with additional costs, losses and time. Similar carrier systems (e.g. HESylation or attachment of albumin) exist which have comparable drawbacks.

Also the modification of the carbohydrate chains and thus the glycosylation of proteins is in the focus in order to improve the serum-half life of recombinantly expressed proteins. The technologies thereby focus on the maximization of the sialylation degree of a recombinant glycoprotein. Sialic acids are the most prevalent terminal monosaccharides on the surface of eukaryotic cells and it is generally believed that the more a glycoprotein is sialylated the longer is its serum half-life during circulation. This is based on the presence of certain receptors as the asialoprotein-receptor in the liver which binds circulating non-sialylated proteins and directs them into the cell for degradation.

Various classes of antibodies are present in human and most mammalian, namely IgG, IgM, IgE, IgA, IgD. While molecules of all antibody classes are used in diagnostics or as research tools, the majority of antibody based therapeutics on the market and under development are IgG and to a lesser extend IgM. The human IgG class is further classified into four subclasses, IgG1, IgG2, IgG3 and IgG4. The basic structure of an IgG molecule consists of two light chains and two heavy chains comprising two Fab regions each with one variable domain comprising the antigen-binding site and one constant domain, one Fc region comprising further constant domains and the interaction sites for ligands, and the flexible hinge region which connects Fab and Fc regions. Antibodies can exist as whole molecules or as antibody fragments such as Fab fragments or single chain Fv which comprise the two variable regions of the heavy and light chain connected via a linker. FIG. 18. shows an IgG antibody.

Recombinant antibodies for therapeutic use are most often chimaeric, humanized or so-called fully human protein sequences in order to reduce their immunogenicity. However, truly fully human molecules has not be readily achieved since the posttranslational modifications such as particularly the glycosylation is not human due to the production in rodent or CHO cells and thus can differ from those modifications found on human antibodies in human sera. Differences in the modification, in particular the glycosylation pattern, can have a serious impact on the activity and the immunogenicity of the respectively produced antibody.

The activity of an antibody can be due to and influenced by a combination of effects. On one hand side the antibody has a certain specificity which is mediated by the variable region of the antibody ("V region") located in the Fab region wherein certain sequences, the CDR regions, of the V region. They play a key role in determining the particular specificity and affinity of an antibody. The V regions are thus decisive for the epitope binding characteristics and vary from antibody to antibody. The affinity of an antibody describes the strength and kinetics of the binding of a single binding region of an antibody to its epitope. Since the various classes and subclasses of antibodies carry between two and ten identical variable regions in one antibody molecule, the strength and kinetics of the binding of an antibody is influenced by the number of binding sites available for binding to and the accessibility of epitopes on the target antigen or cell and is expressed in its avidity.

Another important factor for the quality of an antibody for its use in diagnosis and especially in therapy is the number of binding sites of an antibody on its target structure or cell as well as its internalisation rate. These qualities influence the effects and suitability of an antibody for its use especially in therapy.

On the other hand, effector mechanisms relevant for therapeutic use of an antibody are several fold whereby some of the antibodies act via only one mechanism and others by a combination of various effector mechanisms. One strategy is to couple antibodies or antibody fragments to effector molecules which mediate a therapeutic effect, such as coupling to an immune effector molecule, for example interleukine 2 to recruit the immune system, or coupling to toxins or radioisotopes in order to kill target cells, for example for anti-tumor therapies. Radiolabelled antibodies or antibody fragments are also valuable for in vivo diagnosis.

The other strategy is to use non-labelled, so-called "naked" antibodies which can have important advantages such as lower toxicology, less complicated logistics, the use of natural immune effector arms or triggering of therapeutic effects without the need of additional effector molecules. A large number of studies have been performed to elucidate the activity mechanisms and mode of action of antibodies as well as develop antibodies using these activities. Among the most important activities and effects are antibody-dependent cell-mediated cytotoxicity activity (herein referred to as "ADCC activity"), the complement-dependent cytotoxicity activity (herein referred to as "CDC activity"), the phagocytosis mediated cytotoxicity activity (herein referred to as "phagocytosis activity"), a receptor mediated activity (herein referred to as "receptor mediated activity") which comprises a whole set of different effects and activities.

Receptor mediated activities are mainly based on the binding of the antibody to a molecule or receptor on a target cell or by the prevention of binding of certain molecules to a target cell thereby inducing or inhibiting certain effects on these cells, such as antagonistic or agonistic activity or receptor blockade of an antibody, leading for example to the induction or inhibition of apoptosis or proliferation of target cells or to the secretion or inhibition of the secretion of certain molecules in a target cell, or blocking or triggering certain other receptor mediated events such as interactions between molecules and cells or between cells. The ADCC activity, CDC activity and phagocytosis activity are cytotoxic activities which are mediated by the Fc region of the antibody (herein referred to as "Fc part mediated activities") while the receptor mediated activities, affinity, avidity and specificity of the antibody are mainly mediated via the binding region of the antibody comprised in the Fab region.

The Fc part mediated activities are mediated via immunological effector cells such as killer cells, natural killer cells and activated macrophages, or various complement components by binding to effector ligands such as Fc-gammaRI, Fc-gammaRII, Fc-gammaRIII, C1q component of complement, the neonatal Fc receptor (FcRn), etc. The human IgG1 subclass is reported to have the highest ADCC and CDC activity among human IgG class molecules. For IgM CDC activity is a dominant effector mechanism. The ADCC activity and CDC activity involves the binding of the Fc region, the constant region of the antibody, to Fc-receptors such as Fc-gammaRI, Fc-gammaRII, Fc-gammaRIII of the effector cell or complement components such as C1q. Important amino acid residues are in the hinge region and in particular in the second domain of the constant region ("Cgamma2 domain") A carbohydrate chain binding to the Cgamma2 domains is important for the activity. The carbohydrate chain is bound to the amino acid asparagine 297 (Asn-297) of Cgamma2 (N-glycoside linked carbohydrate chains). The carbohydrate chain terminus which binds to asparagine is called the reducing end and the opposite end is called a non-reducing end. The Fc region of an IgG antibody has two carbohydrate binding sites. FIG. 18 shows the structure of an IgG molecule and indicates the position, where typically carbohydrate structures can be found. Furthermore, the chemical structure and composition of these carbohydrate structures is explained.

From the Fc part mediated activities, two are assumed to be influenced by the glycosylation of the antibody: It has been shown that the removal of the sugar chain in the Fc part of the antibody results in the disappearance of the CDC and ADCC activity and also a reduction of galactoses in these N-glycans causes a decrease in CDC activity [Boyd et al., Molecular Immunol., 32, 1311, (1995); U.S. Pat. No. 6,946, 292]. Furthermore, it is described that expression of antibodies in rat cells results in an increased ADCC activity of certain antibodies expressed therein [Lifely et al., Glycobiology, 1995 December; 5(8):813-22; WO00/61739] when compared to the same antibody expressed in hamster and rat cells. Both reports assume that changes in the glycosylation cause these differences in antibody ADCC activity, however, this is not clear. Lifely et al. 1995 assumes that bisecting N-acetylglucosamine ("bisecGlcNAc") is responsible for an increased ADCC activity of the antibody, while WO00/61739 assumes that a dramatic decrease of fucose alpha1-6 linked to N-acetylglucosamine at the reducing end of N-glycans ("core-fucose") is responsible for an increased ADCC activity. Furthermore, it is described that recombinant expression of the enzyme GnTIII in CHO cells which is responsible for attaching the sugar bisecGlcNAc to N-glycans results in an increase of the ADCC activity of certain antibodies when expressed in these cells when compared to the same antibody expressed in CHO cells not recombinantly transfected with GnTIII [U.S. Pat. No. 6,602,684, Umana et al., Nature Biotechn 17: 176-180 (1999)]. Additionally, it was described that the knock-out of the gene FUT8 in CHO cells which results in the lack of core-fucose can increase the ADCC activity of certain antibodies when expressed in such FUT8 KO CHO cells [U.S. Pat. No. 6,946,292]. These results also demonstrate the importance and complexity of the glycosylation pattern for the activity of the antibody.

However, a "foreign" and thus non-optimized glycosylation pattern may not only be detrimental for the activity, it may also be immunogenic. Current expression and production systems for proteins and in particular antibodies are mainly cell lines derived from rodents and are based on cell lines from hamster, mice, or rat such as CHO, BHK, NS0, Sp2/0 and YB2/0. It is known that rodent cells can produce under non-optimal conditions a number of abnormally glycosylated protein products that lack potency or are immunogenic. In addition, rodent cells are known to express carbohydrate structures with important differences to those expressed in human cells comprising the presence of non-human sugars and the lack of certain human sugar moieties which can render proteins expressed in these cells for example immunogenic, less effective, lower yield or suboptimal structural requirements or folding. Most rodent cells express for example N-glycolylneuraminic acid ("NeuGc") an alternative for N-acetylneuraminic acid ("NeuNAc") not present in humans which is immunogenic in humans and/or the immunogenic galactose alpha(1-3) galactose modification ("Gal alpha1-3Gal"), and/or they lack important carbohydrates such as the important alpha2-6 linked NeuNAc or they lack bisecGlcNAc. There are also other known and unknown differences. In addition, it is known from rodent production that the glycoform profiles are mostly heterogeneous and also the clone-specific glycoform profile which can vary widely from clone to clone in CHO, NS0, or Sp2/0 cells and are dependent on the mode of production and culture conditions.

Furthermore, expression systems exist for the production of proteins which incorporate human cells, such as e.g. Hek 293 cells, which are derived from human embryonal kidney cells or the cell system PerC6® which is derived from a single, human retina-derived cell, which was purposely immortalized using recombinant DNA technology. However, these cell lines even though often preferred over non-human cell systems, still have some drawbacks. They have a unique glycosylation pattern which is attributable to the glycosylation machinery of the respective cells. However, depending on the protein to be produced, they might not deliver an optimised glycosylation profile e.g. regarding activity and/or serum half-life of the protein. In particular a certain degree and pattern of sialylation is difficult to achieve with these cells. E.g. the cell systems known in the state of the art are often not capable of providing a detectable alpha 2-6 linked sialylation, which, however, is important for the serum half-life.

From these facts it becomes clear that there is still a need for expression and production systems which can further optimise the productivity, homogeneity, and/or antibody activity by providing alternatives and/or improved expression systems. Furthermore, from these facts it also becomes clear that it can not be said which carbohydrate structures and especially which human carbohydrate structures are optimal to improve the activity or homogeneity of proteins and in particular antibodies and what kind of glycosylation pattern a cell line and especially a human cell line has to provide in order to optimise the activity of a protein, in particular an antibody. Therefore, there is a need for expression systems, providing products with a diverging glycosylation pattern compared to the products obtained with the expression systems known in the state of the art.

The present invention provides solutions to these problems by providing new expression systems based on human immortal blood cell lines and in particular cells of myeloid leukaemia origin. Using immortalized human blood cells is advantageous compared to the system known in the prior art because these cells provide a different glycosylation profile than other known human cell systems derived from different tissue (e.g. kidney or retina). These differences may be advantageous regarding activity, homogeneity and product yield. Furthermore, these cells can be transfected and grown in suspension under serum-free conditions.

Hence, according to a first embodiment, a method for producing a protein composition is provided, comprising the following steps:
(a) introducing in a host cells which is an immortalized human blood cell at least one nucleic acid encoding at least a part of said protein; and
(b) culturing said host cell under conditions which permit the production of said protein composition; and
(c) isolating said protein composition.

This method utilizing immortalized human blood cells improves the production of proteins and in particular antibodies in respect to activity, yield and/or homogeneity. This is surprising since so far it was not shown that immortalized human blood cells and in particular myeloid leukaemia cells are suitable for the production of proteins and particularly lead to antibodies with respectively improved properties. While a certain rat leukaemia cell was used for expression of antibodies the glycosylation machinery between human and rat are critically different whereby the latter can express carbohydrate moieties which can be immunogenic in human such as NeuGc and Gal alpha1-3 Gal. The rat YB2/0 leukaemia cell was described to yield antibodies with higher ADCC activity due to higher presence of bisecGlcNAc or due to drastic downregulation of core-fucose.

It was even more surprising that the problem could be solved by this invention using immortalized human blood cells and in particular myeloid cells since it was previously reported that the cell line K562—a myeloid leukaemia cell—does not express the enzyme for bisecGlcNAc, a finding that was described and shown by gene hybridisation of GnTIII [Yoshimura M et al., Cancer Res. 56(2): 412-8 (1996)] and does express the gene FUT8 which expresses the fucosyltransferase which causes addition of core-fucose as shown by RT-PCR [example 1]. It was surprising because K562 is not resistant to lectin treatment since it is bound strongly by the lectin LCA, the basis for cells negative or strongly down-regulated for core-fucosylation. Due to this information on the glycosylation profile of K 562 cells, it could not be expected that those cells can improve the activity of antibodies expressed therein as it was assumed that the glycosylation machinery necessary for a favourably activity pattern was not present. It was also surprising that proteins and in particular antibodies with increased binding activity, improved homogeneity and/or higher yields can be generated and achieved with the production method of the present invention compared to cells of current expression systems.

The strategy of the invention is to generate suitable human cell lines in order to achieve a system, which can provide protein products with a whole set of posttranslational modifications as near as possible to the human system and hence non- or less immunogenic properties and/or improved activity in the human system. The aim is to provide a tailor made glycosylation pattern for each protein/antibody to be expressed.

Due to the fact that carbohydrate structures are very complex, that the glycosylation machinery of cells comprise several hundred enzymes which are involved in their synthesis and that those enzymes are mainly species specific and tissue specific expressed, the major strategy of the inventors to achieve a human glycosylation is to provide suitable biotechnologically human expression systems to express proteins and in particular antibodies, with an optimised glycosylation pattern. As the optimised glycosylation pattern may differ from protein to protein and from antibody to antibody, the invention provides cell lines producing different glycosylation patterns, thereby allowing to select the cell line for production which produces a glycosylation pattern optimised for the respective protein/antibody product.

Hence, the invention provides biotechnologically favourable methods for the production of protein compositions and in particular antibody molecule compositions having increased activity and/or increased yield and/or improved homogeneity and fully human glycosylation. It further provides novel host cells, nucleic acids, and molecule compositions.

Hence, a method for producing a protein composition, preferably an antibody molecule composition, having a defined glycosylation pattern is provided, comprising the following steps:
(a) introducing in an immortalized human blood cell as host cell at least one nucleic acid encoding a protein or at least one part thereof;
(b) culturing said host cell under conditions which permits the production of said protein composition; and
(c) isolating said protein composition having the intended glycosylation characteristics.

In order to obtain a protein composition and particularly an antibody composition having improved properties according to the present invention, the host cell is selected to produce a protein/antibody composition having at least one of the following glycosylation characteristics:
(i) It comprises no detectable NeuGc.

As was outlined above, a NeuGc glycosylation may have immunogenic properties in humans. Hence, it is desirable to avoid a respective glycosylation as far as possible. A respective glycosylation is avoided by using immortalized human blood cells and in particular by using a host cell of human myeloid leukaemia origin.
(ii) It has a galactosylation degree, that is on the total carbohydrate structures or on the carbohydrate structures at one particular glycosylation site of the protein molecule of the protein molecules in said protein molecule composition increased compared to the same amount of protein molecules in at least one protein molecule composition of the same protein molecule isolated from CHOdhfr− [ATCC No. CRL-9096] when expressed therein.

The galactose residues are found mainly beta 1-4 linked to the GlcNAc residues on the antennas of the complex type N-glycan of antibodies, but also beta-1,3 linkages have been found. However, they usually occur in triantennary structures. The influence of the degree of galactosylation on the activity is in particular regarding antibodies remarkable. It has been demonstrated that depletion of galactose leads to a reduced CDC activity. Hence, it may be preferred to have a high degree of galactosylation. Galactosylation may also play an important role for other proteins.

When referring to the total carbohydrate structure of a protein molecule, all glycosylations of the protein molecule are considered. In case the carbohydrate structures at one particular glycosylation site of the protein molecule is analysed, the focus lies on a specific carbohydrate structure(s), such as e.g. the carbohydrate structure(s) attached to the Asn 297 of the Fc part of an antibody molecule (please also refer to FIG. 18). In case a respective specific structure is evaluated, the content/composition of this specific structure is determined. One could also refer to total carbohydrate units and particular carbohydrate chains for defining said characteristics (these are synonyms).
(iii) It has an amount of G2 structures on the total carbohydrate structures or on the carbohydrate structures at one particular glycosylation site of the protein molecule of the protein molecules in said protein molecule composition which is at least 5% higher compared to the same amount of protein molecules in at least one protein molecule composition of the same protein molecule isolated from CHOdhfr− [ATCC No. CRL-9096] when expressed therein.

In particular, in case an antibody is produced according to the methods of the present invention, a high amount of G2 structures is beneficial. A "G2 structure" defines a glycosylation pattern wherein galactose is found at both ends of the biantennary structure bound to the Fc region in case of an antibody (please also refer to FIG. 18). If one galactose molecule is found, it is called a G1 structure, if there is no galactose, a G0 structure. A G2 glycosylation pattern was often found to improve the CDC of antibodies. Hence, it is preferred that at least 10%, 20%, 30%, 40%, 50%, 55%, 60%, 65%, 70%, 75%, 85%, 95% or even more than 100% higher amount of G2 structures are present in the protein/antibody composition produced. Suitable cell lines achieving a respective high G2 glycosylation pattern are described herein.

As a high overall galactosylation degree is often beneficial for the CDC of antibodies, it is often preferred to obtain 60%, 65%, 70%, 75%, 80%, 85%, 90%, 95% or even more than 95% of G2 and/or G1 structures on the total carbohydrate structures or on the carbohydrate structures at one particular glycosylation site of the protein, in particular an antibody molecule.

According to a further embodiment, more than 35% (40%, 45%, 50%, 55%, 60%, 65% or more than 70%) G2 structures are present on the total carbohydrate structures or on the carbohydrate structures at one particular glycosylation site of the protein molecule of the protein molecules in said protein composition.

(iv) It has an amount of G0 structures on the total carbohydrate structures or on the carbohydrate structures at one particular glycosylation site of the protein molecule of the protein molecules in said protein molecule composition which is at least 5% lower compared to the same amount of protein molecules in at least one protein molecule composition of the same protein molecule isolated from CHOdhfr– [ATCC No. CRL-9096] when expressed therein.

As outlined above, a high degree of galactosylation is usually advantageous. Hence, the cell lines are preferably selected such that G0 structures are avoided. The amount of G0 structures is preferably lower than 10%, 15%, 20%, 25%, 30%, 35%, 40%, 50%, 55%, 60%, 65%, 70%, 75%, 80%, 85%, 90% or the amount is even lower.

According to a further embodiment, less than 22% (20%, 18%, 15%, 12%, 10%, 9%, 8%, 7%, 6%, less than 5%) G0 structures are present on the total carbohydrate structures or on the carbohydrate structures at one particular glycosylation site of the protein molecule of the protein molecules in said protein composition.

(v) It comprises no detectable terminal Galalpha1-3Gal.

As was outlined above, a Galalpha1-3Gal glycosylation may be immunogenic in humans. This glycosylation characterises a pattern, wherein a second galactose residue is linked in alpha 1,3 position to the first galactose residue, resulting in the highly immunogenic Galalpha 1-3 Gal disaccharide. By using immortalized human blood cells and in particular a host cell of human myeloid leukaemia origin, a respective disadvantageous glycosylation is avoided.

(vi) It comprises an amount of fucose on the total carbohydrate structures or on the carbohydrate structures at one particular glycosylation site of the protein molecule of the protein molecules in said protein molecule composition which is at least 5% less compared to the same amount of protein molecules in at least one protein molecule composition of the same protein molecule isolated from CHOdhfr– [ATCC No. CRL-9096] when expressed therein.

Fucose residues are found on different sites within the N-glycan tree so particularly:
- alpha 1,6 linked to the GlcNAc residue proximal to the amino acid strain;
- alpha 1,3 and alpha 1,4 linked to the antennary located GlcNAc residue;
- alpha 1,2 linked to antennary located Gal residue.

On antibody attached N-glycans the vast majority of fucose residues is found 1,6 linked to the proximal GlcNAc residue (so called "core fucose"). It has been found that the absence of core fucose on the reducing end of the N-glycan attached to antibodies enhances the ADCC activity of antibodies by the factor 25 to 100. Due to this beneficial effect on ADCC, it is preferred that the amount of fucose is at least 10%, 15%, 20%, 30%, 40%, 50%, 60%, 70%, 80%, 90%, 100%, 150%, 200%, 250%, 300%, 400%, 500%, 1000%, 1500% or more than 2000% less compared to the same amount of protein molecules in at least one protein molecule composition of the same protein molecule isolated from CHOdhfr– [ATCC No. CRL-9096] when expressed therein. The present invention also provides specially engineered cell lines which achieve a respective low overall fucosylation.

According to a further embodiment, said host cell is selected to produce a glycoprotein, comprising at least 10% (15%, 20%, 25%, 30%, 35%, 40%, 45%, 50%, 55%, 60%, 65%, 70%, 75% or more than 80%) carbohydrates of the total carbohydrate structures or of at least one particular carbohydrate structure at a particular glycosylation site of the protein molecule of said protein molecules in said protein molecule composition, which lack fucose. Regarding antibodies it is particularly preferred that the N-glycoside linked carbohydrate chains bound to the Fc region comprises a reducing end comprising GlcNAc, wherein the carbohydrate chains do not contain fucose bound to the 6 position of the GlcNAc in the reducing end of the carbohydrate chain.

(vii) It comprises at least one carbohydrate structure containing bisecting GlcNAc.

Bisecting N-Acetylglucosamine (bisGlcNAc) is often found beta 1,4 attached to the central mannose residue of the tri-mannosyl core structure of the N-glycans found in antibodies. The presence of bisecting GlcNAc at the central mannose residue of the antibody Fc-N-glycan increases the ADCC activity of antibodies.

According to a further embodiment, said host cell is selected such that said protein produced comprises more carbohydrate structures of the total carbohydrate units (or of at least one particular carbohydrate chain at a particular glycosylation site of the protein molecule) of the protein molecules in said protein molecule composition containing no fucose and no bisecting GlcNAc than those respective carbohydrate structures which contain bisecting GlcNAc and no fucose.

According to a further embodiment, said host cell is selected such that said protein produced comprises more carbohydrate structures of the total carbohydrate units (or of at least one particular carbohydrate chain at a particular glycosylation site of the protein molecule) of the protein molecules in said protein molecule composition containing more bisecting GlcNAc and fucose than those respective carbohydrate structures which contain bisecting GlcNAc and no fucose.

(viii) It has a sialylation pattern which is altered compared to the sialylation pattern of at least one protein molecule composition of the same protein molecule isolated from CHOdhfr− [ATCC No. CRL-9096] when expressed therein.

The influence of the sialylation degree/pattern on the activity, half-live and bioavailability differs between different proteins/antibodies. Hence, it is beneficial to determine for each protein/antibody molecule the optimised sialylation pattern in advance by using the screening method according to the present invention, before establishing the production with the most suitable host cell, providing the desired glycosylation pattern. E.g. several publications exist reporting a negative impact of sialic acid residues present on the Fc glycan of antibodies on downstream effects, i.e. CDC and ADCC. However, it was found that a high silaylation prolongs the half-life of the sialylated molecules. Hence, depending on the protein/antibody produced, a different sialylation pattern could be advantageous and the present invention provides immortalized human blood cell lines having different sialylation activities thereby allowing to obtain proteins/antibodies depicting an optimized glycosylation pattern.

According to one embodiment, the host cell is selected such that it produces a protein, having a decreased sialylation degree with at least a 10% (preferably 15%, 20%, 25%, 30%, 35%, 40%, 45%, 50%, 55%, 60%, 65%, 70%, 75%, 80%, 85%, 90%, >95%) lower amount of sialic acids on the total carbohydrate structures or on the carbohydrate structures at one particular glycosylation site of the protein molecule of the protein molecules in said protein molecule composition than the same amount of protein molecules in at least one protein molecule composition of the same protein molecule isolated from CHOdhfr− [ATCC No. CRL-9096] when expressed therein. According to one embodiment, the product comprises even no detectable NeuNAc. Depending on the protein/antibody produced, the presence of sialic acids and particularly NeuNAc may not contribute to the activity of the protein/antibody. In these cases, it may be favourable to avoid sialic acids glycosylation in order make the product more homogeneous. This, as the NeuNAc glycosylation pattern can also vary in the resulting protein composition. This can cause difficulties in the regulatory approval of the product because the product is due to the varying NeuNAc content less homogeneous.

For proteins/antibodies which do not rely on the presence of a NeuNAc glycosylation for their activity, an avoidance of a NeuNAc glycosylation can be beneficial in order to increase homogeneity. However, "no detectable NeuNAc" does not necessarily mean that there is absolutely no NeuNAc present. Conversely, also embodiments are encompassed, which have a rather low degree of NeuNAc (e.g. 1 to 10%).

According to one embodiment, the product has a decreased sialylation degree with a at least 15% (20%, 30%, 40%, 50%, 60%, 70%, 80%, 90%, 100%, 150%, 200%, 250%, 300%, 350%, 400%, 450%, >500%) lower amount of NeuNAc on the total carbohydrate structures or on the carbohydrate structures at one particular glycosylation site of the protein molecule of the protein molecules in said protein molecule composition than the same amount of protein molecules of at least one protein molecule composition of the same protein molecule isolated from CHOdhfr− [ATCC No. CRL-9096] when expressed therein. This embodiment is beneficial in case a protein/antibody is supposed to be expressed, wherein the sialylation has a negative effect on the activity of the protein/antibody.

A respective glycosylation (absence or very low degree of sialic acid or particularly NeuNAc) can be achieved by using sialylation deficient cells such as NM-F9 and NM-D4 in a serum-free medium.

According to a further embodiment, the product has an increased sialylation degree with an amount of NeuNAc on the total carbohydrate structures or on the carbohydrate structures at one particular glycosylation site of the protein molecule of the protein molecules in said protein molecule composition which is at least a 15% (20%, 30%, 40%, 50%, 60%, 70%, 80%, 90%, 100%, 150%, 200%, 250%, 300%, 350%, 400%, 450% or more than 500%) higher compared to the same amount of protein molecules in at least one protein molecule composition of the same protein molecule isolated from CHOdhfr− [ATCC No. CRL-9096] when expressed therein.

As was outlined above, a respectively increased degree of sialylation may provide a positive effect on the serum half-life of the protein by prolonging it. In these cases it is preferred to use a cell line which provides a higher degree of sialylation than is reached in CHOdhfr− cells [ATCC No. CRL-9096] and which also provides a higher degree of sialylation than is reached in silalylation deficient cells (such as e.g. NM-F9 and NM-D4), wherein a precursor needs to be added in order to allow sialylation to occur. However, even if a respective precursor is added when growing these sialylation deficient cells, these cells usually only reach about 50 to 60% of the sialylation degree that is obtained with immortalized human blood cells having no genetic mutation/defect in the glycosylation machinery necessary for sialylation. Hence, for embodiments, wherein a higher degree of sialylation is aimed at, it is preferred to use cell lines capable of providing a respective high sialylation degree and not to use NM-F9 and NM-D4.

According to a further embodiment, the product comprises alpha2-6 linked NeuNAc. Additionally, alpha2-3 linked NeuNAc may be present to some extent. Regarding some proteins/antibodies the presence of a NeuNAc glycosylation is beneficial in particular regarding the half-life of the protein/antibody. To provide an alpha 2-6 linked NeuNAc is beneficial, because this glycosylation pattern resembles a human glycosylation pattern. Rodent cells usually provide an alpha2-3 linked NeuNAc. Also other existing human cell lines are not capable to provide a sufficient alpha 2-6 linked NeuNAc glycosylation.

Suitable cell lines to provide a respective glycosylation pattern are e.g. NM-H9D8 and NM-H9D8-E6.

According to a further embodiment, a host cell is used, which produces a protein comprising at least 20% more charged N-glycosidically linked carbohydrate chains of the total carbohydrate units or of at least one particular carbohydrate chain at a particular glycosylation site of the protein molecule of said protein molecules in said protein molecule composition compared to the same amount of protein molecules in at least one protein molecule composition of the same protein molecule isolated from CHOdhfr− [ATCC No. CRL-9096] when expressed therein.

The charge profile of a carbohydrate chain may also influence the properties and should thus be considered. Chemical groups which charge carbohydrate chains are e.g, sulphur groups or sialic acid.

According to an alternative embodiment, said product comprises at least 20% less charged N-glycosidically linked carbohydrate chains of the total carbohydrate units or of at least one particular carbohydrate chain at a particular glycosylation site of the protein molecule of said protein molecules in said protein molecule composition compared to the same amount of protein molecules in at least one protein molecule composition of the same protein molecule isolated from CHOdhfr− [ATCC No. CRL-9096] when expressed therein.

According to a further embodiment, said host cell is selected to produce a glycoprotein, comprising at least 2% (5%, 10%, 15%, 20%, 25%, 30%, 35%, 40%, or more than 45%) carbohydrate structures of the total carbohydrate units or of at least one particular carbohydrate chain at a particular glycosylation site of the protein molecule of the protein molecules in said protein molecule composition which contain bisecting GlcNAc.

According to one embodiment, a host cell is used for the production of the protein, which depicts the following properties
- it has an increased activity, increased yield and/or improved homogeneity compared to at least one protein molecule composition of the same protein molecule when expressed in the cell line CHOdhfr− [ATCC No. CRL-9096]; and/or
- it has an increased average or maximum yield which is at least 10% higher than the yield of at least one protein molecule composition from the same protein molecule when expressed in the cell line CHOdhfr− [ATCC No. CRL-9096]; and/or
- it has an improved homogeneity, which is an improved glycosylation homogeneity wherein said antibody molecule composition has a lower sialylation degree than sialylation degree of at least one antibody molecule composition from the same antibody molecule when expressed in the cell line CHOdhfr− [ATCC No. CRL-9096]; and/or
- in case said protein molecule is an antibody molecule, it has an increased Fc-mediated cellular cytotoxicity which is at least 2 times higher than the Fc-mediated cellular cytotoxicity of at least one antibody molecule composition from the same antibody molecule when expressed in the cell line CHOdhfr− [ATCC No. CRL-9096]; and/or
- in case said protein molecule is an antibody molecule, it has an increased antigen mediated or Fc-mediated binding which is at least 50% higher than the binding of at least one antibody molecule composition from the same antibody molecule when expressed in the cell line CHOdhfr− [ATCC No. CRL-9096].

As was outlined above, the respective properties can be obtained by optimising the glycosylation of the protein as described herein. It was surprising to see that also the binding profile can be altered and improved with some antibodies based on the glycosylation profile. Suitable host cells are also described herein.

According to a further embodiment, the improved homogeneity of said protein molecule composition is an improved glycosylation homogeneity of said protein molecule composition comprising at least one of the following characteristics:
- no detectable NeuGc;
- no detectable NeuNAc;
- more NeuNAc than a protein molecule composition from the same protein molecule when expressed in the cell line CHOdhfr− [ATCC No. CRL-9096];
- detectable alpha2-6 linked NeuNAc.

According to a further embodiment, said host cell is selected to produce a protein composition comprising protein molecules having one of the following characteristic glycosylation pattern:

(a)
- it comprises no detectable NeuGc
- it comprises no detectable Galalpha1-3Gal
- it comprises a galactosylation pattern as defined in claim 2
- it has a fucose content as defined in claim 2
- it comprises bisecGlcNAc
- it comprises an increased amount of sialic acid compared to a protein composition of the same protein molecule when expressed in the cell line CHOdhfr− [ATCC No. CRL-9096] or compared to a sialylation deficient cell line such as NM-F9 and NM-D4.

(b)
- it comprises no detectable NeuGc
- it comprises no detectable Galalpha1-3Gal
- it comprises a galactosylation pattern as defined in claim 2
- it has a fucose content as defined in claim 2
- it comprises bisecGlcNAc
- it comprises an decreased amount of sialic acid compared to a protein composition of the same protein molecule when expressed in the cell line CHOdhfr− [ATCC No. CRL-9096].

(c)
- it comprises no detectable NeuGc
- it comprises no detectable Galalpha1-3Gal
- it comprises a galactosylation pattern as defined in claim 2
- it has a fucose content as defined in claim 2
- it comprises bisecGlcNAc
- it comprises 2-6 NeuNAc.

Further suitable characteristic combinations leading to improved characteristics are described in Table 9.

According to the present invention the term "protein molecule" means protein of interest or active fragments and/or mutants thereof whereby any protein can be used, preferably any glycoprotein of human origin. The term protein molecule means any polypeptide molecule or a part thereof. It can be encoded by one or several nucleic acids. It can be produced in a secretory fashion or a fraction thereof or a fusion protein with a fusion partner. Preferably, the protein is secreted into the supernatant. This embodiment is in particular beneficial regarding the overall production process, as e.g. shedding steps (e.g. with phorbol esters) can be avoided.

Examples of mammalian glycoproteins include molecules such as cytokines and their receptors, for instance the tumor necrosis factors TNF-alpha and TNF-beta; renin; human growth hormone and bovine growth hormone; growth hormone releasing factor; parathyroid hormone; thyroid stimulating hormone; lipoproteins; alpha-1-antitrypsin; insulin A-chain and B-chain; gonadotrophins, e.g. follicle stimulating hormone (FSH), luteinizing hormone (LH), thyrotrophin, and human chorionic gonadotrophin (hCG); calcitonin; glucagon; clotting factors such as factor VIIIC, factor IX, factor VII, tissue factor and von Willebrands factor; anti-clotting factors such as protein C; atrial natriuretic factor; lung surfactant; plasminogen activators, such as urokinase, human urine and tissue-type plasminogen activator; bombesin; thrombin; hemopoietic growth factor; enkephalinase; human macrophage inflammatory protein; a serum albumin such as human serum albumin; mullerian-inhibiting substance; relaxin A-chain and B-chain; prorelaxin; mouse gonadotropin-associated peptide; vascular endothelial growth factor; receptors for hormones or growth factors; integrin; protein A and D; rheumatoid factors; neurotrophic factors such as bone-derived neurotrophic factor, neurotrophin-3, -4, -5, -6 and nerve growth factor-beta;

platelet-derived growth factor; fibroblast growth factors; epidermal growth factor; transforming growth factor such as TGF-alpha and TGF-beta; insulin-like growth factor-I and -II; insulin-like growth factor binding proteins; CD proteins such as CD-3, CD-4, CD-8 and CD-19; erythropoietin (EPO); osteoinductive factors; immunotoxins; a bone morphogenetic protein; an interferon such as interferon-alpha, -beta, and -gamma; colony stimulating factors (CSF's), e.g. M-CSF, GM-CSF and G-CSF; interleukins (IL's), e.g. IL-1 to IL-12; superoxide dismutase; T-cell receptors; surface membrane proteins; decay accelerating factor; antibodies and immunoadhesins; Glycophorin A; MUC1.

Many of the aforementioned glycoproteins belong to the cytokines herein referring to the general class of hormones occurring in cells of the immune system, both lymphokines and monokines, and others. The definition is meant to include, but is not limited to, those hormones that act locally and do not circulate in the blood, and which, when used in accord with the present invention, will result in an alteration of an individual's immune response. Examples of further suitable immunomodulatory cytokines include, but is not limited to, interferons (e.g. IFN-alpha, IFN-beta and IFN-gamma), interleukins (e.g. IL-1, IL-2, IL-3, IL-4, IL-5, IL-6, IL-7, IL-8, IL-9, IL-10 and IL-12), tumor necrosis factors (e.g. TNF-alpha and TNF-beta), erythropoietin (EPO), FLT-3 ligand, macrophage colony stimulating factor (M-CSF), granulocyte colony stimulating factor (G-CSF), granulocyte-macrophage colony stimulating factor (GM-CSF), CD2 and ICAM. Taking erythropoietin, the molecule is believed to cause progenitor cells to mature into erythrocytes whereas thrombopoietin is thought to drive progenitor cells along the thrombocytic pathway. CSF refers to a family of lymphoicines which induce progenitor cells found in the bone marrow to differentiate into specific types of mature blood cells. The particular type of mature blood cell that results from a progenitor cell depends upon the type of CSF present. Similarly, granulocyte-macrophage colony formation is dependent on the presence of GM-CSF. Additionally, cytokines of other mammals with substantial homology to the human forms of IL-2, GM-CSF, TNF-alpha and others, will be useful in the invention when demonstrated to exhibit similar activity on the immune system. Adhesion or accessory molecules or combinations thereof may be employed alone or in combination with the cytokines.

Similarly, proteins that are substantially analogous to any particular protein, but have relatively minor changes of protein sequence, will also find use in the present invention. It is well known that some small alterations in the amino acid sequence in protein sequence may often be possible without disturbing the functional abilities of the protein molecule, and thus proteins can be made that function as the parental protein in the present invention but differ slightly from current known sequences. Respective variants maintaining the biological function are thus also comprised.

Preferred glycoproteins are selected from the group comprising Glycophorin A, EPO, G-CSF, GM-CSF, FSH, hCG, LH, interferons, interleukins, antibodies and/or fragments thereof.

All protein molecules mentioned above can be fused to other peptide or polypeptide sequences such as but not limited to linker, activating molecules or toxins.

In a preferred embodiment of the invention the nucleic acid encodes a secretory form of the protein or a fragment hereof. In a preferred embodiment the secretory form lacks transmembrane domains.

In accordance with the present invention the term "protein molecule composition" means the molecules of any protein molecule expressed according to the methods of the present invention and in particular in a host cell of the invention which can be isolated. Said protein molecule composition comprises at least one protein molecule. Said protein composition comprises at least one glycoform of a protein molecule. Said glycoform of a protein molecule means a protein molecule which carries a particular glycosylation or carbohydrate chain which is different in at least one sugar building block, for example but not limited to an additional galactose, sialic acid, bisecGlcNAc, fucose, or another sugar modification such as but not limited to acetylation or sulfatation from another glycoform of the same protein molecule. In another embodiment of the invention the protein molecule composition can comprise molecules of more than one protein molecule expressed in a host cell. In a preferred embodiment the protein molecule composition of the invention comprises more molecules in percent of such glycoform or such glycoforms of the protein molecule which mediate a higher activity than a protein molecule composition of the same protein molecule obtained from at least one of the cell lines CHO, or CHOdhfr–, or BHK, or NS0, or SP2/0, or PerC.6 or mouse hybridoma, preferably CHOdhfr– [ATCC No. CRL-9096], when expressed therein. In a further preferred embodiment the protein molecule composition of the invention comprises more molecules of such glycoform or glycoforms of the protein molecule in percent which mediate a higher activity than the protein molecule composition of the same protein molecule obtained from the cell lines CHO, or CHOdhfr–, or BHK, or NS0, or SP2/0, or PerC.6 or mouse hybridoma, preferably CHOdhfr– [ATCC No. CRL-9096], when expressed therein.

In accordance with the present invention the term "antibody molecule" means any whole antibody or antibody fragment or a molecule comprising an antibody fragment. Said whole antibody can be any antibody or immunoglobulin molecule of any class or subclass or any molecule comprising at least one immunoglobulin domain known to those skilled in the art comprising but not limited to IgG, IgG1, IgG2, IgG3, IgG4, IgM, IgA, IgD of animal origin such as but not limited to human, simian, rodent, mouse, rat, hamster, rabbit, camel, avian, chicken, or shark origin, and can also be a molecule which comprises protein sequences from antibodies originating from various animals such as chimaeric or humanized antibodies where various percentages of for example murine and human sequences are combined to whole antibodies and/or are mutated for example to decrease immunogenicity or increase affinity as known to those skilled in the art. In another embodiment of the invention said whole antibody can also be the afore described whole antibody with at least one additional amino acid or polypeptide sequence.

In a preferred embodiment said whole antibody is a human, humanized or chimaeric IgG, IgG1, IgG2, IgG3, IgG4, or IgM which comprises a human Fc region. In an even further preferred embodiment of the invention said whole antibody is a human, humanized or chimaeric IgG1, IgG4, or IgM with a human Fc region. Said human Fc region comprises at least one 20 amino acid sequence, more preferably at least 100 amino acids of a constant domain of the Fc region of a human antibody, preferably it comprises at least one Fc domain of a human antibody, more preferably it comprises the human Cgamma2 domain, and more preferably it comprises all constant domains of the Fc region of a human antibody of a certain class or subclass. Said human Fc region can also comprise human sequences from which at least one amino acid was mutated.

In the most preferred embodiment of the invention the whole antibody molecule is either a (i) fully human antibody generated for example from a human antibody producing blood cell or cells or from a transgenic mouse in which the mouse antibody gene locus is at least partially exchanged by human antibody sequences, or (ii) a humanized whole antibody in which at least parts of the variable regions of a murine or rat antibody, such as the framework regions or at least one amino acid of a framework, were exchanged to human sequences or mutated to be less immunogenic in humans which comprise human constant domains, or (iii) a chimaeric whole antibody in which the variable region is murine or rat and comprises human constant domains.

Said fully human antibodies, humanized whole antibodies, and chimaeric whole antibodies or parts thereof as well as the methods to construct, identify, test, optimise, and select these antibody molecules with or without suitable additional sequences as well as methods to construct, identify, test and select most suitable nucleic acids encoding these antibody molecules are known to those skilled in the art.

Said antibody fragment is any fragment of an antibody comprising at least 20 amino acids from said whole antibody, preferably at least 100 amino acids. In a preferred embodiment the antibody fragment comprises the binding region of the antibody such as a Fab, a F(ab)2, multibodies comprising multiple binding domains such as diabodies, triabodies or tetrabodies, single domain antibody or affibodies. In another preferred embodiment the antibody fragment comprises the Fc region with all or parts of its constant domains, preferably comprising the second domain (Cgamma2 domain). In another embodiment the antibody fragment is a truncated whole antibody where at least one amino acid, polypeptide stretches or whole domains are deleted. Those molecules can be combined with additional sequences for stabilization or for improving the binding of the molecules such as linkers.

Said molecule comprising an antibody fragment is any molecule which comprises any of said antibody fragments or other immunoglobulin domains of at least 20 amino acids. In a preferred embodiment said molecule comprising an antibody fragment are fusion molecules where an antibody fragment is fused to other protein sequences such as effector sequences, for example cytokines, co-stimulatory factors, toxins, or antibody fragments from other antibodies in order to generate molecules with multiple binding specificities such as bi- or tri-specific antibodies, or multimerisation sequences such as MBP (mannan binding protein) domains for resulting in the multimerisation of binding domains, or sequences for detection, purification, secretion or stabilization such as tags, localization signals or linkers, or the like. In another preferred embodiment said molecule comprising an antibody fragment are fusion molecules comprising the Fc region of a whole antibody or parts thereof, preferably comprising the second constant domain (Cgamma2 domain). Said fusion molecules are fused by genetic means, where the molecules are encoded by one nucleic acid or are fused by co-expression of at least two nucleic acids whereby the fusion is caused by non-covalent or covalent protein interactions or are fused by a combination of both. The genetic fusion between an antibody fragment and another polypeptide sequence or protein molecule can be achieved by genetic engineering where both parts are encoded by a single nucleic acid with or without additional amino acids in between. In a further preferred embodiment said fusion molecules comprise at least one binding region from an antibody fragment such as a single domain antibody, or Fab or a binding sequence not derived from antibodies, such as a lectin domain, and a Fc region or parts thereof comprising the second domain (Cgamma domain). In another preferred embodiment, the fusion molecules comprise IL-2, IL-12, IL-15, GM-CSF, a peptide toxin, or parts thereof. They are e.g. fused by genetic means, where the molecules are encoded by one nucleic acid or are fused by co-expression of at least two nucleic acids whereby the fusion is caused by non-covalent or covalent protein interactions or are fused by a comion from an antibody fragment such as a single domain antibody, Fab or Fab which is linked to multimerisation sequence of MBP.

All those antibody molecules or parts thereof as well as the methods to construct, identify, test and select these antibody molecules with or without suitable additional sequences as well as methods to construct, identify, test and select most suitable nucleic acids encoding these antibody molecules are known to those skilled in the art.

In accordance with the present invention the term "antibody molecule composition" means the molecules of any antibody molecule expressed in a host cell of the invention which can be isolated. Said antibody molecule composition comprises at least one antibody molecule. Said antibody composition comprises at least one glycoform of an antibody molecule. Said glycoform of an antibody molecule means an antibody molecule which carries a particular glycosylation or carbohydrate chain which is different in at least one sugar building block, for example but not limited to an additional galactose, sialic acid, bisecGlcNAc, fucose, or another sugar modification such as but not limited to acetylation or sulfatation from another glycoform of the same antibody molecule. In another embodiment of the invention the antibody molecule composition can comprise molecules of more than one antibody molecule expressed in a host cell. In a preferred embodiment the antibody molecule composition of the invention comprises more molecules in percent of such glycoform or such glycoforms of the antibody molecule which mediate a higher Fc-mediated cellular cytotoxicity and/or an improved binding than an antibody molecule composition of the same antibody molecule obtained from at least one of the cell lines CHO, or CHOdhfr–, or BHK, or NS0, or SP2/0, or PerC.6 or mouse hybridoma, preferably CHOdhfr–[ATCC No. CRL-9096], when expressed therein. In a further preferred embodiment the antibody molecule composition of the invention comprises more molecules of such glycoform or glycoforms of the antibody molecule in percent which mediate a higher Fc-mediated cellular cytotoxicity and/or an improved binding than the antibody molecule composition of the same antibody molecule obtained from the cell lines CHO, or CHOdhfr–, or BHK, or NS0, or SP2/0, or PerC.6 or mouse hybridoma, preferably CHOdhfr– [ATCC No. CRL-9096], when expressed therein.

In accordance with the present invention the term "host cell of human myeloid leukaemia origin" or equivalent formulations means any cell or cell line of human myeloid leukaemia origin, or any human myeloid or myeloid precursor cell or cell line which can be obtained from a leukaemia patient, or any myeloid or myeloid precursor cell or cell line which can be obtained from a human donor, or a cell or cell line derived from anyone of said host cells, or a mixture of cells or cell lines comprising at least one of those aforementioned cells.

In another embodiment of the invention said host cell of human myeloid leukaemia origin or said immortalized human blood cell of the invention also comprise such cells or cell lines which were obtained by fusing at least one of aforementioned host cells in particular those of myeloid leukaemia origin with another cell of human or animal origin, such as but not limited to B cells, CHO cells. Those skilled in the art are able to identify and use suitable sources and methods to obtain, generate and/or immortalize suitable cells and cell lines from humans for suitable host cells of human myeloid leukaemia origin.

The term cell or cell line derived from said host cell means any cell or cell line which can be obtained by any means of cultivation and cloning with or without prior mutation or genetic engineering of said host cell of myeloid leukaemia origin and comprises selection of those cells or cell lines derived from said host cell with the desired properties. Said cultivation and cloning is based on the fact that cell clones with differing properties can be obtained from primary cell cultures, cultures of cells and even cultures of cell clones by multiple rounds of passaging and cloning of the cells using preferably single cell cloning methods such as limited dilution or flowcytometry based cell sorting. In a preferred embodiment said cell or cell line derived from said host cells is selected by binding to a lectin or carbohydrate-binding antibody. Said mutation can be performed by treatment known to those skilled in the art with physical, chemical or biological mutagens, such as but not limited to radiation, alkylating agents or EMS (ethylmethanesulfonate), proteins such as lectins, or virus particles. Said genetic engineering can be performed by methods known to those skilled in the art such as knock-out of genes via site specific homologous recombination, use of transposons, site-specific mutagenesis, transfection of certain nucleic acids, or silencing of genes, or gene products. Methods for said cultivation and cloning, said mutation and mutagens and said genetic engineering are known to those skilled in the art and some examples are described in detail in WO2005/017130 A2, US 2003/0115614 A1, or are described herein. Those skilled in the art are able to select and/or adopt and/or modify a suitable method or combination of methods for generation of a suitable cell or cell line derived from said host cell of the invention.

Said cell or cell lines derived from said host cell are selected due to properties of those cells which are advantageous when compared to their parent cell or cell line such as but not limited to shorter doubling times, faster growth, possibility to grow under higher densities, can produce more, are growing under serum free conditions and/or in protein free media, higher cloning efficiencies, higher transfection efficiencies for DNA, higher expression rates of antibody molecule compositions, higher activities for an antibody molecule composition expressed therein, higher homogeneities of an antibody molecule composition expressed herein, and/or higher robustness to scaling up. Methods for selecting those cells with advantageous properties are known to those skilled in the art or described herein. The invention provides a method for generating a host cell of the invention, comprising (a) incubating a human myeloid leukaemia cell with a lectin or an antibody recognizing a desialylated epitope or an epitope lacking a sialic acid but which binds not or significantly less the sialylated form of the epitope, and (b) isolating cells bound to said lectin or antibody, and (c) culturing the isolated cells for a suitable time, and (d) select a cell, cells or a cell clone which strongly binds to a lectin or an antibody which binds to an epitope with sialic acid.

More preferred is the method as described above, wherein said lectin or said antibody recognizing a desialylated epitope or an epitope lacking a sialic acid is Nemod-TF1, Nemod-TF2, A78-G/A7, or PNA and wherein said human myeloid leukaemia cell is the cell line K562, KG-1, MUTZ-3, NM-F9 [DSM ACC2606], NM-D4 [DSM ACC2605], NM-H9, H9, NM-H10.

The method for generating a host cell of the invention with high sialylation and favourable biotechnological properties such as rapid cell growth comprising (i) incubating a human myeloid leukaemia cell of the invention as originator cell, preferably K562, with a lectin or preferably an antibody recognizing a desialylated epitope or an epitope lacking a sialic acid but which binds not or less the sialylated form of the epitope, such as but not limited to Nemod-TF1, Nemod-TF2, A78-G/A7, or PNA (lectin from *Arachis hypogaea*, peanut agglutinin), preferably bound to magnetic beads, and (ii) isolating cells bound to said lectin or antibody, and (iii) culturing the isolated cells for a suitable time, and (iv) select a cell, cells or a cell clone, preferably after single cell cloning, which strongly binds to a lectin or an antibody which binds to an epitope with sialic acid, such as SNA (*Sambucus nigra* agglutinin) or MAL (*Maackia amurensis* lectin), MAL I (*Maackia amurensis* lectin I), preferably SNA.

In a preferred embodiment the invention provides a method for generating a host cell of the invention with high sialylation and favourable biotechnological properties such as rapid cell growth comprising (i) incubating K562 with Nemod-TF1, Nemod-TF2, A78-G/A7, or PNA bound to magnetic beads, and (ii) isolating cells bound to said lectin or antibody, and (iii) culturing the isolated cells for a suitable time of about one to 6 weeks, and (iv) select a cell clone after single cell cloning, which strongly binds to SNA. In a preferred embodiment those cell bind stronger to SNA than the originator cell, and in another preferred embodiment they grow faster than the originator cell.

In a preferred embodiment of the invention the originator cell is treated with ethylmethanesulfonate prior to step (i).

Those skilled in the art are able to select suitable conditions and methods and optimise them in order to generate these host cells in sense of the invention. More details for some of the steps can be found under WO2005/017130 A2 and WO2005/080585 A1.

According to one embodiment, immortalised human blood cells are used as host cells, which are selected from the following groups 1 to 4:
  (a) group 1, comprising host cells having a high sialylation activity such as K562;
  (b) group 2, comprising host cells having due to a genetic deficiency or expression inhibition means (e.g. RNAi) a low or no sialylation; activity comparable to and including NM-F9 [DSM ACC2606], NM-D4 [DSM ACC2605] and GTX-2;
  (c) group 3, comprising host cells having a higher sialylation degree than K562 such as NM-H9 and NM-H9D8;
  (d) group 4, comprising host cells having a low or even no fucosylation activity such as NM-H9D8-E6 and NM H9D8-E6Q12.

In a preferred embodiment, said the cell line generated is NM-H9D8. As the most preferred cell clone generated by the method described above, NM-H9D8 was selected and deposited under DSM ACC 2806 at the "DSMZ-Deutsche Sammlung von Mikroorganismen and Zellkulturen GmbH" in Braunschweig (Germany), by Glycotope GmbH, Robert-Rössle-Str. 10, 13125 Berlin (Germany) on Sep. 15, 2006. Other cell clones such as NM-E-2F9, NM-C-2F5, or NM-H9D8-E6 (DSM ACC 2807) were selected by incubation of the parental cells with one or more lectins and following single cell cloning using flow cytometry cell sorting whereby a positive selection procedure or a combination of negative and positive selection was performed. To get cell clones with stable characteristics obtained cell clones were recloned at least once by limited dilution as described above.

In a preferred embodiment of the invention said immortalized human blood cell which is preferably a host cell of myeloid leukaemia origin, grows and produces the protein/antibody molecule composition of the invention under serum-free conditions. In an even further preferred embodiment said immortalized human blood cell which is preferably a host cell of myeloid leukaemia origin grows under serum-free conditions. Furthermore, also the nucleic acid encoding the protein/antibody molecule can be introduced in these cells and the protein/antibody molecule composition can also be isolated under serum-free conditions. To be able to work under serum-free conditions is particularly important when preparing therapeutic proteins, as serum contaminations are unacceptable in the regulatory process.

In a preferred embodiment of the invention the host cell of human myeloid leukaemia origin of the invention is the cell or cell line K562, KG1, MUTZ-3, NM-F9 [deposited under DSM ACC 2606 at the "DSMZ-Deutsche Sammlung von Mikroorganismen und Zellkulturen GmbH" in Braunschweig (Germany), by Nemod Biotherapeutics GmbH & Co.KG, Robert-Rossle-Str. 10, 13125 Berlin (Germany) on Aug. 14, 2003], NM D4 [deposited under DSM ACC 2605 at the "DSMZ-Deutsche Sammlung von Mikroorganismen und Zellkulturen GmbH" in Braunschweig (Germany), by Nemod Biotherapeutics GmbH & Co.KG, Robert-Rossle-Str. 10, 13125 Berlin (Germany) on Aug. 14, 2003] or a cell or cell line derived from any one of said host cells, or a mixture of cells or cell lines comprising at least one of those aforementioned cells. The host cell is preferably selected from the group consisting of NM-F9 [DSM ACC2606], NM-D4 [DSM ACC2605], NM-E-2F9, NM-C-2F5, NM-H9D8 [deposited under DSM ACC 2806 at the "DSMZ-Deutsche Sammlung von Mikroorganismen und Zellkulturen GmbH" in Braunschweig (Germany), by Glycotope GmbH, Robert-Rossle-Str. 10, 13125 Berlin (Germany) on Sep. 15, 2006], or NM-H9D8-E6 [deposited under DSM ACC 2807 at the "DSMZ-Deutsche Sammlung von Mikroorganismen und Zellkulturen GmbH" in Braunschweig (Germany), by Glycotope GmbH, Robert-Rossle-Str. 10, 13125 Berlin (Germany) on Oct. 5, 2006], or NM H9D8-E6Q12 [deposited under DSM ACC 2856 at the "DSMZ-Deutsche Sammlung von Mikroorganismen und Zellkulturen GmbH" in Braunschweig (Germany), by Glycotope GmbH, Robert-Rossle-Str. 10, 13125 Berlin (Germany) on Aug. 8, 2007], GT-2X [deposited under DSM ACC 2858 at the "DSMZ-Deutsche Sammlung von Mikroorganismen and Zellkulturen GmbH" in Braunschweig (Germany), by Glycotope GmbH, Robert-Rossle-Str. 10, 13125 Berlin (Germany) on Sep. 7, 2007] or a cell or cell line derived from any of these cell lines.

The cells NM-F9 [DSM ACC2606] and NM-D4 [DSM ACC2605] were deposited by Nemod Biotherapeutics GmbH & Co.KG, Robert-Rössle-Str. 10, 13125 Berlin, Germany, who authorised the applicant to refer to the deposited biological material described herein.

In a further preferred embodiment of the invention the host cell of human myeloid leukaemia origin of the invention is the cell or cell line K562, NM-F9 [DSM ACC2606], NM-D4 [DSM ACC2605], or a cell or cell line derived from anyone of said host cells.

In a preferred embodiment of the invention the host cell of human myeloid leukaemia origin of the invention is the cell or cell line K562, such as K562 [ATCC CCL-243], or a cell or cell line derived from said host cell.

In a further preferred embodiment of the invention the host cell of human myeloid leukaemia origin of the invention is the cell or cell line K562, NM-F9 [DSM ACC2606], NM-D4 [DSM ACC 2605], NM-E-2F9, NM-C-2F5, NM-H9D8, or NM-H9D8-E6, or GT-2X, or NM H9D8-E6Q12 or a cell or cell line derived from anyone of said host cells.

In an even more preferred embodiment of the invention the host cell of human myeloid leukaemia origin of the invention is the cell, cells or cell line K562, NM-F9 [DSM ACC2606], NM-D4 [DSM ACC2605], NM-E-2F9, NM-C-2F5, NM-H9D8, or NM-H9D8-E6, or GT-2X, or NM H9D8-E6Q12 which grow and produce an antibody molecule composition of the invention under serum-free conditions, and most preferred hereunder cell, cells or cell line growing under serum-free conditions and the nucleic acid encoding the antibody molecule can be introduced in these cells and an antibody molecule composition is isolated under serum-free conditions.

In the most preferred embodiment of the invention the host cell of human myeloid leukaemia origin of the invention is the cell, cells or cell line NM-F9 [DSM ACC2606], NM-D4 [DSM ACC2605], NM-E-2F9, NM-C-2F5, NM-H9D8, GT-2X, or NM-H9D8-E6, or NM M9D8-E6Q12 which grow and produce an antibody molecule composition of the invention under serum-free conditions, and most preferred hereunder cell, cells or cell line growing under serum-free conditions and the nucleic acid encoding the antibody molecule can be introduced in these cells and an antibody molecule composition is isolated under serum-free conditions.

According to one embodiment, the immortalized human blood cell and the host cell of human myeloid leukaemia origin is not one of the sialylation deficient cell lines NM-F9 and NM-D4 or a cell or cell line derived from anyone of said host cells having the same properties. This embodiment is beneficial in case a high degree of sialylation is aimed at. For these embodiments, the host cell is preferably selected from the group consisting of K562, NM H9D8, NM H9D8-E6, NM H9D8-E6Q12 and host cells derived from any of these host cells.

The cell lines described in conjunction with the present invention have a doubling time from 14 to 24 hours which is very fast compared to other mammalian expression system, depending on the cell line of the invention.

Furthermore no general suitable high expression vector system is known for high yield antibody expression in human cell lines since human cells normally do not lack the DHFR gene and hence do not allow the use of the dhfr/methotrexate amplification system. Hence, according to a further embodiment of the present invention an embodiment is provided, which allows to increase the product yield.

According to this embodiment, additionally a nucleic acid is introduced in the host cell, encoding an antifolate resistant DHFR-variant. The dihydrofolate reductase, or DHFR, reduces dihydrofolic acid to tetrahydrofolic acid, using NADPH as electron donor, which can be converted to the kinds of tetrahydrofolate cofactors used in 1-carbon transfer chemistry. Antifolates inhibit the DHFR enzyme, leading to cell death. To provide a nucleic acid encoding an antifolate-resistant DHFR variant, a tool is provided to select cells which were transfected with the nucleic acid and furthermore, allows an amplification of the nucleic acids to be expressed in the host cells.

The nucleic acid encoding said antifolate resistant DHFR-variant can e.g. be introduced via a separate vector than the nucleic acid encoding the protein/antibody to be expressed in the host cell. It is preferred to transfect the vector encoding the antifolate resistant DHFR-variant basically at the same time as the vector comprising the nucleic acid encoding the protein/antibody. This embodiment encourages that the nucleic acid encoding said protein/antibody to be expressed is integrated in the genome of the host cell at the same genetic site as the nucleic acid encoding the antifolate resistant DHFR-variant which is beneficial in case an amplification of the nucleic acid encoding said protein/antibody is desired.

Alternatively, a vector system may be used which comprises the nucleic acid encoding at least a part of said protein to be expressed as well as the nucleic acid encoding the antifolate resistant DHFR-variant.

The host cells are then cultured with said antifolate. This has the effect that those host cells, which were successfully transfected with the nucleic acid encoding said antifolate resistant DHFR-variant can grow despite the presence of the antifolate. Thereby successfully transfected cells can be selected.

According to a further embodiment, the nucleic acid sequence encoding at least part of said protein/antibody is amplified by stepwise increasing the antifolate concentration in the culture. The increase of the antifolate concentration in the culture medium leads to an increase of the copies of the antifolate resistant DHFR-variant in the genome. It is assumed that this is achieved by recombination events in the cells. Thereby, also the copy number of the nucleic acid encoding at least part of the protein to be expressed is also increased if the nucleic acid encoding said protein is located near the antifolate resistant DHFR variant in the genome what can be promoted by either transfecting separate vectors simultaneous or by using one vector comprising both nucleic acid sequences. By this mechanism host cells are obtained, which express the protein/antibody at a higher yield.

Preferably, the antifolate is methotrexate.

The nucleic acid sequence encoding said protein, preferably an antibody molecule or a part thereof, is preferably amplified by culturing said host cell with at least two successive rounds of antifolate, preferably methotrexate, whereby the concentration of said antifolate, preferably methotrexate, is increased by at least 100% in each successive round.

A suitable nucleic acid for providing said antifolate resistant DHFR-variant encodes a polypeptide of the group of sequence ID No. 1 to 9, preferably sequence ID No 1.

Further details and embodiments on this amplification system are also described in further detail below.

The invention also provides a method for producing a protein, preferably an antibody molecule composition comprising:
(a) introducing in a host cell of human myeloid leukaemia origin at least one nucleic acid encoding a protein and preferably an antibody molecule or at least one part thereof, and at least one nucleic acid comprising at least one nucleic acid sequence encoding at least one polypeptide of the group of sequence #1 to sequence #9, preferably sequence #1; and
(b) amplifying the nucleic acid sequence encoding said protein, preferably an antibody molecule or at least one part thereof by culturing said host cell with methotrexate, preferably by culturing said host cell with at least two successive rounds of methotrexate whereby the concentration of methotrexate is preferably increased by at least about 50%, more preferably by at least about 100%, in each successive round; and
(c) culturing said host cell under conditions which permits the production of said protein, preferably an antibody molecule composition, and
(d) isolating said protein, which preferably is an antibody molecule composition.

The invention also provides a method for producing a protein composition, preferably an antibody molecule composition having increased activity and/or increased yield and/or improved homogeneity comprising:
(a) introducing in a host cell of human myeloid leukaemia origin at least one nucleic acid encoding protein, preferably an antibody molecule or at least one part thereof; and
(b) culturing said host cell under conditions which permits the production of said protein composition, which preferably is an antibody molecule composition; and
(c) isolating said protein composition, which preferably is an antibody molecule composition having increased activity and/or increased yield and/or improved homogeneity.

Furthermore, the invention provides a method for producing protein composition, preferably an antibody molecule composition having increased activity and/or increased yield and/or improved homogeneity comprising:
(a) introducing in a host cell of human myeloid leukaemia origin at least one nucleic acid encoding a protein, preferably an antibody molecule or at least one part thereof, and at least one nucleic acid comprising at least one nucleic acid sequence encoding at least one polypeptide of the group of sequence #1 to sequence #9, preferably sequence #1; and
(b) amplifying the nucleic acid sequence encoding said antibody molecule or at least one part thereof by culturing said host cell with methotrexate, preferably by culturing said host cell with at least two successive rounds of methotrexate whereby the concentration of methotrexate is preferably increased by at least about 50%, more preferably by at least about 100%, in each successive round; and
(c) culturing said host cell under conditions which permits the production of said protein composition, which preferably is an antibody molecule composition; and
(d) isolating said protein composition, which preferably is an antibody molecule composition having increased activity and/or increased yield and/or improved homogeneity.

Said nucleic acid encoding an antibody molecule or at least one part of it and said nucleic acid comprising at least one nucleic acid sequence encoding at least one polypeptide of the group of sequence #1 to sequence #9, preferably sequence #1, can be one nucleic acid or two separate nucleic acids.

In order to select a suitable host cell for obtaining a protein having an optimised glycosylation profile, it is advantageous to perform the screening/selection method according to the present invention. After a suitable host cell is determined by the selection method according to the present invention, said host cell is then used for producing the protein as defined in claims 1 to 20.

Hence, the invention also provides a method for selecting a host cell for producing a protein having at least one of the following glycosylation characteristics:
(i) it comprises no detectable NeuGc; and/or
(ii) it has a galactosylation degree on the total carbohydrate structures or on the carbohydrate structures at one particular glycosylation site of the protein molecule of the protein molecules in said protein molecule composition, that is increased compared to the same amount of protein molecules in at least one protein molecule composition of the same protein molecule isolated from CHOdhfr− [ATCC No. CRL-9096] when expressed therein; and/or (iii) it has an amount of G2 structures on the total carbohydrate structures or on the carbohydrate structures at one particular glycosylation site of the protein molecule of said protein molecules in said protein molecule composition which is at least 5% higher compared to the same amount of protein molecules in at least one protein molecule composition of the same protein molecule isolated from CHOdhfr− [ATCC No. CRL-9096] when expressed therein; and/or (iv) it has an amount of G0 structures on the total carbohydrate structures or on the carbohydrate structures at one particular glycosylation site of the protein molecule of said protein molecules in said protein molecule composition which is at least 5% lower compared to the same amount of protein molecules in at least one protein molecule composition of the same protein molecule isolated from CHOdhfr− [ATCC No. CRL-9096] when expressed therein; and/or (v) it comprises no detectable terminal Galalpha1-3Gal; and/or (vi) it comprises an amount of fucose on the total carbohydrate structures or on the carbohydrate structures at one particular glycosylation site of the protein molecule of said protein molecules in said protein molecule composition which is at least 5% less compared to the same amount of protein molecules in at least one protein molecule composition of the same protein molecule isolated from CHOdhfr− [ATCC No. CRL-9096] when expressed therein; and/or (vii) it comprises at least one carbohydrate structure containing bisecting GlcNAc; and/or (viii) it has a sialylation pattern which is altered compared to the sialylation pattern of at least one protein molecule composition of the same protein molecule isolated from CHOdhfr− [ATCC No. CRL-9096] when expressed therein;

by the following steps
(a) introducing in at least two different immortalized human blood cells as host cells at least one nucleic acid encoding a protein or at least one part thereof; and
(b) culturing said at least two different host cells, wherein each different host cell produces a protein composition having a glycosylation pattern diverging from the glycosylation pattern produced by the other host cell;
(c) isolating said expressed protein compositions carrying a different glycosylation pattern from the at least two different host cells; and
(d) selecting said host cell producing a protein composition which as at least one of the glycosylation characteristics defined in (i) to (viii).

The details regarding the glycosylation pattern and suitable cell lines for obtaining said pattern are described above and are also applicable to and suitable for the screening method for selecting a suitable host cell according to the present invention.

To perform a respective screening step prior to establishing the production method as described in claims 1 to 20 is advantageous as this embodiment allows the selection of the most suitable host cell for producing the protein/antibody molecule composition having an optimised glycosylation pattern. According to the basic idea of this screening system, the protein of interest is expressed in at least two different cell lines which have a diverging glycosylation pattern. E.g. one cell line may depict a high degree of sialylation and the other one may depict a low degree of sialylation (or fucosylation and/or galactosylation) or even unknown glycosylation characteristics. The products obtained from the different cell lines accordingly carry a glycosylation pattern characteristic for the respective cell line.

The characteristics of the proteins produced in the different cell lines e.g. with respect to their activity (e.g. ADCC and CDC in antibodies), affinity, serum half-life and other important characteristics can then be determined. The results allow to choose the cell line, which has the best glycosylation machinery in order to obtain a protein which is optimised regarding its glycosylation pattern. As the decisive characteristics (e.g. affinity, serum half-life etc.) vary, this method is particularly advantageous.

Preferably, said protein to be produced depicts at least one of the following characteristics:
(a) in case it is an antibody molecule composition it has an increased Fc-mediated cellular cytotoxicity which is at least 2 times higher than the Fc-mediated cellular cytotoxicity of at least one antibody molecule composition from the same antibody molecule when expressed in the cell line CHOdhfr− [ATCC No. CRL-9096];
and/or
(b) in case it is an antibody molecule composition it has an increased antigen mediated or Fc-mediated binding which is at least 50% higher than the binding of at least one antibody molecule composition from the same antibody molecule when expressed in the cell line CHOdhfr− [ATCC No. CRL-9096];
and/or
(c) it has an increased average or maximum yield of said protein molecule composition which is at least 10% higher than the yield of at least one protein molecule composition from the same protein molecule when expressed in the cell line CHOdhfr− [ATCC No. CRL-9096].

According to one embodiment, at least one of said host cells is an immortalised human blood cell and preferably a cell of human myeloid leukaemia origin such as K562, NM-F9 [DSM ACC2606], NM-D4 [DSM ACC2605], NM-E-2F9, NM-C-2F5, NM-H9D8, NM-H9D8-E6, NM-H9D8-E6Q12, GT-2X or a cell or cell line derived therefrom.

Said at least one host cell of human myeloid leukaemia origin can be selected from one of the following groups 1 to 4:
(a) group 1, comprising host cells having a high sialylation activity such as K562 or a cell or cell lined derived therefrom,
(b) group 2, comprising host cells due to a genetic deficiency or expression suppression means (e.g. RNAi) a low or no sialylation such as NM-F9 [DSM ACC2606], NM-D4 [DSM ACC2605] and GTX-2 or a cell or cell lined derived therefrom,
(c) group 3, comprising host cells having a higher sialylation degree than K562 such as NM-H9 and NM-H9D8 or a cell or cell lined derived therefrom,
(d) group 4, comprising host cells having a low or no fucosylation activity such as NM-H9D8-E6 or a cell or cell lined derived therefrom.

Preferably, at least two or three host cells used in the screening process are selected from the above groups. However, it is also possible to include other host cells derived from another origin (e.g. Hek 293 cells) in the screening system according to the present invention in order to further broaden the different glycosylations patterns analysed.

The host cell obtained preferably produces a protein, in particular an antibody depicting at least one of the glycosylation patterns shown in Table 9.

According to the invention the term introducing a nucleic acid means any method known to those skilled in the art to introduce a nucleic acid, or two or more nucleic acids into a mammalian host cell or cells by methods such as but not limited to electroporation, transfection using cationic lipids, calcium phosphate, DEAE-dextran, or infection by virus particles such as adenoviruses or retroviruses or a combination thereof. Those skilled in the art are able to select and optimise a suitable method for introduction of one or more nucleic acids of the invention.

In accordance with the present invention the nucleic acid encoding an antibody molecule is any nucleic acid which encodes the antibody molecule or at least one part thereof. The antibody molecule of the invention can thereby be encoded by a single or by multiple nucleic acid molecules.

Said part of an antibody molecule encoded by said nucleic acid comprises at least one 20 amino acid sequence, more preferably at least 100 amino acids of an antibody molecule or of a constant and/or variable domain of the antibody molecule. The comprised sequence encoding the antibody molecule or at least one part thereof can be separated by at least one other sequence, such as e.g. an intron. The sequence of a domain can comprise at least one amino acid mutation.

In accordance with the present invention the nucleic acid encoding a protein molecule is any nucleic acid which encodes the protein molecule or at least one part thereof. The protein molecule of the invention can thereby be encoded by a single or by multiple nucleic acid molecules. The sequence encoding the protein molecule or at least one part thereof can be separated by at least one other sequence, such as e.g. an intron. The sequence of the protein molecule can comprise at least one amino acid mutation.

In a preferred embodiment the nucleic acid encoding an antibody molecule or at least one part of it comprises at least one variable and/or at least one constant domain of the antibody molecule, more preferably both, more preferably such which comprises a human sequence at least in the part of the constant domain or domains, and even more preferred such which comprises the human Cgamma2 domain, and most preferably it comprises all constant domains of the Fc region of a human antibody of a certain class or subclass and the variable domain.

According to one embodiment the protein and in particular antibody molecule is encoded by a single nucleic acid. In another preferred embodiment protein, in particular an antibody molecule is encoded by two nucleic acids or by three nucleic acids.

In a further preferred embodiment one nucleic acid encodes one part of the antibody molecule which encodes for the variable and/or the constant domain of the light chain and another nucleic acid encodes for another part of the antibody molecule which encodes for the variable and/or at least one constant domain of the heavy chain.

In accordance with the present invention the nucleic acid comprising at least one nucleic acid sequence encoding at least one polypeptide of the group of sequence #1 to sequence #9 means that said nucleic acid encodes for at least one polypeptide of the group of sequence #1 to sequence #9, preferably sequence #1. Any number of these sequences is suitable, as long as it can be introduced successfully into the host cell of the invention. In a preferred embodiment said nucleic acid encodes for one, two or three polypeptides of the group of sequence #1 to sequence #9, more preferably for one polypeptide, and most preferably for the polypeptide of sequence #1. In sense of the invention said nucleic acid can also encode for a polypeptide of the group of sequence #1 to sequence #9, preferably sequence #1, which has at least one amino acid mutation as long as this mutation allows the amplification of the nucleic acid encoding an antibody molecule or at least one part thereof by methotrexate as described elsewhere herein.

The nucleic acid sequence encoding at least one polypeptide of the group of sequence #1 to sequence #9, preferably sequence #1, can be part of the same nucleic acid molecule as the nucleic acid encoding an antibody molecule or at least one part thereof as described elsewhere herein or on separate nucleic acid molecules.

In another preferred embodiment of the invention a separate nucleic acid comprising a nucleic acid sequence encoding a sequence selected from the group of sequence #1 to sequence #9, most preferably sequence #1, can be introduced into the host cell of the invention separately from said nucleic acid or nucleic acids encoding the antibody molecule or parts thereof of the invention. This can be done either by introducing said separate nucleic acid comprising a nucleic acid sequence encoding a sequence selected from the group of sequence #1 to sequence #9, together, before or after introducing said nucleic acid or nucleic acids encoding the antibody molecule or parts thereof of the invention. In a preferred embodiment this is performed in parallel and in another preferred embodiment the host cell of the invention already comprises said separate nucleic acid comprising a nucleic acid sequence encoding a sequence selected from the group of sequence #1 to sequence #9, most preferably sequence #1.

Further preferred embodiments are described in the examples.

Amplification of stably introduced said nucleic acid or several copies of said nucleic acid encoding the protein, which is preferably an antibody molecule or fraction thereof can be performed as described elsewhere herein and in the examples using methotrexate.

In a preferred embodiment the nucleic acid encoding a protein, which is preferably an antibody molecule or at least one part thereof comprise at least one other genetic element which allow the selection of those cells in which the nucleic acid was successfully introduced, such as but not limited to antibiotic resistance genes, such as but not limited to the genetic element coding for a puromycin or neomycin resistance. Furthermore these nucleic acids comprise one or several genetic elements such as promoters, enhancers, polyadenylation sites, and/or introns, for expression of the antibody molecule in the host cells of the invention, and genetic elements such as bacterial origin of replication, promoters and elements for selection of transfected bacteria such as antibiotic resistance genes for multiplying the nucleic acid in a bacteria.

Suitable promoters include the promoter of IE (immediate early) gene of cytomegalovirus (CMV), SV40 early promoter, the promoter of a retrovirus, metallothionein promoter, heat shock promoter, SR alpha promoter, EF-1alpha promoter, etc. The enhancer of IE gene of human CMV may be used in combination with the promoter.

Those and further genetic elements are known to those skilled in the art and can be selected, combined, optimised and introduced into said nucleic acid encoding a protein, which is preferably antibody molecule or at least one part thereof by those skilled in the art. Preferred embodiments of said nucleic acid encoding a protein, which is preferably an antibody molecule or at least one part thereof or a combination of nucleic acids are described herein and in the examples as well as preferred genetic elements for use and combination, however, the invention is not restricted to the use of those and can be combined or further optimised by those skilled in the art.

Those skilled in the art are able to select and/or combine the suitable genetic element, construct the according nucleic acid vectors or elements to introduce one or more nucleic acids of the invention into a cell line according to the invention.

Said nucleic acid or combination of nucleic acids encoding the protein, which is preferably an antibody molecule or at least one part thereof, as well as said additional genetic elements, as well as the methods to introduce them such as transfecting them in the host cells of the invention for expression of the antibody molecule composition or into bacteria for multiplication are known to those skilled in the art as well as the methods to construct, identify, test, optimise, select and combine these nucleic acid or acids and combine them with suitable additional sequences for selection of those cells which are successfully transfected as well as methods to construct, identify, test and select most suitable nucleic acids encoding these antibody molecules are known to those skilled in the art.

Preferred embodiments of the invention are described in detail in the examples.

In a preferred embodiment of the invention the nucleic acid encoding a protein, which is preferably an antibody molecule or at least one part thereof comprises a genetic element for selection of those host cells of the invention in which the nucleic acid is successfully introduced such as but not limited to neomycin or puromycin, more preferably it comprises in addition a promoter such as EF-1alpha or CMV promoter, more preferably it comprises in addition a CMV enhancer, more preferably it comprises in addition a genetic element which allows the selection of bacteria which are transfected with the nucleic acid and a genetic element for replication such as the ColE1 replication origin for multiplication of said nucleic acid in bacteria, and even more preferably it comprises in addition a genetic element for multiplication of said the nucleic acid in COS cells such as the SV40 origin. These elements are known to those skilled in the art and can be selected, combined, optimised and used by those skilled in the art.

In an even further preferred embodiment of the invention said above described nucleic acid encoding a protein molecule or at least one part thereof comprises one nucleic acid sequence. Preferably said nucleic acid encoding protein molecule or at least one part thereof encodes additionally for the genetic element encoding puromycin resistance, or neomycin resistance, or a nucleic acid sequence encoding at least one sequence selected from the group of sequence #1 to sequence #9, most preferably sequence #1.

In an even further preferred embodiment of the invention said above described nucleic acid encoding an antibody molecule or at least one part thereof comprises at least one sequence encoding the variable domain and at least one constant domain of the heavy and/or the light chain of the antibody molecule.

In an even further preferred embodiment of the invention said above described nucleic acid encoding an antibody molecule or at least one part thereof comprises at least one sequence encoding the variable domain and constant domain of the light chain of the antibody molecule or the variable domain and all constant domains of the heavy chain of the whole antibody molecule.

In an even further preferred embodiment of the invention one of said above described nucleic acid encodes at least one part of the antibody molecule comprising at least one sequence encoding the variable domain and the constant domain of the light chain of the antibody molecule and a second of said above described nucleic acid encodes at least one other part of the antibody molecule comprising at least one sequence encoding the variable domain and at least one constant domain, preferably all constant domains of the heavy chain of the antibody molecule, and both nucleic acids are introduced into the same host cell of the invention. Preferably one of said nucleic acids encodes additionally for the genetic element encoding puromycin resistance and the other said nucleic acid encodes additionally for the genetic element encoding neomycin resistance.

In an even further preferred embodiment of the invention said above described nucleic acid encoding a protein molecule or at least one part thereof comprises at least two nucleic acid sequences encoding two amino acid sequences of the protein molecule or at least one part thereof.

Preferably one of said nucleic acids encodes additionally for the genetic element encoding puromycin resistance, one other said nucleic acid encodes additionally for the genetic element encoding neomycin resistance. More preferably one of said nucleic acids encodes additionally for the genetic element encoding puromycin or neomycin resistance, preferably puromycin resistance, and one other said nucleic acid comprises in addition a nucleic acid sequence encoding at least one sequence selected from the group of sequence #1 to sequence #9, most preferably sequence #1.

In an even further preferred embodiment of the invention said above described nucleic acid encoding a protein molecule or at least one part thereof comprises three nucleic acid sequences encoding three amino acid sequences of the protein molecule or at least one part thereof.

Preferably one of said nucleic acids encodes additionally for the genetic element encoding puromycin resistance, one other said nucleic acid encodes additionally for the genetic element encoding neomycin resistance, and one other said nucleic acid comprises in addition a nucleic acid sequence encoding at least one sequence selected from the group of sequence #1 to sequence #9, most preferably sequence #1.

In an even more preferred embodiment one of said nucleic acids encodes additionally for the genetic element encoding a puromycin or neomycin resistance and the other said nucleic acid comprises in addition a nucleic acid sequence encoding at least one sequence selected from the group of sequence #1 to sequence #9, most preferably sequence #1. In a even more preferred embodiment one of said nucleic acids comprising sequences encoding the variable domain and the constant domain of the light chain and comprises in addition a nucleic acid sequence encoding at least one sequence selected from the group of sequence #1 to sequence #9, most preferably sequence #1, and the other said nucleic acid comprises sequences encoding the variable domain and at least one constant domain, preferably all constant domains, of the heavy chain of the antibody molecule and comprises in addition a nucleic acid sequence encoding for a puromycin or neomycin resistance, preferably puromycin resistance.

In an even further preferred embodiment of the invention said nucleic acid encoding the antibody molecule or at least one part thereof comprises at least one sequence encoding the variable domain and the constant domain of the light chain of the antibody molecule and at least one sequence encoding the variable domain and at least one constant domain, preferably all constant domains of the heavy chain of the antibody molecule.

In a preferred embodiment of the invention the constant domains encoded by above or elsewhere described nucleic acids of the invention are human constant domains of IgG or IgM, preferably, human IgG1, IgG4 or IgM, or one domain or a combination of domains thereof, whereby preferably genomic sequences or sequences derived from genomic sequences comprising at least one intron are used, which can be selected, constructed and optimised by those skilled in the art.

In a further preferred embodiment of the invention said nucleic acid encoding a protein, which is preferably an antibody molecule or at least one part thereof of the invention further comprises the EF-1 alpha promoter/CMV enhancer or a CMV promoter derived promoter, preferably CMV-E.

In a further preferred embodiment of the invention said nucleic acid encoding a protein, which is preferably an antibody molecule or at least one part thereof of the invention further comprises a secretion signal peptide, preferably the T cell receptor secretion signal.

In an even further preferred embodiment of the invention said nucleic acid encoding a protein, which is preferably an antibody molecule or at least one part thereof of the invention further comprises a secretion signal peptide, preferably the sequence #10.

Said nucleic acid or combination of nucleic acids encoding a protein, which is preferably an antibody molecule or at least one part thereof, as well as said additional genetic elements, as well as the methods to introduce them are known to those skilled in the art as well as the methods to construct, identify, test, optimise, select and combine these nucleic acid or acids and combine them with suitable additional sequences for selection of those cells which are successfully transfected as well as methods to construct, identify, test and select most suitable nucleic acids encoding these antibody molecules are known to those skilled in the art.

Preferred embodiments of the invention are described in detail in the examples.

The introduction of the nucleic acid can be either transient or stable.

In accordance with the present invention the term amplifying the nucleic acid sequence encoding a protein or antibody molecule or at least one part thereof by culturing said host cell with an antifolate, in particular methotrexate means that a host cell of the invention described elsewhere herein in which at least one nucleic acid encoding the protein to be expressed such as e.g. an antibody molecule or at least one part thereof, and at least one nucleic acid comprising at least one nucleic acid sequence encoding an antifolate resistant DHFR variant, preferably at least one polypeptide of the group of sequence #1 to sequence #9, preferably sequence #1, was introduced an is cultivated by at least one antifolate, preferably methotrexate concentration. A typical cultivation time is between one to two weeks for each round, at typical concentrations from about 20 nM bis 3000 nM, preferably between about 50 nM to 2000 nM, more preferably between about 100 nM to 2000 nM. The duration of an antifolate/methotrexate amplification treatment as well as the concentration and the according vectors of nucleic acids of the invention can be optimised by those skilled in the art and is also described in a preferred embodiment in the examples. Optimal amplification conditions can differ between different proteins/antibody molecules encoded and usage of different nucleic acids or nucleic acid constructs or combinations thereof described afore. Those skilled in the art are able to select and optimise the most suitable conditions and nucleic acids of the invention. Said amplification leads to an integration of more nucleic acid copies encoding the protein/antibody molecule or at least one part thereof into the genome of the host cell than without antifolate/ methotrexate cultivation or than without the introduction of the nucleic acid sequence encoding at least one antifolate resistant DHFR variant, in particular a polypetide of the group of sequence #1 to sequence #9 and/or it leads to an increased production of the protein/antibody molecule composition.

In a preferred embodiment of the invention said host cell for amplification of the nucleic acid or nucleic acids encoding a protein/antibody molecule or at least one part thereof, which was introduced in said host cell in which at least one nucleic acid comprising at least one nucleic acid sequence encoding at least one polypeptide of the group of sequence #1 to sequence #9, preferably sequence #1, was introduced, as described elsewhere herein including its preferred embodiments, are a human myeloid leukaemia origin, preferably the cell or cell line KG1, MUTZ-3, K562, NM-F9 [DSM ACC2606], NM-D4 [DSM ACC2605], NM-E-2F9, NM-C-2F5, NM-H9D8, or NM-H9D8-E6, NM-H9D8-E6Q12, GT-2X or a cell or cell line derived from anyone of said host cells, more preferably the cell or cell line K562, NM-F9 [DSM ACC2606], NM-D4 [DSM ACC2605], NM-E-2F9, NM-C-2F5, NM-H9D8, or NM-H9D8-E6, NM-H9D8-E6Q12, GT-2X or a cell or cell line derived from anyone of said host cells, and even more preferably the cell or cell line NM-F9 [DSM ACC2606], NM-D4 [DSM ACC2605], NM-E-2F9, NM-C-2F5, NM-H9D8, or NM-H9D8-E6, NM-H9D8-E6Q12, GT-2X or a cell or cell line derived from anyone of said host cells.

In a preferred embodiment of the invention said host cell is cultivated with at least two successive rounds of antifolate/methotrexate whereby the concentration of antifolate/ methotrexate is preferably increased by at least about 50%, more preferably by at least about 100%, in each successive round. In an even further preferred embodiment of the invention said host cell is cultivated with at least three, more preferably with four, more preferably with 5, and even more preferably with 6 successive rounds of antifolate/methotrexate, whereby the concentration of antifolate/methotrexate is preferably increased by at least about 50%, more preferably by at least about 100%, in each successive round. Even more preferred are concentrations of antifolate/methotrexate between about 20 nM and 3000 nM, more preferred between about 50 nM to 2000 nM, more preferably between about 100 nM to 2000 nM, and even more preferred of about 100 nM, 200 nM, 500 nM, 1000 nM, 2000 nM which are in the preferred embodiment are used in successive rounds starting from 100 nM.

It is surprising that the introduction of a nucleic acid sequence encoding an antifolate resistant DHFR-variant and preferably at least one polypeptide of the group of sequence #1 to sequence #9 allows the amplification of the nucleic acid sequence encoding the said protein/antibody molecule or at least one part thereof in the host cell of human myeloid leukaemia origin of the invention, and especially in K562, NM-F9 [DSM ACC2606], NM-D4 [DSM ACC2605], NM-E-2F9, NM-C-2F5, NM-H9D8, or NM-H9D8-E6, NM-H9D8-E6Q12, GT-2X or a cell or cell line derived from anyone of said host cells, by culturing with antifolate/ methotrexate.

It is especially surprising that the introduction of a nucleic acid sequence encoding at least one polypeptide of sequence #1 allows the amplification of the nucleic acid sequence encoding the said antibody molecule or at least one part thereof in the host cell of the invention, and especially in K562, NM-F9 [DSM ACC2606], NM-D4 [DSM ACC2605], NM-E-2F9, NM-C-2F5, NM-H9D8, or NM-H9D8-E6, NM-H9D8-E6Q12, GT-2X or a cell or cell line derived from anyone of said host cells, by culturing with methotrexate.

It is even more surprising that the introduction of a nucleic acid sequence encoding at least one polypeptide of the group of sequence #1 to sequence #9 allows an even further amplification of the nucleic acid sequence encoding the said antibody molecule or at least one part thereof in the host cell of the invention, and especially in K562, NM-F9 [DSM ACC2606], NM-D4 [DSM ACC2605], NM-E-2F9, NM-C-2F5, NM-H9D8, or NM-H9D8-E6, NM-H9D8-E6Q12, GT-2X or a cell or cell line derived from anyone of said host cells, by culturing said host cell with at least two successive rounds of methotrexate whereby the concentration of methotrexate is increased by at least about 50%, more preferably by at least about 100%, in each successive round.

It is even more surprising that the introduction of a nucleic acid sequence encoding at least one polypeptide of sequence #1 allows an even further amplification of the nucleic acid sequence encoding the said antibody molecule or at least one part thereof in the host cell of the invention, and especially in K562, NM-F9 [DSM ACC2606], NM-D4 [DSM ACC2605], NM-E-2F9, NM-C-2F5, NM-H9D8, or NM-H9D8-E6, NM-H9D8-E6Q12, GT-2X or a cell or cell line derived from anyone of said host cells, by culturing said host cell with at least two successive rounds of methotrexate whereby the concentration of methotrexate is increased by at least about 50%, more preferably by at least about 100%, in each successive round.

In a preferred embodiment, the term that amplification is stable means that it leads to the production of high yields of the antibody molecule composition over at least 35 generations of host cell division cycles. Amplification of stably introduced said nucleic acid or nucleic acids encoding the protein/antibody molecule or fraction thereof can be performed as described above and in the examples using methotrexate.

Further preferred embodiments are described in the examples.

In a preferred embodiment of the invention the host cell of the invention with introduced nucleic acids of the invention are preferably used after at least one round of single cell cloning and selection of those cell clones with suitable expression and secretion of said protein/antibody composition. Preferably said single cell cloning and selection of those cell clones with suitable expression and secretion of said protein/antibody composition occurs after at least one round of methotrexate amplification described elsewhere herein. In a further preferred embodiment, said cell clones are further amplified by at least one additional round of amplification with methotrexate, preferable an increased concentration of methotrexate, preferably at least about the double concentration of methotrexate, and even more preferred followed by a further round of single cell cloning and selection of those cell clones with suitable expression and secretion of said protein/antibody composition. With these preferred embodiments cell clones with particularly high expression yields can be selected.

In accordance with the present invention the term culturing said host cell under conditions which permits the production of said antibody molecule composition or a respective formulation for proteins in general means that the host cell of the invention comprising at least one nucleic acid encoding a protein/antibody molecule, preferably the preferred embodiments of said nucleic acid of the invention described elsewhere herein, is cultured under culture conditions which allow the expression of the protein/antibody molecule in form of a protein/antibody molecule composition, preferably secretion into the medium, preferably with high yields and/or high activity and/or high homogeneity as described elsewhere herein. Those skilled in the art are able to select the most suitable culture conditions by using suitable media and culture conditions such as but not limited to suitable time, temperature, pH, gasing, feed, medium, medium supplements, vessel or reactor sizes and principles known to those skilled in the art. Those skilled in the art are able to select and optimise the most suitable conditions. Preferred embodiments are described in examples but are not limited to those.

Culturing of the cells of the present invention can be carried out by any of general culturing methods for animal cells capable of efficiently producing the desired antibody molecule composition, for example, batch culture, repeated batch culture, fed-batch culture and perfusion culture. Preferably, fed-batch culture or perfusion culture is employed in order to raise the productivity of the desired polypeptides.

In a further preferred embodiment of the invention said culturing is performed under serum-free conditions and even further preferred with protein free media or animal component free media.

Adaptation of host cells of the present invention to a serum-free medium in accordance with the present invention is surprisingly fast and robust. Adaptation can be carried out, for example, by adapting cells subcultured in a serum-containing medium directly to a commercially available serum-free medium, or by continuous adaptation whereby the direct adaptation to serum-free medium is preferred and advantageous. During the process of adaptation to a serum-free medium, the viability of cells lowers temporarily, which sometimes causes extinction of cells. Therefore, it is preferred to inoculate cells into a medium for the adaptation to a serum-free medium at a cell density of $1 \times 10^5$ to $5 \times 10^5$ cells/ml, preferably $2 \times 10^5$ cells/ml, in order to restore the viability of cells or to keep it high. After 4 to 7 days of culturing, the cells whose density reached $5 \times 10^5$ to $10 \times 10^5$ cells/ml are selected as the cells adapted to a serum-free medium. Adaptation to serum-free medium can be also performed by successive dilution of the medium supplemented with FCS by a serum-free medium composition (continuous adaptation). Those skilled in the art are able to select and optimise the most suitable conditions. Preferred embodiments are described in examples but are not limited to those.

After the cells of the present invention are adapted to a serum-free medium, a cloned cell line can be prepared by using the limiting dilution method with a 96-well plate, the colony forming method, or the like, and cells or cell line are selected due to properties of those cells which are aventageous when compared to their parent cell or cell line such as but not limited to shorter doubling times, faster growth, possibility to grow under higher densities, can produce more, higher cloning efficiencies, higher transfection efficiencies for DNA, higher expression rates of antibody molecule compositions, higher activities for an antibody molecule composition expressed therein, higher homogeneities of an antibody molecule composition expressed herein, and/or higher robustness to scaling up. Methods for selecting the cell with advantageous properties are known to those skilled in the art or described herein.

In accordance with the present invention the term isolating said antibody molecule composition or a corresponding formulation for proteins in general means that the protein/antibody molecule composition expressed by said host cell comprising at least one of said nucleic acids encoding the protein/antibody molecule or fraction thereof described elsewhere herein is gained by using the culture media after culturing or further enriching or purifying the protein/antibody molecule composition or parts of said protein/antibody molecule composition by methods known to those skilled in art. Said protein/antibody molecule composition in sense of the invention also means parts of said protein/antibody molecule composition enriched for certain protein/antibody molecules described elsewhere herein.

In one preferred embodiment the protein/antibody molecule composition is isolated by separating the media after culturing from the cells and/or cell debris for example by centrifugation techniques.

In a further preferred embodiment of the invention a Protein/antibody molecule composition of the invention is isolated or further enriched by ultrafiltration, precipitation methods or other concentration methods known to those skilled in the art.

In a further preferred embodiment of the invention a protein/antibody molecule composition of the invention is isolated by purification of the protein/antibody molecule composition by chromatographic methods such as but not limited to affinity chromatography using according affinity materials such as but not limited to Protein A, Protein G, anti-antibody isotype antibodies, lectin chromatography, antibodies against a certain tag introduced into antibody molecule such as HIS-tag or myc-tag, or antigen, or by ion exchange chromatography known to those skilled in the art.

Further methods of purifying or enriching proteins or certain glycoforms of proteins are known to those skilled in the art and can be selected, adopted, optimised and used alone or in combination with afore described methods by those skilled in the art to isolate or further purify, fractionate or enrich the protein molecule composition or fractions thereof of the invention.

In a preferred embodiment of the invention an antibody molecule composition of the invention of mainly IgG is isolated by Protein A chromatography with or without prior ultracentrifugation.

In another preferred embodiment of the invention an antibody molecule composition of the invention of mainly IgM is isolated by anti-IgM antibody chromatography with or without prior ultracentrifugation.

In another preferred embodiment of the invention an antibody molecule composition of the invention enriched in certain glycoforms of the antibody molecule is isolated by lectin affinity chromatography with or without prior ultracentrifugation. Further methods of purifying or enriching proteins or certain glycoforms of proteins are known to those skilled in the art and can be selected, adopted, optimised and used alone or in combination with afore described methods by those skilled in the art to isolate or further purify, fractionate or enrich the antibody molecule composition or fractions thereof of the invention.

In a preferred embodiment the antibody molecule composition is isolated using Protein A columns. In another preferred embodiment the antibody molecule composition is isolated using an anti-IgM column.

In accordance with the present invention the term "increased activity" means that the activity of a protein and/or antibody molecule composition of the invention expressed in a host cell of human myeloid leukaemia origin is higher than the activity of at least one protein/antibody molecule composition from the same protein/antibody molecule when expressed in at least one of the cell lines CHO, or CHOdhfr−, or BHK, or NS0, or SP2/0, or PerC.6 or mouse hybridoma. In the preferred embodiment of the invention it means that the activity of a protein/antibody molecule composition of the invention expressed in a host cell of human myeloid leukaemia origin is higher than the activity of a protein/antibody molecule composition from the same protein/antibody molecule when expressed in CHOdhfr− [ATCC No. CRL-9096]. For antibodies, said increased activity is an increased Fc-mediated cellular cytotoxicity or an increased binding activity.

In the meaning of the invention, "activity" is also a function or set of functions performed by a protein molecule in a biological context. In the meaning of the invention, the term "increased activity", equivalents of the contents and grammatical equivalents thereof are to understood as an improved or optimal activity with regard to the selected application, whereby the activity could be either approximated to a limiting value, for example being minimized or maximized, or set to a medium value representing a higher or lower activity compared to the corresponding protein molecule produced by prior art. Improved or increased activity in sense of the invention also means a favorable activity in sense of its biological and/or pharmaceutical meaning as improved serum half-life, pharmacokinetics, stability, biological activity, binding, antigenicity and/or immunogenicity. For example, the biological activity of a protein molecule composition could be increased to an extend by decreasing adverse biological effects, e.g. by the reduced stimulation of adverse immune effects or a decreased immunogenicity.

Activity of the protein molecule composition according to the invention can be determined in a suitable bioassay which is able to determine the activity of the protein. Those skilled in the art are able to identify suitable bioassays or to build up suitable bioassays. According to the present invention such bioassays include for example biological in vitro assays, including cellular or molecular or mixed assays, such as proliferation assays, apoptosis assays, cell adhesion assays, signaling assays, migration assays, cell cytotoxicity assays, phagocytosis assays, lysis assays, and binding assays. Such bioassays also include in vivo assays using animal models or humans, such as biodistribution, pharmakokinetic, pharmacodynamic test, serum-half life tests, tests for bioavailability, efficacy test, localization tests, treatment and prophylaxe tests of diseases including clinical studies. Such bioassays also include chemical, physical, physiochemical, biophysical and biochemical tests, such as stability towards temperature, shear stress, pressure, pH, conjugation and others. Such bioassays also include tests for the immunogenicity and/or antigenicity in order to improve the properties of the protein molecule composition in respect to its clinical use. Those skilled in the art are able to determine the activity or a combination of described activities of protein molecule compositions.

In a preferred embodiment the higher activity of the protein molecule composition is characterized by a higher activity in at least one in vitro model and/or a higher activity in at least one in vivo model and/or a higher stability and/or a longer serum half-life and/or a longer bioavailability and/or an improved immunogenicity and/or an improved antigenicity determined by at least one bioassay. The improvement in the overall activity which is also called herein higher activity can lead for examples to improvements like lower dosages, longer time intervals for administration, less side effects and no or lower toxicity of the product when used in humans or according organisms resulting in largely improved pharmaceuticals.

In a preferred embodiment of the invention the activity of a protein molecule composition of the invention expressed in a host cell of human myeloid leukaemia origin is higher than the activity of at least one protein molecule composition from the same protein molecule produced by prior art.

Said increased Fc-mediated cellular cytotoxicity is an increased antibody dependent cellular cytotoxicity (ADCC activity), complement dependent cytotoxicity (CDC activity), and/or cytotoxicity caused by phagocytosis (phagocytosis activity). The increased Fc-mediated cellular cytotoxicity, including ADCC activity, CDC activity or phagocytosis activity can be determined by various methods known to those skilled in the art and some are described in detail in examples without limiting it to those methods whereby the methods described in the examples are preferred embodiments of the invention.

Said increased binding activity is an increased binding to the epitope of the antibody molecule, such as the epitope, the antigen, another polypeptide comprising the epitope, or a cell comprising the epitope of the antibody molecule, or an increased binding to at least one Fc receptor or another effector ligand, such as Fc-gammaRI, Fc-gammaRII, Fc-gammaRIII, and subclasses therefrom such as Fc-gammaRIIa, Fc-gammaRIIIa, Fc-gammaRIIIb, or C1q component of complement, or FcRn or a molecule or cell comprising any of those Fc receptors or effector ligands. The increased binding activity can be a higher affinity, a higher avidity, and/or a higher number of binding sites or combinations thereof. The increased binding activity can result in various effects and activities such as but not limited to forms of receptor mediated activity as described in the Background of the art. The increased binding affinity, avidity and receptor mediated activity can be determined by at least one of the various methods known to those skilled in the art such as but not limited to Biacore measurement, Scatchard analysis, ELISA or RIA based measurements, flow cytometry measurements, test for determining the apoptosis induction in suitable target cells, tests for determination of the proliferation of suitable target cells, test for antagonistic, agonistic and/or receptor blockade of an antibody molecule composition such as but not limited to inhibition of cell-cell mediated binding, trigger of cell internal molecular events. Those skilled in the art are able to select and/or adopt and/or modify a suitable method or combination of methods for testing the binding affinity, avidity, number of binding sites and/or receptor mediated activity.

The methods of the invention can be used to test the ability of an antibody to be able to obtain an increased Fc-mediated cellular cytotoxicity, preferably ADCC activity, CDC activity and/or cytotoxicity caused by phagocytosis, and/or an increased binding activity to the epitope of the antibody molecule or preferably to at least one Fc receptor or another effector ligand, in general and/or in particular with the host cells of the invention and its preferred embodiments described elsewhere herein.

In a preferred embodiment of the invention the activity of a protein/antibody molecule composition of the invention expressed in a host cell of human myeloid leukaemia origin is higher than the activity of at least one antibody molecule composition from the same antibody molecule from at least one of the cell lines CHO, or CHOdhfr–, or BHK, or NS0, or SP2/0, or PerC.6 or mouse hybridoma, preferably CHOdhfr– [ATCC No. CRL-9096], when expressed therein.

In a preferred embodiment of the invention the activity of a protein/antibody molecule composition of the invention expressed in a host cell of human myeloid leukaemia origin is at least 50% higher than the activity of the antibody molecule composition from the same antibody molecule expressed in the cell line CHOdhfr– [ATCC No. CRL-9096], more preferably at least 2 times, more preferably at least 3 times, more preferably at least 4 times, more preferably at least 5 times, more preferably at least 7 times, more preferably at least 10 times, more preferably at least 15 times, more preferably at least 23 times, more preferably at least 30 times, more preferably at least 50 times, more preferably at least 75 times, more preferably at least 100 times, more preferably at least 150 times, more preferably at least 150 times, more preferably at least 230 times, more preferably at least 300 times, more preferably at least 500 times, more preferably at least 750 times, and most preferably more than 1000 times.

Thereby not each bioassays has to show a higher activity but depending on the use and the features of a particular protein molecule composition some favourable biological effects can compensate for others which are less favourable and still resulting in a overall higher activity of the protein molecule composition in sense of the invention. For example, a certain protein molecule composition can result in a much higher activity by binding to its receptors to cells thereby triggering secondary effect, such as induction of proliferation, but show a slightly decreased serum-half life. In combination the higher activity triggering the receptor more then compensates for the shorter bioavailability in the overall bioactivity. In another example, a shorter half-life and a higher activity towards the receptor triggering are both advantageous. In yet another example the activity in vivo is not improved but the stability in vitro improves the production and storage of the protein molecule composition. In yet another example, a long half-life but a lower activity is needed.

In a preferred embodiment of the invention the increased activity of an antibody molecule composition is an increased ADCC activity. In another preferred embodiment the increased activity of an antibody molecule composition is an increased CDC. In another preferred embodiment the increased activity of an antibody molecule composition is an increased cytotoxicity caused by phagocytosis. In another preferred embodiment the increased activity of an antibody molecule composition is an increased binding activity to the epitope. In another preferred embodiment the increased activity of an antibody molecule composition is an increased binding activity to at least one Fc receptor, preferably FcγRIIIA. In a further preferred embodiment the increased activity of an antibody molecule composition is an increased Fc-mediated cellular cytotoxicity and an increased binding activity to the epitope. In a further preferred embodiment the increased activity of an antibody molecule composition is an increased ADCC activity and an increased binding activity to the epitope. In a further preferred embodiment the increased activity of an antibody molecule composition is an increased ADCC activity, an increased CDC activity, an increased binding activity to the epitope and an increased binding activity to at least one Fc receptor. In a further preferred embodiment the increased activity of an antibody molecule composition is an increased ADCC activity, increased cytotoxicity caused by phagocytosis, an increased binding activity to the epitope and an increased binding activity to at least one Fc receptor. In the most preferred embodiment the increased activity of an antibody molecule composition is an increased ADCC, increased cytotoxicity caused by phagocytosis, an increased CDC activity and an increased binding activity to the epitope and an increased binding activity to at least one Fc receptor.

In accordance with the present invention the term "improved homogeneity" means that an protein/antibody molecule composition of the invention expressed in a host cell of human myeloid leukaemia origin of the invention comprises fewer different glycoforms, or more of a favourable glycoform or of favourable glycoforms, or less of at least one glycoform of an antibody molecule (preferably of those glycoforms which represent at least 1% of the total antibody molecule composition on its own) than at least one antibody molecule composition of the same antibody molecule isolated from at least one of the cell lines CHO, or CHOdhfr−, or BHK, or NS0, or SP2/0, or PerC.6 or mouse hybridoma when expressed therein. In a preferred embodiment of the invention it means that an antibody molecule composition of the invention expressed in a host cell of human myeloid leukaemia origin of the invention comprises fewer different glycoforms, or more of a favourable glycoform or of favourable glycoforms, or less of at least one glycoform of an antibody molecule than an antibody molecule composition of the same antibody molecule isolated from the cell line CHOdhfr− [ATCC No. CRL-9096] when expressed therein.

One heterogeneity particularly problematic for production and use in human is the sialylation. In a preferred embodiment the protein/antibody molecule composition of the invention has an improved homogeneity by comprising no glycoform with the sialic acid N-glycolylneuraminic acid (NeuGc), whereby in this case no glycoform means no glycoform of more than 1% of all carbohydrate chains obtainable from the purified antibody molecule composition and more preferable no carbohydrate chain detectable at all as being detectable by the methods known to those skilled in the art. Since NeuGc is known to be able to be immunogenic in humans this is a large advantage of the host cells of the invention over other production systems such as CHO, NS0, SP2/0.

In a preferred embodiment the protein/antibody molecule composition of the invention has an improved homogeneity in respect to sialylation by comprising less than 5% of glycoforms, more preferably less than 3%, even more preferably less than 1%, and most preferably no glycoforms of the protein/antibody molecule composition with sialic acid detectable as described in examples. In a further preferred embodiment a protein/antibody molecule composition with improved homogeneity in respect to sialylation is achieved by using a host cell of human myeloid leukaemia origin of the invention which has a defect in the sugar nucleotide precursor pathway and therefore is deficient for or has reduced CMP-sialic acid which results in no or a largely reduced sialylation of the carbohydrate sugar chains of the proteins/antibody molecules when the cells are grown in a serum-free medium. In an even further preferred embodiment such protein/antibody molecule composition with improved homogeneity in respect to sialylation can be achieved by using NM-F9 [DSM ACC2606] or NM-D4 [DSM ACC2605] as a host cell of the invention grown in a serum-free medium as and described in more detail in examples.

In another further preferred embodiment a protein/antibody molecule composition with improved homogeneity in respect to sialylation is achieved by using a host cell of human myeloid leukaemia origin of the invention which has a defect in the sugar nucleotide transporter of GMP-sialic acid or in at least one sialyltransferase which results in no or a reduced sialylation of the carbohydrate sugar chains of the proteins/antibody molecules when the cells are grown in a serum-free medium. Examples are NM-F9, NM-D4 and GT-2X.

In another preferred embodiment of the invention the protein/antibody molecule composition with improved homogeneity in respect to sialylation is achieved by using a host cell of human myeloid leukaemia origin of the invention which has an increased sialylation degree. Said sialylation degree means that the amount of the sialic acid N-acetylneuraminic (NeuNc or NeuNAc) on the protein/antibody molecules in an antibody molecule composition is at least 5%, more preferably at least 15%, more preferably at least 20%, more preferably at least 25%, more preferably at least 30%, more preferably at least 35%, more preferably at least 40%, more preferably at least 50%, more preferably at least 60%, more preferably at least 70%, more preferably at least 80%, more preferably at least 90%, more preferably at least 100%, more preferably at least 3 times, more preferably at least 5 times, more preferably at least 10 times, more preferably at least 25 times, more preferably at least 50 times, and most preferably more than 100 times, higher than the amount of sialic acid N-acetylneuraminic (NeuNc or NeuNAc) of the total carbohydrate units or the particular carbohydrate chain at a particular Glycosyaltion site of the protein/antibody molecule when comparing with the same amount of protein/antibody molecules of a protein/antibody molecule composition of the same protein/antibody molecule isolated from at least one of the cell lines CHO, or CHOdhfr−, or BHK, or NS0, or SP2/0, or PerC.6 or mouse hybridoma, preferably CHOdhfr− [ATCC No. CRL-9096] when expressed therein. The sialylation degree can be detected by methods known to those skilled in the art, such as but not limited to immuno blot analysis or ELISA using lectins which binding depends on the sialylation of the carbohydrate structure, such as SNA, MAL, MAL I or PNA, by chemical detection methods such as the thiobarbituric acid method, by HPLC or mass spectrometry or combination thereof. Those skilled in the art can select the most suitable method and adopt and optimise it to the purpose and more details are described in the examples. Preferred is an immunoblot analysis using SNA.

In another further preferred embodiment a protein/antibody molecule composition with improved homogeneity in respect to sialylation is achieved by using a host cell of human myeloid leukaemia origin of the invention, preferably K562, NM-F9 [DSM ACC2606], NM-D4 [DSM ACC2605], NM-E-2F9, NM-C-2F5, NM-H9D8, or NM-H9D8-E6, NM-H9D8-E6Q12, GT-2X and cells or cell lines derived therefrom, and most preferably K562, NM-E-2F9, NM-C-2F5, NM-H9D8, or NM-H9D8-E6, NM-H9D8-E6Q12, GT-2X which has an increased sialylation degree, and results in a protein/antibody molecule composition which comprises alpha 2-6 linked sialic acid, for detectable for example by SNA binding, in a more preferred version the protein/antibody molecule composition comprises alpha 2-6 and alpha 2-3 linked sialic acids.

In another preferred embodiment a protein/antibody molecule composition with improved homogeneity in respect to sialylation is achieved by using a host cell of human myeloid leukaemia origin which comprise at least one sialyltransferase able to attach NeuNAc in alpha 2-3 and at least one sialyltransferase able to attach NeuNAc in alpha 2-6 linkage to sugar groups, such as but not limited to K562, NM-F9 [DSM ACC2606], NM-D4 [DSM ACC2605], NM-E-2F9, NM-C-2F5, NM-H9D8, or NM-H9D8-E6, NM-H9D8-E6Q12, GT-2X and cells or cell lines derived therefrom, thereby resulting in a more preferred composition of glycoforms of the protein/antibody molecule in the protein/antibody molecule composition.

In an even further (preferred) embodiment of the invention said antibody molecule composition of the invention with improved homogeneity in respect to sialylation comprises at least one glycoform of an antibody molecule with at least one carbohydrate chain attached to another glycosylation site of the antibody molecule than the amino acid Asn-297 in the second domain (Cgamma2 domain) of the Fc region.

In an even further preferred embodiment of the former antibody molecule composition with improved homogeneity in respect to sialylation is expressed in a host cell of human myeloid leukaemia origin which has an increased sialylation degree and/or comprise at least one sialyltransferase able to attach sialic acid in alpha 2-3 and at least one sialyltransferase able to attach sialic acid in alpha 2-6 linkage to sugar groups, such as K562, NM-E-2F9, NM-C-2F5, NM-H9D8, or NM-H9D8-E6, NM-H9D8-E6Q12, GT-2X and cells or cell lines derived therefrom.

In an even further preferred embodiment the former antibody molecule has at least one N-glycosylation site (Asn-X-Ser/Thr, whereby X can be any amino acid except Pro) and/or at least one O-glycosylation site in a sequence of the Fab region.

In a further preferred embodiment the antibody molecule composition of the invention with improved homogeneity in respect to sialylation comprising an antibody molecule which comprises at least one carbohydrate chain attached to another glycosylation site of the antibody molecule than the amino acid Asn-297 in the second domain (Cgamma2 domain) of the Fc part has an extended serum-half life and/or bioavailability when measured in at least one mammal such as mice, rats, or preferably in humans, than the antibody molecule composition of the same antibody molecule isolated from at least one of the cell lines CHO, or CHOdhfr−, or BHK, or NS0, or SP2/0, NM-F9, NM-D4 or PerC.6 or mouse hybridoma, preferably the cell line CHOdhfr− [ATCC No. CRL-9096] when expressed therein.

The bioavailability of antibodies can be optimized using the present invention. Expression of antibody molecules in particular in cells having a high or even a very high sialylation (groups 1 and 3 discussed above) can lead to an antibody composition with a prolonged bioavailability, while expression of antibody molecules in the cells of the group 2 may lead to an antibody composition with a comparably shortened bioavailability. The bioavailability can be tested as known by those skilled in the art and as described in the examples using animals or preferably humans. Animals include mice, rats, guinea pigs, dogs, or monkeys but are not restricted to those species. Due to the human nature those animals which have a glycosylation and most important sialylation closest to the human are preferred, most preferred are humans.

In an even more preferred embodiment the antibody molecule composition with improved homogeneity in respect to sialylation is expressed in a host cell of human myeloid leukaemia origin of the invention which has an increased sialylation degree and/or comprise at least one sialyltransferase able to attach sialic acid in alpha 2-3 and at least one sialyltransferase able to attach sialic acid in alpha 2-6 linkage to sugar groups, such as K562, NM-F9 [DSM ACC2606], NM-D4 [DSM ACC2605], NM-E-2F9, NM-C-2F5, NM-H9D8, or NM-H9D8-E6, and cells or cell lines derived therefrom, and comprise at least one carbohydrate chain attached to at least one N-glycosylation site and/or at least one O-glycosylation site in a sequence of the Fab region of the antibody molecule and has an extended serum-half life and/or bioavailability when measured in at least one mammal such as mice, rats, or preferably in humans, than the antibody molecule composition of the same antibody molecule isolated from at least one of the cell lines CHO, or CHOdhfr−, or BHK, or NS0, or SP2/0, or PerC.6 or mouse hybridoma, preferably the cell line CHOdhfr− [ATCC No. CRL-9096] when expressed therein. In a further preferred embodiment the antibody molecule expressed is Erbitux (Cetuximab).

In accordance with the present invention the term "increased yield" means that the average or the maximum yield of a protein/antibody molecule composition of the invention produced in a host cell of human myeloid leukaemia origin is higher than the respective average or maximum yield of at least one protein/antibody molecule composition from the same protein/antibody molecule when expressed in at least one of the cell lines CHO, or CHOdhfr−, or BHK, or NS0, or SP2/0, or PerC.6 or mouse hybridoma. In the preferred embodiment of the invention it means that the average or maximum yield of a protein/antibody molecule composition of the invention expressed in a host cell of human myeloid leukaemia origin is higher than the respective average or maximum yield of a protein/antibody molecule composition from the same protein/antibody molecule when expressed in CHOdhfr− [ATCC No. CRL-9096] using the murine dhfr gene and methotrexate for amplification in CHOdhfr−. The average and maximum yield is measured in SPR, which reflects the productivity of a cell, cell mixture or a cell line, can be determined by those skilled in the art and is described in its preferred embodiment in the examples.

In a further preferred embodiment of the invention at least the average or the maximum yield of a protein/antibody molecule composition of the invention expressed in a host cell of human myeloid leukaemia origin, preferably K562, NM-F9 [DSM ACC2606], NM-D4 [DSM ACC2605], NM-E-2F9, NM-C-2F5, NM-H9D8, or NM-H9D8-E6, NM-H9D8-E6Q12, GT-2X or a cell or cell line derived therefrom, is at least 10% higher than the according of the protein/antibody molecule composition from the same protein/antibody molecule expressed in the cell line CHOdhfr− [ATCC No. CRL-9096] using the murine dhfr gene and methotrexate for amplification in CHOdhfr−, more preferably at least 15%, more preferably at least 20%, more preferably at least 25%, more preferably at least 30%, more preferably at least 35%, more preferably at least 45%, more preferably at least 50%, more preferably at least 55%, more preferably at least 60%, more preferably at least 70%, more preferably at least 80%, more preferably at least 90%, more preferably at least 100%, more preferably at least 3 times, more preferably at least 4 times, and most preferably more than 5 times.

The invention further provides a nucleic acid comprising
(a) a sequence encoding a protein, preferably an antibody molecule or at least one part thereof as described elsewhere herein, and
(b) at least one sequence encoding a sequence from the group of sequence #1 to sequence #9.

In a preferred embodiment of the invention the nucleic acid of the invention comprises
(a) a sequence encoding a protein, preferably an antibody molecule or at least one part thereof as described elsewhere herein, and
(b) a sequence encoding sequence #1.

In a further preferred embodiment of the invention the above described nucleic acid of the invention further comprises a sequence encoding a selection marker, preferably a sequence encoding for a polypeptide which induces an antibiotic resistance of a host cells in which said nucleic acid is introduced, such as but not limited to neomycin or puromycin.

In a further preferred embodiment of the invention the above described nucleic acid of the invention further comprises at least one sequence of at least one genetic element described elsewhere herein.

The invention further provides a host cell of human myeloid leukaemia origin or any human myeloid or myeloid precursor cell or cell line which can be obtained from a leukaemia patient, or any myeloid or myeloid precursor cell or cell line which can be obtained from a human donor or a mixture of cells or cell lines comprising at least one cell of human myeloid leukaemia origin, or cell, cells, or cell line which was obtained by fusing at least one cell, cells, or a cell line of human myeloid leukaemia origin or any human myeloid or myeloid precursor cell or cell line which can be obtained from a leukaemia patient, or any myeloid or myeloid precursor cell or cell line which can be obtained from a human donor, with another cell of human or animal origin, such as but not limited to B cells, CHO cells, comprising at least one nucleic acid encoding a protein/antibody molecule or parts thereof which was introduced into said cells.

The invention provides a host cell of the invention described above comprising at least one nucleic acid encoding a protein/antibody molecule or at least one part thereof.

In a preferred embodiment the invention provides the host cell K562, NM-F9 [DSM ACC2606], NM-D4 [DSM ACC2605], NM-E-2F9, NM-C-2F5, NM-H9D8, or NM-H9D8-E6, NM-H9D8-E6Q12, GT-2X or a cell or cell line derived from anyone of said host cells, preferably those which grows under serum-free conditions and from which a protein/antibody molecule composition is isolated under serum-free conditions, and even more preferred those into which the nucleic acid encoding the antibody molecule was introduced under serum-free conditions, comprising at least one nucleic acid encoding a protein/antibody molecule or parts thereof, preferably a nucleic acid comprising a sequence encoding a protein/antibody molecule or at least one part thereof as described elsewhere herein.

The invention provides a host cell of the invention described above comprising at least one nucleic acid encoding at least one polypeptide of the group of sequence #1 to sequence #9, preferably sequence #1.

The invention provides a host cell of the invention described above comprising at least one nucleic acid encoding an antibody molecule or parts thereof and at least one nucleic acid encoding at least one polypeptide of the group of sequence #1 to sequence #9, preferably sequence #1.

In a preferred embodiment the invention provides the host cell K562, NM-F9 [DSM ACC2606], NM-D4 [DSM ACC2605], NM-E-2F9, NM-C-2F5, NM-H9D8, or NM-H9D8-E6, NM-H9D8-E6Q12, GT-2X or a cell or cell line derived from anyone of said host cells, preferably those which grows under serum-free conditions and from which a protein/antibody molecule composition is isolated under serum-free conditions, and even more preferred those into which the nucleic acid encoding the protein/antibody molecule was introduced under serum-free conditions, comprising at least one nucleic acid encoding a protein/antibody molecule or parts thereof, preferably a nucleic acid comprising a sequence encoding a protein/antibody molecule or at least one part thereof as described elsewhere herein, and at least one sequence encoding a sequence from the group of sequence #1 to sequence #9, preferably sequence #1.

In a further preferred embodiment the invention provides the above described host cells wherein the antibody molecule encoded is an antibody of WO2004/065423.

In an even further preferred embodiment the invention provides the above described host cells wherein the antibody molecule encoded is the antibody PankoMab [Cancer Immunol Immunother. 2006 November; 55(11):1337-47. Epub 2006 February PankoMab: a potent new generation antitumour MUC1 antibody. Danielczyk et al], preferably a chimaeric form of PankoMab with all human constant domains, and more preferably a humanized PankoMab.

The invention further provides a protein/antibody molecule composition having increased activity and/or increased yield and/or improved homogeneity and fully human glycosylation produced by any of the methods of the invention as described somewhere herein.

In a preferred embodiment the invention provides a protein/antibody molecule composition produced by any of the methods of the invention has an increased activity and/or increased yield and/or improved homogeneity and fully human glycosylation produced by any of the methods of the invention when compared to a protein/antibody molecule composition of the same protein/antibody molecule isolated from at least one of the cell lines CHO, or CHOdhfr–, or BHK, or NS0, or SP2/0, or PerC.6 or mouse hybridoma, preferably CHOdhfr– [ATCC No. CRL-9096], when expressed therein.

The protein molecule or part thereof expressed can be any protein or protein part or protein fragment. The antibody molecule or part thereof expressed can be any antibody or antibody part or antibody fragment.

Protein molecule compositions of the present invention can be used for prophylactic and/or therapeutic treatment of diseases, such as leukemia, neutropenia, cytopenia, cancer, bone marrow transplantation, diseases of hematopoietic systems, infertility and autoimmune diseases. The spectrum of therapeutic applications known to people of the field of art, of protein molecule compositions is very wide. For example, G-CSF is an important therapeutic to treat neutropenia, a life-threatening decrease in neutrophils as consequence of a chemotherapy of leukemic cancer patients. GM-CSF is specifically used for treatment of AML patients at relative high age after chemotherapy to achieve a fast recovery from neutropenia. GM-CSF is additionally approved as therapeutic for several applications in bone marrow transplantations and for mobilization of peripheral blood stem cells. In addition, there are several clinical applications of GM-CSF that are currently under investigation, such as for treatment of HIV and cancer. Certain diseases of the hematopoietic system are treated with EPO, and IFN-beta is currently an important therapeutic for treatment of multiple sclerosis, an autoimmune disease. Another example is FSH which is widely used for treatment of male and female infertility. hCG is also applied for the treatment of infertility, but focusing on the anovulation in women. hGH has clinically-proven benefits, such as bodyfat reduction and muscle tissue increase.

Protein molecule compositions of the present invention can also be used for the manufacture of a medicament for prophylactic and/or therapeutic treatments of diseases selected from the group comprising leukemia, neutropenia, cytopenia, cancer, bone marrow transplantation, diseases of hematopoietic systems, infertility and autoimmune diseases.

In a preferred embodiment of the invention the antibody molecule expressed is an antibody molecule recognizing psoriasis, rheumatoid arthritis, Crohn's disease, ulcerative colitis, autoimmune diseases, SLE, Multiple Sclerosis, autoimmune haematological disorders, asthma, allergy, graft-versus-host disease, allograft rejection, glaucoma surgery, myocardial infarction, viruses as RSV, HIV, Hep B, or CMV, cancer, sarcoma, CLL, AML, or NHL.

In an even preferred embodiment of the invention the antibody molecule expressed is an antibody molecule recognizing the cancer, tumor or metastasis, at least one cancer cell or tumor cell, in at least one human, preferably selected from the group of cancerous diseases or tumor diseases of the ear-nose-throat region, of the lungs, mediastinum, gastrointestinal tract, urogenital system, gynecological system, breast, endocrine system, skin, bone and soft-tissue sarcomas, mesotheliomas, melanomas, neoplasms of the central nervous system, cancerous diseases or tumor diseases during infancy, lymphomas, leukemias, paraneoplastic syndromes, metastases with unknown primary tumor (CUP syndrome), peritoneal carcinomatoses, immunosuppression-related malignancies and/or tumor metastases.

In a preferred embodiment of the invention the expressed antibody or part thereof is an anti MUC1 antibody.

In a further preferred embodiment of the invention the antibody molecule encoded by the nucleic acid or nucleic acids of the invention is the antibody Rituximab, Herceptin, Erbitux, Campath 1H or antibodies derived therefrom.

In an even more preferred embodiment of the invention the antibody molecule encoded by the nucleic acid or nucleic acids of the invention is an antibody of WO2004/050707, and even more preferred of WO2004/065423, and even more preferred PankoMab [Cancer Immunol Immunother. 2006 November; 55(11):1337-47. Epub 2006 February PankoMab: a potent new generation anti-tumour MUC1 antibody. Danielczyk et al], and even more preferred a chimaeric version thereof comprising all human constant domains, and even more preferred a humanized antibody thereof.

In an even more preferred embodiment of the invention the antibody molecule encoded by the nucleic acid or nucleic acids of the invention is any whole antibody of the invention, preferably Rituximab, Herceptin, Erbitux, more preferably WO2004/065423, most preferably PankoMab, whereby the antibody molecule composition isolated from any host cell of the invention, preferably K562, NM-F9 [DSM ACC2606], NM-D4 [DSM ACC2605], NM-E-2F9, NM-C-2F5, NM-H9D8, or NM-H9D8-E6, NM-H9D8-E6Q12, GT-2X or a cell or cell line derived from anyone of said host cells, comprises no detectable NeuGc. The same applies to proteins in general.

In an even more preferred embodiment of the invention the antibody molecule encoded by the nucleic acid or nucleic acids of the invention is any whole antibody molecule or an antibody molecule comprising the Cgamma2 domain of the invention, preferably Rituximab, Herceptin, Erbitux, more preferably WO2004/065423, most preferably PankoMab, whereby the antibody molecule composition isolated from a host cell of the invention, preferably K562, NM-F9 [DSM ACC2606], NM-D4 [DSM ACC2605], NM-E-2F9, NM-C-2F5, NM-H9D8, or NM-H9D8-E6, NM-H9D8-E6Q12, GT-2X or a cell or cell line derived from anyone of said host cells, comprises at least one glycoform with alpha 2-6 sialic acid. The same applies to proteins in general.

In an even more preferred embodiment of the invention the antibody molecule encoded by the nucleic acid or nucleic acids of the invention is any whole antibody molecule or an antibody molecule comprising the Cgamma2 domain of the invention, preferably Rituximab, Herceptin, Erbitux, Campath 1H, more preferably WO2004/065423, most preferably PankoMab, whereby the antibody molecule composition isolated from host cell NM-E-2F9, NM-C-2F5, NM-H9D8, or NM-H9D8-E6, NM-H9D8-E6Q12, GT-2X or a cell or cell line derived from anyone of said host cells, comprises alpha 2-6 sialic acid, which is detectable by immune blot analysis with the lectin SNA as described in examples. The same applies to proteins in general.

In another preferred embodiment of the invention the antibody molecule encoded by the nucleic acid or nucleic acids of the invention is any antibody molecule, preferably Rituximab, Herceptin, Erbitux, Campath 1H, more preferably WO2004/065423, most preferably PankoMab, and the antibody molecule composition isolated from the host cell NM-F9 or NM-D4 of the invention after cultivation in serum-free and more preferably protein-free medium has an improved homogeneity with no detectable sialic acids. The same applies to proteins in general.

In a further preferred embodiment of the invention the antibody molecule encoded by the nucleic acid or nucleic acids of the invention is the antibody Rituximab, Herceptin, Campath 1H, or antibodies derived therefrom, and the antibody molecule composition isolated from the host cell of the invention has an increased ADCC activity of at least 4 fold higher than the activity of the antibody molecule composition from the same antibody molecule expressed in the cell line CHOdhfr− [ATCC No. CRL-9096].

In an even more preferred embodiment of the invention the antibody molecule encoded by the nucleic acid or nucleic acids of the invention is an antibody of WO2004/065423, more preferably PankoMab, and the antibody molecule composition isolated from the host cell of the invention has an increased ADCC activity of at least 4 fold higher when produced in at least one of the cells K562, NM-F9 [DSM ACC2606], NM-D4 [DSM ACC2605], NM-E-2F9, NM-C-2F5, NM-H9D8, or NM-H9D8-E6, NM-H9D8-E6Q12, GT-2X or a cell or cell line derived from anyone of said host cells than the activity of the antibody molecule composition from the same antibody molecule expressed in the cell line CHOdhfr− [ATCC No. CRL-9096].

In another preferred embodiment of the invention the antibody molecule encoded by the nucleic acid or nucleic acids of the invention is an antibody of WO2004/065423, more preferably PankoMab, and the antibody molecule composition isolated from the host cell of the invention K562, NM-F9 [DSM ACC2606], NM-D4 [DSM ACC2605], NM-E-2F9, NM-C-2F5, NM-H9D8, or NM-H9D8-E6, NM-H9D8-E6Q12, GT-2X or a cell or cell line derived from anyone of said host cells has an increased binding activity to its epitope of at least 50% higher, preferably 2 fold higher than the activity of the antibody molecule composition from the same antibody molecule expressed in the cell line CHOdhfr− [ATCC No. CRL-9096].

In another preferred embodiment of the invention the antibody molecule encoded by the nucleic acid or nucleic acids of the invention is an antibody of WO2004/065423, more preferably PankoMab, and the antibody molecule composition isolated from the host cell NM-F9 or NM-D4 of the invention after cultivation in serum-free and more preferably protein-free medium has an improved homogeneity with no detectable sialic acids. The same applies to proteins in general.

In another preferred embodiment of the invention the antibody molecule encoded by the nucleic acid or nucleic acids of the invention is an antibody of WO2004/065423, more preferably PankoMab, and the antibody molecule composition isolated from the host cell K562, NM-F9 [DSM ACC2606], NM-D4 [DSM ACC2605], NM-E-2F9, NM-C-2F5, NM-H9D8, or NM-H9D8-E6, NM-H9D8-E6Q12, GT-2X or a cell or cell line derived from anyone of said host cells has an improved homogeneity with at least 10% more sialic acids than the antibody molecule composition from the same antibody molecule expressed in the cell line CHOdhfr− [ATCC No. CRL-9096]. The same applies to proteins in general.

In another preferred embodiment of the invention the antibody molecule encoded by the nucleic acid or nucleic acids of the invention is an antibody of WO2004/065423, more preferably PankoMab, and the antibody molecule composition isolated from the host cell of the invention has an improved homogeneity with a higher degree of no detectable sialic acids when expressed in NM-F9 or NM-D4 when compared to an antibody molecule composition from the same antibody molecule expressed in the cell line CHOdhfr− [ATCC No. CRL-9096]. The same applies to proteins in general.

In another preferred embodiment of the invention the antibody molecule encoded by the nucleic acid or nucleic acids of the invention is an antibody of WO2004/065423, more preferably PankoMab, and the antibody molecule composition isolated from the host cell of the invention has an improved homogeneity as described above, and an increased ADCC activity of at least 4 fold higher than the activity of the antibody molecule composition from the same antibody molecule expressed in the cell line CHOdhfr− [ATCC No. CRL-9096].

In the most preferred embodiment of the invention the antibody molecule encoded by the nucleic acid or nucleic acids of the invention is an antibody of WO2004/065423, more preferably PankoMab.

The invention further provides a host cell for producing a protein/antibody molecule composition having increased activity and/or increased yield and/or improved homogeneity and fully human glycosylation in sense of the invention as described elsewhere herein, wherein the host cell is any cell, cells, or cell line of human myeloid leukaemia origin or any human myeloid or myeloid precursor cell or cell line which can be obtained from a leukaemia patient, or any myeloid or myeloid precursor cell or cell line which can be obtained from a human donor or a mixture of cells or cell lines comprising at least one cell of human myeloid leukaemia origin, or a cell or cell line derived therefrom as described elsewhere herein, or a mixture of cells or cell lines comprising at least one of those aforementioned cells.

The invention also provides a host cell for producing a protein/antibody molecule composition having increased activity and/or increased yield and/or improved homogeneity and fully human glycosylation in sense of the invention as described elsewhere herein, wherein the host cell is any cell, cells, or cell line which was obtained by fusing at least one cell, cells, or a cell line of human myeloid leukaemia origin or any human myeloid or myeloid precursor cell or cell line which can be obtained from a leukaemia patient, or any myeloid or myeloid precursor cell or cell line which can be obtained from a human donor, with another cell of human or animal origin, such as but not limited to B cells, CHO cells.

In a preferred embodiment said host cell the invention provides for producing a protein/antibody molecule composition having increased activity and/or increased yield and/or improved homogeneity in sense of the invention as described elsewhere herein, is the cell or cell line KG1, MUTZ-3, K562, NM-F9 [DSM ACC2606], NM-D4 [DSM ACC2605], NM-E-2F9, NM-C-2F5, NM-H9D8, or NM-H9D8-E6, NM-H9D8-E6Q12, GT-2X or a cell or cell line derived therefrom, or a mixture of cells or cell lines comprising at least one of those aforementioned cells.

In a further preferred embodiment said host cell the invention provides for producing a protein/antibody molecule composition having increased activity and/or increased yield and/or improved homogeneity in sense of the invention as described elsewhere herein, is the cell or cell line K562, NM-F9 [DSM ACC2606], NM-D4 [DSM ACC2605], NM-E-2F9, NM-C-2F5, NM-H9D8, or NM-H9D8-E6, NM-H9D8-E6Q12, GT-2X or a cell or cell line derived therefrom.

In a further preferred embodiment said host cell the invention provides for producing a protein/antibody molecule composition having increased activity and/or increased yield and/or improved homogeneity in sense of the invention as described elsewhere herein, is the cell or cell line NM-F9 [DSM ACC2606], NM-D4 [DSM ACC2605], NM-E-2F9, NM-C-2F5, NM-H9D8, or NM-H9D8-E6, NM-H9D8-E6Q12, GT-2X or a cell or cell line derived therefrom or a cell or cell line derived therefrom as described elsewhere herein.

In an even further preferred embodiment said host cell the invention provides for producing a protein/antibody molecule composition having increased activity and/or increased yield and/or improved homogeneity in sense of the invention as described elsewhere herein, is a cell or a cell line derived from KG1, MUTZ-3, K562, NM-F9 [DSM ACC2606], NM-D4 [DSM ACC2605], NM-E-2F9, NM-C-2F5, NM-H9D8, or NM-H9D8-E6, NM-H9D8-E6Q12, GT-2X or a cell or cell line derived therefrom as described elsewhere herein, which grows under serum-free conditions, and preferably those in which the nucleic acid encoding the protein/antibody molecule can be introduced in these cells and an antibody molecule composition is isolated under serum-free conditions.

In an even further preferred embodiment said host cell the invention provides for producing a protein/antibody molecule composition having increased activity and/or increased yield and/or improved homogeneity in sense of the invention as described elsewhere herein, is a cell or a cell line derived from K562, NM-F9 [DSM ACC2606], NM-D4 [DSM ACC2605], NM-E-2F9, NM-C-2F5, NM-H9D8, or NM-H9D8-E6, NM-H9D8-E6Q12, GT-2X or a cell or cell line derived therefrom as described elsewhere herein, which grows under serum-free conditions.

In an even further preferred embodiment said host cell the invention provides for producing a protein/antibody molecule composition having increased activity and/or increased yield and/or improved homogeneity in sense of the invention as described elsewhere herein, is a cell or a cell line derived from K562, NM-F9 [DSM ACC2606], NM-D4 [DSM ACC2605], NM-E-2F9, NM-C-2F5, NM-H9D8, or NM-H9D8-E6, NM-H9D8-E6Q12, GT-2X or a cell or cell line derived therefrom as described elsewhere herein, which grows under serum-free conditions and in which the nucleic acid encoding the protein/antibody molecule can be introduced in these cells and a protein/antibody molecule composition is isolated under serum-free conditions.

In the most preferred embodiment said host cell the invention provides for producing a protein/antibody molecule composition having increased activity and/or increased yield and/or improved homogeneity in sense of the invention as described elsewhere herein, is the cell or cell line NM-F9 [DSM ACC2606], NM-D4 [DSM ACC2605], NM-E-2F9, NM-C-2F5, NM-H9D8, or NM-H9D8-E6, NM-H9D8-E6Q12, GT-2X or a cell or cell line derived therefrom as described elsewhere herein, which grows under serum-free conditions, and preferably those in which the nucleic acid encoding the protein/antibody molecule can be introduced in these cells and the protein/antibody molecule composition is isolated under serum-free conditions.

The invention further provides a protein/protein composition isolated by any of the methods of the invention described elsewhere herein.

The invention further provides a protein molecule composition isolated by any of the methods of the invention described elsewhere herein which has an increased activity and/or increased yield and/or improved homogeneity and fully human glycosylation in sense of the invention and described elsewhere herein.

In a further preferred embodiment of the invention the protein molecule or part thereof has a size of at least 10 kDa, preferably a size of at least 15 kDa, more preferably a size of at least 20 kDa, more preferably a size of at least 25 kDa, more preferably a size of at least 30 kDa, more preferably a size of at least 35 kDa, more preferably a size of at least 40 kDa, more preferably a size of at least 45 kDa, more preferably a size of at least 50 kDa, more preferably a size of at least 55 kDa, more preferably a size of at least 60 kDa, more preferably a size of at least 65 kDa, more preferably a size of at least 70 kDa, more preferably a size of at least 75 kDa, more preferably a size of at least 80 kDa, more preferably a size of at least 85 kDa, more preferably a size of at least 90 kDa, more preferably a size of at least 95 kDa, more preferably a size of at least 100 kDa, more preferably a size of at least 105 kDa, more preferably a size of at least 110 kDa, more preferably a size of at least 115 kDa, more preferably a size of at least 120 kDa, more preferably a size of at least 125 kDa, more preferably a size of at least 130 kDa, more preferably a size of at least 135 kDa, more preferably a size of at least 140 kDa, more preferably a size of at least 145 kDa, more preferably a size of at least 150 kDa, more preferably a size of at least 155 kDa, more preferably a size of at least 160 kDa, more preferably a size of at least 165 kDa, more preferably a size of at least 170 kDa, more preferably a size of at least 175 kDa, more preferably a size of at least 180 kDa, more preferably a size of at least 185 kDa, more preferably a size of at least 190 kDa, more preferably a size of at least 195 kDa, most preferably a size of at least 200 kDa.

In a preferred embodiment of the invention said protein molecule composition originates from any of the protein molecule of the group of cytokines and their receptors, for instance the tumor necrosis factors TNF-alpha and TNF-beta; renin; human growth hormone and bovine growth hormone; growth hormone releasing factor; parathyroid hormone; thyroid stimulating hormone; lipoproteins; alpha-1-antitrypsin; insulin A-chain and B-chain; gonadotrophins, e.g. follicle stimulating hormone (FSH), luteinizing hormone (LH), thyrotrophin, and human chorionic gonadotrophin (hCG); calcitonin; glucagon; clotting factors such as factor VIIIC, factor IX, factor VII, tissue factor and von Willebrands factor; anti-clotting factors such as protein C; atrial natriuretic factor; lung surfactant; plasminogen activators, such as urokinase, human urine and tissue-type plasminogen activator; bombesin; thrombin; hemopoietic growth factor; enkephalinase; human macrophage inflammatory protein; a serum albumin such as human serum albumin; mullerian-inhibiting substance; relaxin A-chain and B-chain; prorelaxin; mouse gonadotropin-associated peptide; vascular endothelial growth factor; receptors for hormones or growth factors; integrin; protein A and D; rheumatoid factors; neurotrophic factors such as bone-derived neurotrophic factor, neurotrophin-3, -4, -5, -6 and nerve growth factor-beta; platelet-derived growth factor; fibroblast growth factors; epidermal growth factor; transforming growth factor such as TGF-alpha and TGF-beta; insulin-like growth factor-I and -II; insulin-like growth factor binding proteins; CD proteins such as CD-3, CD-4, CD-8 and CD-19; erythropoietin (EPO); osteoinductive factors; immunotoxins; a bone morphogenetic protein; an interferon such as interferon-alpha, -beta, and -gamma; colony stimulating factors (CSF's), e.g. M-CSF, GM-CSF and G-CSF; interleukins (IL's), e.g. IL-1 to IL-12; superoxide dismutase; T-cell receptors; surface membrane proteins; decay accelerating factor; antibodies and immunoadhesins; Glycophorin A; MUC1.

In a more preferred embodiment of the invention said protein molecule composition originates from any of the protein molecule of the group of Glycophorin A, EPO, G-CSF, GM-CSF, FSH, hCG, LH, interferons, interleukins, antibodies and/or fragments thereof.

Also provided is a glycol protein or protein composition obtainable by the production methods according to the present invention. Said protein preferably has the glycosylation characteristics as defined in claim 27.

Preferably, said protein composition is an antibody molecule composition. The invention further provides an antibody molecule composition isolated by any of the methods of the invention described elsewhere herein which has an increased activity and/or increased yield and/or improved homogeneity in sense of the invention and described elsewhere herein.

Examples of such antibodies include antibodies against ganglioside GD3, human interleukin-5 receptor alpha-chain, HER2, CC chemokine receptor 4, CD20, CD22, neuroblastoma, MUC1, epidermal growth factor receptor (EGFR).

In a preferred embodiment of the invention said antibody molecule composition originates from any of the antibody molecule of the group of Muromomab, Daclizumab, Basiliximab, Abciximab, Rituximab, Herceptin, Gemtuzumab, Alemtuzumab, Ibritumomab, Cetuximab (Erbitux), Bevacizumab, Tositumomab, Pavlizumab, Infliximab, Eculizumab, Epratuzumab, Omalizumab, Efalizumab, Adalimumab, Campath-1H, C2B8, Panorex, BrevaRex, Simulect, Antova, OKT3, Zenapax, ReoPro, Synagis, Ostavir, Protovir, OvaRex, Vitaxin.

In a more preferred embodiment of the invention said antibody molecule composition originates from any of the antibody molecule of the group of Rituximab, Herceptin, anti-CC chemokine receptor 4 antibody KM2160, Campath-1H, C2B8, Erbitux, anti-neuroblastoma antibody chCE7. In an even more preferred embodiment of the invention said antibody molecule composition originates from the antibody molecule of the group of WO2004/065423, more preferably PankoMab, more preferably its chimaeric and even more preferably its humanized form.

Also provided is a protein or protein composition obtainable by the production method of the present invention, wherein the protein is an antibody which binds to the MUC1 epitope, comprising the amino acid sequence DTR.

MUC-1 is an established tumor marker expressed on a variety of epithelial tumours and is a potential tumor target. MUC-1 is a large, highly 0-glycosylated transmembrane glycoprotein. The extracellular portion consists of a variable number of 20 to 120 tandem repeats (TR), each of which consists of 20 amino acids with five potential O-glycosylation sites. MUC 1 is not only expressed on epithelial tissues but also on haematopoietic cells. Several antibodies are known which bind the DTR motif of MUC 1 which are also suitable proteins/antibodies in the context of the present invention (for an overview see Karsten et al, 1998). Karsten also described a novel carbohydrate induced conformational epitope on MUC 1 (TA MUC) of the structure . . . PDT* RP . . . (SEQ ID NO: 22) where T* is O glycosylated. The glycans present at this site are themselves tumour-specific carbohydrate structures.

Hence, it is desirable to use a MUC antibody which can discriminate between the TA MUC tumour epitope and the non-glycosylated epitope. One suitable antibody able to specifically recognize the glycosylated TA MUC epitope is the PankoMab antibody. His production is described in detail in Danielczyk et al 2006, herein fully incorporated by reference (PankoMab: a potent new generation anti-tumor MUC-1 antibody). The antibody PankoMab or a variant thereof, competitively binding the same TA-MUC 1 epitope as the parent PankoMab antibody is preferably used. Such an antibody variant has at least one of the following characteristics:
- it binds an epitope comprising at least the amino acid sequence PDTRP (SEQ ID NO: 22);
- it binds to a short MUC peptide of 30 amino acids comprising 1,5 TRs when it is glycosylated with GalNAcalpha at the PDTRP sequence (SEQ ID NO: 22) but not if the same peptide is not glycosylated;
- it shows an additive length effect of more than 25, preferably 28 (most preferably a ratio of 29.5);
- it depicts a low or even no binding to cells of the haematopoietic system (regarding the detection method, please see Danielczyk et al 2006, herein incorporated by reference);
- it has a high affinity towards tumour cells ranging from approximately at least $K_{ass}=0.2-1\times10^9 M^{-1}$ as determined by Scatchard plot analyses.

Suitable examples of respective variants are given in the examples. The antibody can be of murine, origin, chimeric or humanised.

The antibody binding the TA-MUC 1 epitope, preferably the PankoMab antibody or the antibodies Panko 1 and Panko 2 as described herein, has at least one of the following glycosylation characteristics:
- (i) it has an increased sialylation degree with at least a 15% higher amount of N-acetylneuraminic acid on the total carbohydrate structures or on the carbohydrate structures at one particular glycosylation site of the antibody molecule of the antibody molecules in said antibody molecule composition than the same amount of antibody molecules of at least one antibody molecule composition of the same antibody molecule isolated from CHOdhfr− [ATCC No. CRL-9096] when expressed therein;
- (ii) it has a higher galactosylation degree with at least a 5% higher amount of G2 structures on the total carbohydrate structures or on the carbohydrate structures at one particular glycosylation site of the antibody molecule of the antibody molecules in said antibody molecule composition than the same amount of antibody molecules of at least one antibody molecule composition of the same antibody molecule isolated from CHOdhfr− [ATCC No. CRL-9096] when expressed therein;
- (iii) it comprises a detectable amount of bisecGlcNAc;
- (iv) it has no or less than 2% hybrid or high mannose structures.

A respective glycosylation pattern results in the following surprising and beneficial activity pattern:
- (i) a CDC activity which is more than 15% higher than the activity of the same antibody expressed in CHO cells;
- (ii) a serum half life which is elongated by factor 2 (more than 1.5) compared to an antibody which carries no detectable sialylation;
- (iii) it has an increased Fc-mediated cellular cytotoxicity which is at least 2 times higher than the Fc-mediated cellular cytotoxicity of at least one antibody molecule composition from the same antibody molecule when expressed in the cell line CHOdhfr− [ATCC No. CRL-9096].

A respective antibody can be obtained by producing it in cell lines according to the present invention which provide a high sialylation and galactosylation degree, but preferably a lower fucosylation. Suitable examples are NM-H9D8 and NM-H9D8-E6.

EXAMPLE 1

Analyses of Fut8 Expression in Cells

RNA was extracted from NM-F9 [DSM ACC2606], NM-D4 [DSM ACC2605], NM-H9, K562, NM-H9D8 [DSM ACC2806], GT-2x [DSM ACC2858] and HepG2 (control) cells according to standard procedures (RNeasy-Mini-Kit, Qiagen). The mRNA was isolated using magnetic beads technology according to manufacturers instruction (HDynabeads® Oligo(dT)25H, Invitrogen) For the first-strand$P^P$ cDNA synthesis, 50 µl bead suspension of each sample and Omniscript Reverse Transcriptase (Qiagen) were used according to manufacturers instructions. For the subsequent$P^F$RT-PCR reaction 5 µl of the cDNA product $P^P$ an d specific fut8 primers were used resulting in a 212 bp fragment. As a control actin specific primers were used resulting in 240 bp fragment. The resulting PCR-product(s) $P^P$ were analysed on a 1.5% gel.

NM-F9, NM-D4, NM-H9, K562, NM-H9D8 and GT-2x do express the mRNA for fut8.

FIG. 1 shows as an example the fut8 mRNA expression of NM-F9, NM-D4, and NM-H9D8.

EXAMPLE 2

Glycoengineering of K562 Cells

Glycoengineering of K562 cells and generation of NM-D4 and NM-F9 cell line are described in EP1654353.

NM-H9 cells, and a cell or cell line derived therefrom with high sialylation potential were generated as follows. Random mutagenesis was performed by treating K562 cells with the alkylating agent ethyl methanesulfonate. Per sample K562 cells were washed in PBS and seeded at $10P^{6P}$ cells per ml cell culture medium supplemented with EMS (0.1 mg/ml, ethyl methanesulfonate, Sigma-Aldrich) overnight at 37° C. and 5% $COB_{2B}$. Cells were washed and provided with fresh medium. Every second day cell vitality was determined by trypan blue staining, and cells were analysed by immunocytochemical staining.

Subsequently, cells exposing the novel phenotype of high TF expression were selected by means of a TF-specific antibody. K562 cells were washed in B-PBS (0.5% BSA in PBS), incubated with 50 µl of supernatant of hybridoma cultures of the monoclonal antibody A78-G/A7 or PankoMab and 950 µl of B-PBS at 4° C. for 30 min. After washing the procedure was repeated with 50 µl of rat-antimouse-IgM-antibody or rat-anti-mouse-IgG-antibody conjugated with MicroBeads (Miltenyi Biotec, Köln, Germany). After washing the magnetically labelled TF-positive K562 cells were separated by two successive columns provided by Miltenyi Biotec (Köln, Germany) as described in the manufacturers manual. Following nine days of cultivation, the isolation procedure was repeated in total three times. FACS analysis (flow cytometry) started with antibody staining: About $3 \times 10^5$ cells were incubated at 4° C. for 1.5 h with primary monoclonal antibody (hybridoma culture supernatants of A78-G/A7 (IgM), PankoMab (IgG1), all diluted 1:2 in cell culture medium) followed by the secondary Cy3-conjugated goat anti-mouse IgM or IgG antibody 1:200 diluted in PBS, at 4° C. for 30 min and were washed again. Resuspended cells (200 µl PBS) were investigated by flow cytometry (flow cytometer: Coulter Epics, Beckman Coulter, Krefeld, Ger). Quantitative analyses were carried out using the Expo32 software (Becton Coulter) with following parameter for antibody labelled cells: forward scatter (FS): 26 V, gain 1, sideward scatter (SS): 807 V, gain 5, FL2: 740 V, gain 1, and following parameter for lectin labeled cells: FS: 26 V, gain 1, SS: 807 V, gain 5, FL1:740 V, gain 1).

After three rounds of isolation a K562 cell population of 93% TF-positive cells was received. However, the percentage of TF-positive K562 cells decreased over time reaching a bottom level of about 20% TF-positive cells during a period of 14 days following the isolation procedure. For stable expression of the TF-positive phenotype, K562 cells were isolated for a forth time and finally, the isolated TF-positive K562 cells were cloned thereafter by limited dilution in 96-well plates (1 cell/100 µl). Among thirty K562 cell clones that were obtained, seventeen cell clones expressed low amounts of the TF antigen or no TF antigen. These cell clones were analysed for SNA binding in flow cytometry and for proliferation rates (analysis of doubling time see below). Cell clones showing high SNA binding and high proliferation rate were selected. Stable NM-H9 clone was selected for further clone development by single cell cloning and to optimise growth under serum-free conditions. As the most preferred cell clone NM-H9D8 [DSM ACC2806] was selected and deposited under DSM ACC2806 at the "DSMZ-Deutsche Sammlung von Mikroorganismen and Zellkulturen GmbH" in Braunschweig (Germany), by Glycotope GmbH, Robert-Rössle-Str. 10, 13125 Berlin (Germany) at the Sep. 15, 2006.

EXAMPLE 3

Cultivation of K562, NM-F9, NM-D4, NM-H9, NM-E-2F9, NM-C-2F5, NM-H9D8, NM-H9D8-E6, NM-H9D8-E6Q12, and GT-2x Cell Lines and CHOdhfr− Cells and Generation of Serum Free Cell Lines K562, NM-F9, NM-D4, NM-H9, NM-E-2F9, NM-C-2F5, NM-H9D8 [DSM ACC2806], NM-H9D8-E6 [DSM ACC2807], NM-H9D8-E6Q12 [DSM ACC2856], or GT-2x [DSM ACC2858] were cultured in RPMI 1640 supplemented with 10% FCS and 2 mM glutamine or serum free in X-Vivo 20 medium and grown at 37° C. in a humidified atmosphere of 8%.

CHOdhfr− cells (ATCC No. CRL-9096) were cultured in DMEM supplemented with 10% FCS, 2 mM glutamine, and 2% HT supplement or serum free in CHO-S-SFM II medium and grown at 37° C. in a humidified atmosphere of 8%.

K562, NM-F9, NM-D4, NM-H9, NM-E-2F9, NM-C-2F5, NM-H9D8 [DSM ACC2806], NM-H9D8-E6 [DSM ACC2807], NM-H9D8-E6Q12 [DSM ACC2856], or GT-2x [DSM ACC2858] and cell or cell line derived from said host cells are easily adapted to serum free conditions by a complete change of cell culture medium. Cells and cell lines according to the present invention are inoculated into a serum-free medium as X-Vivo 20 at a density of $1 \times 10^5$ to $5 \times 10^5$ cells/ml, preferably $2 \times 10^5$ cells/ml, and cultured by an ordinary culturing method for animal cells. After 4 to 7 days of culturing, the cells whose density reached $5 \times 10^5$ to $10 \times 10^5$ cells/ml are selected as the cells adapted to a serum-free medium. Adaptation to serum-free media can be also performed by successive dilution of the medium supplemented with FCS by a serum-free medium composition (continuous adaptation). Productivity of converted FCS production clones of antibody composition producing host cells of the present invention to serum free conditions is mostly preserved.

Adaptation of CHOdhfr− (ATCC No. CRL-9096) to serum free conditions has to be performed stepwise and takes several weeks whereby a lost of productivity of at least a half is usual.

EXAMPLE 4

Cloning of Vectors to Express the Chimeric Antibodies PankoMab, Panko1, Panko2, or Cetuximab in Eukaryotic Cells Variable sequences of PankoMab were PCR amplified with specific primers from the murine hybridoma cells producing PankoMab [HCancer Immunol Immunother. H 2006 November; 55(11):1337-47. Epub 2006 February PankoMab: a potent new generation anti-tumour MUC1 antibody. Danielczyk et al].

Variable sequences VH and VL of Panko1 and Panko2 are described in WO2004/065423, herein incorporated by reference.

```
Variable Heavy chain of Panko1:
                                    (SEQ ID NO: 11)
EVKLVESGGGLVQPGGSMKLSCAASGFTFSDAWMDWVRQSPEKGLEWVAE

IRSKANNHATYYAESVKGRFTISRDVSKSSVYLQMNNLRAEDTGIYYCTR

GGYGFDYWGQGTTLTVS.

Variable Light chain of Panko1:
                                    (SEQ ID NO: 12)
DIVLTQTPLSLPVSLGDQASISCRSSQSIVHSNGNTYLEWYLQKPGQSPK

LLIYKVSNRFSGVPDRFSGSGSGTDFTLKISRVEAEDLGVYYCFQGSHVP

LTFGDGTKLELKR.

Variable Heavy chain of Panko2:
                                    (SEQ ID NO: 13)
EVKLVESGGGLVQPGGSMKLSCVASGFTFSNYWMNWVRQSPEKGLEWVAE

IRLKSNNYTTHYAESVKGRFTISRDDSKSSVSLQMNNLRVEDTGIYYCTR

HYYFDYWGQGTTLTVS.

Variable Light chain of Panko2:
                                    (SEQ ID NO: 14)
DIVMTQAAFSNPVTLGTSASISCRSSKSLLHSNGITYFFWYLQKPGLSPQ

LLIYQMSNLASGVPDRFSSSGSGTDFTLRISRVEAEDVGVYYCAQNLELP

PTFGGGTKLEIKR.
```

Variable amino acid sequences of Cetuximab VH and VL were obtained from http://redpoll.pharmacy.ualberta.ca/drugbank/cgi-bin/getCard.cgi?CARD=BTD00071.txt and reverse translated into cDNA coding sequences by using VectorNTI.

```
Variable Heavy chain of Cetuximab:
                                 (SEQ ID NO: 15)
QVQLKQSGPGLVQPSQSLSITCTVSGFSLTNYGVHWVRQSPGKGLEWLGV

IWSGGNTDYNTPFTSRLSINKDNSKSQVFFKMNSLQSNDTAIYYCARALT

YYDYEFAYWGQGTLVTVS.

Variable Light chain of Cetuximab:
                                 (SEQ ID NO: 16)
DILLTQSPVILSVSPGERVSFSCRASQSIGTNIHWYQQRTNGSPRLLIKY

ASESISGIPSRFSGSGSGTDFTLSINSVESEDIADYYCQQNNNWPTTFGA

GTKLELKR.
```

The cDNA sequence was extended by NcoI/NheI in the case for the VL and NcoI/SalI in the case of the VH and the cDNA was generated. The NcoI/XhoI-cut variable heavy chain fragments VH was cloned into the NcoI/SalI-cut BS-Leader vector as described in WO2004/065423. The BS-Leader vector includes a cloning cassette to introduce the T cell receptor signal peptide sequence at the 5' end and a splice donor sequence at the 3' end of the variable domains. The variable light chain VL of the corresponding antibody was amplified with a specific primer at the 3' end encoding additionally the splice donor site and was cloned via NcoI/NheI into the likewise digested BS-Leader vector. Thereafter, each HindIII/BamHI fragment from the BS-Leader vector was cloned into the corresponding eukaryotic expression vector. These vectors (pEFpuroCgamma1VB$_{HB}$, pEFdhfrCkappaVB$_{LB}$, pEFdhfrB$_{mutB}$CkappaVB$_{LB}$) comprise EF-1 alpha-promoter and HCMV enhancer, SV40 origin, polyadenylation signal, puromycin resistance gene in the vector for the heavy chain and the murine dihydrofolase gene (dhfr) for CHO cell expression or SEQ ID 1 (Sequence 1#) for K562, NM-F9 [DSM ACC2606], NM-D4 [DSM ACC2605], NM-H9, NM-E-2F9, NM-C-2F5, NM-H9D8 [DSM ACC2806], NM-H9D8-E6 [DSM ACC2807], NM-H9D8-E6Q12 [DSM ACC2856], or GT-2x [DSM ACC2858] expression for selection and gene amplification in the vector for the light chain, as well as the genomic sequences of the human constant gammal region for the heavy chain or the human constant kappa region for the light chain (primers for amplification from genomic human DNA and vector map see WO2004/065423).

EXAMPLE 5

Transfection of Eukaryotic Cells to Express the Chimeric Antibodies PankoMab, Panko1, Panko2, or Cetuximab and Gene Amplification Procedure to Generate High Producing Cell Clones in the Presence of Serum To express the chimeric antibodies in NM-F9 [DSM ACC2606] or CHOdhfr– [ATCC No. CRL-9096] cells were co-transfected with a mixture of above described vectors for the heavy and light chains (1:1 to 1:3) by lipofection using DMRIE-C or electroporation for the suspension cells as NM-F9 and lipofectamin or electroporation for the adherent cell line CHOdhfr–. Two days post-transfection, growth medium was changed to selection medium (NM-F9 in RPMI 1640+10% FCS+2 mM L-glutamine+0.75 µg/ml puromycin+50 nM methotrexate; CHOdhfr– in DMEM+10% dialysed FCS+2 mM L-glutamine+5 µg/ml puromycin+50 mM methotrexate) for 1 week. First amplification was performed by increasing methotrexate concentration to 100 nM for additional 2 weeks. Part of amplified cell population was single cell cloned in medium without addition of puromycin and methotrexate, rest of the cells were subjected to a new round of gene amplification by increasing the methotrexate concentration. In this manner four to six rounds of gene amplification (100, 200, 500, 1000, 2000, 3000 nM methotrexate) were performed. Additionally, best producing clones identified by clone screening and analysis were amplified further similarly.

Following single cell cloning in 96-well plates using limited dilution (0.5 cells per well), plates were cultivated for 2 to 3 weeks, microscopically analysed for growing cell clones, and cloning efficiency in % (number of wells with growing cell clones×100/theoretical number of seeded cells) was determined. Growing clones were screened for productivity using different procedures for adherent CHOdhfr– cells or for NM-F9 suspension cells.

CHOdhfr–:

Cells of growing clones were washed with PBS and harvested by Accutase treatment. Half of resuspended cells were seeded in a 96-well test plate, the other half was seeded in a 24-well plate for further cultivation. Test plate was cultivated for 20 to 24 h. Supernatant of each well was analysed for antibody titre as described in Determination of specific productivity rate (SPR) and doubling time (g) (see below). Relative cell density was measured using the MTT assay. In detail, cell were incubated with MTT solution for 2 h, solution was discarded and cell lysed by a 0.04 M HCl solution in 2-propanol. After 2 hours plate was moderately mixed and measured using a microtiter plate photometer with 570 nm filter in dual mode versus 630 nm reference filter.

NM-F9:

96-well plates were centrifuged and supernatant was discarded. Cells were resuspended in 200 µl fresh medium. Half of resuspended cells were seeded in a 96-well test plate and diluted with 100 µl medium, the other half remains in the cloning plates for further cultivation. After 2 days of cultivation, test plate was centrifuged and 20 µl of supernatant were analysed for antibody titre as described in Determination of specific productivity rate (SPR) and doubling time (g) (see below). Relative cell density was measured using the WST-1 assay by addition of 10 µl WST-1 solution (Roche) in each well. After 1 to 3 hours incubation measurement was performed using a microtiter plate photometer with 450 nm filter in dual mode versus 630 nm reference filter.

Cell clones with a high ratio of antibody titre to cell density were selected and cultivated and analysed further.

The conditions for K562, NM-D4 and NM-H9 were the same.

Determination of specific productivity rate (SPR) and doubling time (g)

For each clone, $2\times10P^{4P}$ cells were seeded per well of a 24-well tissue culture plate in 500 µl growth media. The cells were allowed to grow for 3 days, conditioned media harvested for analysis, and the cells were removed if necessary by Accutase and counted. Specific antibody titres were quantitatively determined from media samples by ELISA. Assay plates were coated with a human kappa chain specific antibody (BD). Bound recombinant antibody was detected with anti-human IgG (H+L) horseradish peroxidase (HRP)

conjugate (Jackson Immunoresearch Laboratories). For the quantification, purified recombinant chimeric antibody was used as a standard.

The SPR measured in picograms of specific protein per cell per day (pcd) is a function of both growth rate and productivity, and was calculated by following equations:

$$SPR = \frac{\text{total protein mass}}{\text{integral cell area } (ICA)}$$

$$ICA = \frac{(\text{final cell number} - \text{initial cell number}) \times \text{days in culture}}{\log_{eB}(\text{final cell number/initial cell number})}$$

Doubling time was calculated by following equation:

g=log 2×(hours in culture)/log(final cell number/initial cell number)

Determination of Average Yield and Maximum Yield for the Cell Lines

Following single cell cloning in 96-well plates using limited dilution (0.5 cells per well) as described above, from 200 theoretically plated single clones, the SPR is determined for growing cell clones and the average and deviation is determined, as well as the maximum yield for the different cell lines and different conditions. Table 1 compares the data of chimeric PankoMab-producing cell clones of CHOdhfr– and NM-F9 developed under serum-containing conditions.

EXAMPLE 6

Generation of Serum-Free High Yield Cell Clones Producing Antibody Molecule Composition Transfection of NM-H9D8, NM-H9D8-E6, NM-H9D8-E6Q12, or GT-2x adapted to serum-free medium X-Vivo 20 was performed under serum-free conditions using DMRIE-C or electroporation (Nucleofector, Amaxa). Two days post-transfection, growth medium was changed to selection medium (X-Vivo 20+0.75 µg/ml puromycin+50 nM methotrexate) for 1 week. First amplification was performed by increasing methotrexate concentration to 100 nM for additional 2 weeks. Part of amplified cell population was single cell cloned in X-Vivo without addition of puromycin and methotrexate, rest of the cells were subjected to a new round of gene amplification by increasing the methotrexate concentration. In this manner four to six rounds of gene amplification (100, 200, 500, 1000, 2000, 3000 nM methotrexate) were performed. Additionally, best producing clones identified by clone screening and analysis were amplified further similarly. Following single cell cloning in 96-well plates using limited dilution (0.5 cells per well), plates were cultivated for 2 to 3 weeks, microscopically analysed for growing cell clones, and cloning efficiency in % (number of wells with growing cell clones×100/theoretical number of seeded cells) was determined. Growing clones were screened for productivity using the same procedure as for NM-F9 suspension cells in the presence of serum (see above).

Determination of Average Yield and Maximum Yield for the Cell Clones

Following single cell cloning in 96-well plates using limited dilution (0.5 cells per well) as described above, from 200 theoretically plated single clones, the SPR is determined for growing cell clones and the average and deviation is determined, as well as the maximum yield for different conditions. Table 2 shows data of chimeric PankoMab-producing cell clones of NM-H9D8 [DSM ACC2806] developed completely under serum-free conditions.

Specific production rates (SPR) following amplification in cell lines according to the invention are higher than in CHOdhfr–, and highest in chimeric PankoMab-producing NM-H9D8 [DSM ACC2806] cells developed under serum-free conditions.

The production rate of the majority of clones is highly stable over at least 6 weeks without selection pressure. Best clone was stable with a SPR of 30 pcd over 6 weeks with a doubling rate of 24 h.

Date reflects productivity of clones in small-lab scale with further potential in productivity increase by process development, media optimisation and fermentation.

Higher productivity and yield of production clones developed under serum-free conditions are advantageous and conditions are the same for all other antibodies and for all cell lines as K562, NM-F9, NM-D4, NM-H9, NM-E-2F9, NM-C-2F5, NM-H9D8-E6 [DSM ACC2807], NM-H9D8-E6Q12 [DSM ACC2856], or GT-2x [DSM ACC2858] adapted to serum-free conditions.

EXAMPLE 7

Isolation of an Antibody Molecule Composition

For production and isolation of an antibody molecule composition according to the invention, the stably transfected cells secreting the chimeric antibodies PankoMab, Panko1, Panko2, or Cetuximab were cultivated in serum free medium until a cell density of about 1 to $2 \times 10P^{6P}$ cells/ml was reached. Following removal of the cells from the cell culture supernatant by centrifugation (400×g, 15 min), the chimeric antibody was purified using a protein A column (HiTrap r-protein A FF, Amersham Pharmacia Biotech). The purified antibody fraction eluted by sudden pH change was re-buffered in PBS and concentrated using Centriprep centrifuge tubes (cut off 50 kDa, Millipore).

EXAMPLE 8

Determination of Fc-Mediated Cellular Cytotoxicity of Antibody Molecule Compositions According to the Invention PBMC isolation from blood donors as effector cells PBMC were isolated from blood of healthy donors by density centrifugation with Ficoll-Hypaque (Biochrom). Cells were washed 3 times with RPMI 1640 supplemented with 5% FCS and cryopreserved in separate batches of $5 \times 10^7$ cells. PBMC were thawed and used directly or kept overnight in RPMI 1640 supplemented with 10% FCS (RPMI/FCS) before use in flow cytometry or as effector cells in the cytotoxic assays.

Detection of Antibody-Dependent Cellular Cytotoxicity in an In Vitro Model

The antibody-dependent cellular cytotoxicity (ADCC) of the recombinant antibodies according to the invention was investigated in an europium release assay. Target cells (ZR-75-1, $5 \times 10^6$) were incubated for 6 minutes on ice in 800 µl of europium buffer (50 mM HEPES, pH 7.4, 93 mM NaCl, 5 mM KCl, 2 mM $MgCl_2$, 10 mM diethylenetriaminepentaacetic acid, 2 mM europium(III)acetate), electroporated (710 V, 1 pulse, 30 µs) in a Multiporator (eppendorf), and subsequently incubated on ice for another 6 min. Thereafter, the cells were washed 5 times in RPMI 1640/5% FCS and seeded in a 96-well round-bottom plate (Nunc; $1 \times 10^4$ cells in 100 µl per well). Following addition of 20 µl of recombinant antibodies at varying concentration (0.5 to 25 µg/ml final concentration in 200 µl incubation volume) or the corresponding controls (medium, isotype control human IgG), human peripheral blood cells (80 µl per well) were added as effector cells, using an effector/target cell ratio of 50:1. 80 µl RPMI/FCS with no effector cells was added to determine spontaneous release. Maximum release was determined after complete lysis of the target cells with ethanol. Following incubation in an incubator at 37° C. for 4 hours, the plate was centrifuged at 500×g for 5 minutes, and 25 µl of each sample was pipetted in 200 µl per well of enhancement solution (Perkin-Elmer Wallac). Following incubation for 15 min at room temperature, the fluorescence was determined (VictorP$^{2P}$ Fluorometer, Perkin-Elmer Wallac). The specific cytotoxicity is obtained from the equation (experimental lysis–spontaneous lysis)/(maximum lysis–spontaneous lysis)*100.

Alternatively, target cells (LS174T or ZR-75-1, 3×10$^6$ cells) were incubated for 6 minutes on ice in 100 µl of europium buffer (50 mM HEPES, pH 7.4, 93 mM NaCl, 5 mM KCl, 2 mM MgCl$_2$, 10 mM diethylenetriaminepentaacetic acid, 2 mM europium(III)acetate), electroporated in a Nucleofector II (Amaxa) with program A-011, and subsequently incubated on ice for another 6 min. Thereafter, the cells were washed 4 times in RPMI 1640/5% FCS and seeded in a 96-well round-bottom plate (Nunc; 5 to 10×10$^3$ cells in 100 µl per well). Following addition of 20 µl of recombinant antibodies at varying concentration (0.001 to 100 ng/ml final concentration in 200 µl incubation volume for Cetuximab; 0.16-5 µg/ml for chimeric PankoMab, Panko1, or Panko2) or the corresponding controls (medium, isotype control human IgG), human peripheral blood cells (80 µl per well) were added as effector cells, using an effector/target cell ratio of 100:1 to 50:1. 80 µl RPMI/FCS with no effector cells was added to determine spontaneous release. Maximum release was determined after complete lysis of the target cells with 1% Triton X-100. Following incubation in an incubator at 37° C. for 4 hours or over night, the plate was centrifuged at 500×g for 5 minutes, and 25 µl of each sample was pipetted in 200 µl per well of enhancement solution (Perkin-Elmer Wallac). Following incubation for 10 min at room temperature, the fluorescence was determined (Victor$^2$ Fluorometer, Perkin-Elmer Wallac). The specific cytotoxicity is obtained from the equation (experimental lysis–spontaneous lysis)/(maximum lysis–spontaneous lysis)*100.

The ADCC activity of the Cetuximab isolated from fut8$^-$ cell line NM-H9D8-E6 is significantly higher than the ADCC activity of the Cetuximab isolated from the CHOdhfr– cells or SP2/0 cells. As shown in FIG. 2, Cetuximab isolated from NM-H9D8-E6 induces the same specific lysis of LS174T cells at about 30 times lower antibody concentrations as Cetuximab isolated from CHOdhfr– or from SP2/0 cells (Erbitux, obtained from Merck). This indicates a 30 times higher ADCC activity compared with the commercially available product. This result is obtained by using the production method of the present invention, resulting in an optimised glycosylation pattern.

Also the ADCC activity of the chimeric PankoMab isolated from NM-F9 [DSM ACC2606], K562, NM-H9, NM-D4 [DSM ACC2605], NM-H9D8-E6 [DSM ACC2807], NM-H9D8-E6Q12 [DSM ACC2856], GT-2x [DSM ACC2858], or NM-H9D8 [DSM ACC2806] is about 5 times higher than the ADCC activity of the chimeric PankoMab isolated from the CHOdhfr– cells. About a fifth of the chimaeric PankoMab concentration leads to the same ADCC activity as the chimeric PankoMab expressed in the CHOdhfr– cells. FIG. 3 shows the respective results using the NM-F9 cell line for comparison purposes.

The ADCC activity of the chimeric Panko1 isolated from NM-H9D8-E6 or NM-H9D8-E6Q12 is about 8 times higher than the ADCC activity of the chimeric Panko1 isolated from CHOdhfr– cells. About an eighth of the chimeric Panko1 concentration leads to the same ADCC activity as the chimeric Panko1 expressed in the CHOdhfr– cells. The respective results are shown in FIG. 4.

The ADCC activity of the chimeric Panko2 isolated from NM-H9D8 or GT-2x is about 6 times higher than the ADCC activity of the chimeric Panko2 isolated from CHOdhfr– cells. About a sixth of the chimeric Panko2 concentration leads to the same ADCC activity as the chimeric Panko2 expressed in the CHOdhfr– cells. The respective results are shown FIG. 5.

The ADCC activity of the chimeric Panko2 isolated from NM-H9D8-E6 is lower than the ADCC activity of the chimeric Panko2 isolated from NM-H9D8 cells. The respective results are shown FIG. 6.

Detection of Complement-Dependent Cellular Cytotoxicity in an In Vitro Model

The complement-dependent cellular cytotoxicity (CDC) of antibodies was investigated in an europium release assay. Eu$^{3+}$-loaded target cells (ZR-75-1, 3×10$^6$) were prepared as described above.

Thereafter, the cells were seeded in a 96-well round-bottom plate (Nunc; 5×10$^3$ cells in 100 µl per well). Following addition of 20 µl of antibodies at varying concentration (0.5 to 50 µg/ml final concentration in 200 µl incubation volume) or the corresponding controls (medium, isotype control human IgG), cells were incubated half an hour at room temperature. Thereafter, 10 µl per well baby rabbit complement (Cedarline, 1:5 to 1:10 diluted) were added. 10 µl RPMI/FCS with no complement was added to determine spontaneous release. Maximum release was determined after complete lysis of the target cells with ethanol or 1% TritonX-100. Following incubation in an incubator at 37° C. for 3 to 3.5 hours, the plate was centrifuged at 500×g for 5 minutes, and 25 µl of each sample was pipetted in 200 µl per well of enhancement solution (Perkin-Elmer Wallac). Following incubation for 10 min at room temperature, the fluorescence was determined (VictorP$^{2P}$ Fluorometer, Perkin-Elmer Wallac). The specific cytotoxicity is obtained from the equation (experimental lysis–spontaneous lysis)/(maximum lysis–spontaneous lysis)*100.

CDC activity of chimeric PankoMab isolated from NM-F9 cells is 8 times higher than CDC activity of chimeric PankoMab isolated form CHOdhfr– cells. Same specific lysis is induced at 8 times lower concentration of chimeric PankoMab isolated from NM-F9 compared to chimeric PankoMab isolated from CHOdhfr– cells. The respective results are shown FIG. 7.

Conjugate Formation Assay (CFA) to Analyse Phagocytosis Activity of Antibody Molecule Compositions Tumor Cell Staining with PKH26:

1×10P$^{7P}$ to 2×10P$^{7P}$ tumor cells were washed twice in PBS, resuspended in 1 ml diluent C, 1 ml PKH26 was added at concentration 12×10P$^{-6P}$ M for ZR-74-1, ZR-74-1TF, MCF-7 and MT-3. After 3 min incubation at RT, staining was stopped by adding 2 ml FCS for 1 min at RT. Medium (4 ml, RPMI supplemented with 1% L-glutamine, 10% FCS) was added, cells were spun down and washed 4 times with medium. Tumor cells were incubated o.n. at 37° C., 5% COB$_{2B}$ to allow the release of excess PKH-26.

Optimization of PKH-26 staining was performed with half of the cell numbers and volumes.

CFA:

PKH-26 labeled tumor cells were harvested with trypsin/EDTA, washed once with PBS and resuspended at $0.8 \times 10^6$ cells/ml in MAK cell medium (Invitrogen) in the presence or absence of recombinant antibody molecule compositions. Tumor cells (250 µl, $0.2 \times 10^6$ cells) were seeded in non-adherent polypropylene tubes.

MAK cells were prepared according to Boyer et al., Exp. Hematol. 27, 751-761 (1999), washed and resuspended at $1.6 \times 10^6$ cells/ml. 250 µl MAK cells ($0.2 \times 10^6$ cells) were added to PKH-26 labeled tumor cells (E:T ratio 2:1). Individual samples were incubated in duplicates at 4° C. and 37° C./5% $CO_{2B}$ for 3 h or o.n. (18-20 h).

After incubation at 3 h or o.n. cells were washed with PBS and stained with CD11c-FITC (1:18.5)+7-AAD (1:500) in PBS/10% FCS. Cells were washed with PBS, resuspended in 400 µl PBS. Acquisition was done on 10.000 cells in an Epics XL (Beckman Coulter).

Percentage of colocalized MAK cells was determined as percentage of PKH-26 positive cells in the cell population gated for all viable CD11c-FITC positive cells.

EXAMPLE 9

Analysis of Antibody Molecule Composition Binding Activity in ELISA

To analyse antigen binding of antibody molecule compositions expressed in different cell lines purified antibody molecule compositions of chimeric PankoMab and Panko 2 were measured in an ELISA on synthetic glycosylated MUC1 30-mer peptide with the sequence APPAHGVTSAPDT [GalNAcalpha]RPAPGSTAPPAHGVTSA (SEQ ID NO: 23). The non-glycosylated MUC1 peptide served as a control.

Using stock solutions (1 mg in 1 ml of bidest. $HB_{2B}O$) stored in portions at −20° C., a dilution of 1 µg/ml in PBS was produced. 50 µl/well was pipetted in a NUNC Immuno plate F96 MaxiSorp, and the test plate was incubated at 4° C. overnight. On the next day, the test plate was washed 3 times with PBS/0.2% Tween-20. Subsequently, non-specific binding sites were blocked with 2% BSA in PBS, incubated for at least 1 h at room temperature, and 50 µl of the recombinant PankoMab was applied (1-400 ng/ml PBS/1% BSA). After three wash steps with PBS/0.2% Tween-20, peroxidase-coupled secondary anti-human Fcγ1 antibody was employed to detect the specifically bound antibody. To detect the bound secondary antibody, a color reaction with TMB (3,3",5,5"-tetramethylbenzidine) was performed. After 15 minutes the reaction was quenched by adding 2.5 N $HB_{2B}SOB_{4B}$. Measurement was performed using a microtiter plate photometer with 450 nm filter in dual mode versus 630 nm reference filter.

The binding activity of the chimaeric PankoMab isolated from NM-F9 is about 50% higher than the binding activity of the chimaeric PankoMab isolated from the CHOdhfr− cells (FIG. 8).

The binding activity of the chimeric Panko2 expressed and isolated from the high sialylating clone NM-H9D8 in ELISA is comparable to that from GT-2x and higher compared to that from CHOdhfr− cells (FIG. 9).

EXAMPLE 10

Glycan Analysis of Antibody Molecule Compositions Expressed in NM-F9, NM- and CHOdhfr− Cells Glycans of at least 100 µg purified antibody were cleaved by acid hydrolysis. Sialic acids were labelled specifically by conjugation with the fluorescence dye DMB. Analysis was performed by HPLC e.g. on an Asahipak-NH2 column to separate the saccharides. Identification and calculation of sialic acids was performed by standard substances of appropriate sialic acids.

Analysis of chimeric PankoMab antibody molecule composition expressed in CHOdhfr− or NM-F9 cells revealed in <10% monosialylation of the CHOdhfr− product and nearly no sialylation of the NM-F9 or GT-2x product. The latter contained only non-charged glycans.

In more detail, glycans of at least 100 µg purified antibody were cleaved by acid hydrolysis. Sialic acids were labelled specifically by conjugation with the fluorescence dyes like DMB. Analysis was performed by HPLC e.g. by reverse phase chromatography on a RP-18 column. Identification and calculation of sialic acids was performed by standard substances of appropriate sialic acids.

For the determination of the charged glycan structures and the galactosylation state 100 µg antibodies were digested by trypsin and the N-Glykans was obtained by PNGaseF treatment. The purified glycans were labelled with 2-aminobenzamide (2-AB) and subjected to an anion exchange chromatography HPLC (Asahi-PAK-column) for the determination of charged N-glycan structures. For the determination of the galactosylation state the —N-glycans were treated by neuraminidase for depletion of the sialic acid content and separated by an Aminophase HPLC (Luna-NH2-column) and the peaks analysed by mass spectrometry.

The potentially bisecting GlcNAc carrying glycan containing peaks were separated in a second step by a reverse phase chromatography (RP18-column). By this triantennary and biantennary+bisected structures can be distinguished. The fucosylation degree of the antibodies was determined by aminophase HPLC (Luna-NH2-column) of the 2-AB labelled glycans. The peaks were quantified by integration and underlying glycan structure was analysed by mass spectrometry. The fucosylated and non-fucosylated structures were determined and the integrated peak areas were quantified.

Different antibody molecule compositions of Cetuximab, PankoMab and Panko1 expressed in NM-F9, GT-2x, NM-H9D8, NM-H9D8-E6, or CHOdhfr− cells were analysed and results are summarised in the tables 3 to 4.

Lectins which bind preferentially to alpha2-6 (SNA) or alpha2-3 (MAL-1) linked sialic acids were used to characterize the antibody sialylation by ELISA or Western blot analysis.

Western blot analysis was performed to identify the differently sialylated heavy chain of antibody molecule compositions expressed in CHOdhfr−, NM-F9, or NM-H9D8 [DSM ACC2806]. 5 µg of each antibody molecule composition were separated by SDS-Page in a 10% acrylamide gel under reducing conditions. Proteins were transferred to nitrocellulose and visualized by lectins and/or by secondary anti-human IgG antibodies. FIG. 10 shows the differently sialylated heavy chain of antibody molecule compositions of chimeric PankoMab expressed in CHOdhfr−, NM-F9, or NM-H9D8 [DSM ACC2806] either by secondary anti-human IgG antibodies (FIG. 10A) or SNA (FIG. 10B) which detects 2-6 sialylation. FIG. 11 shows the differently sialylated heavy chain of antibody molecule compositions of Cetuximab expressed in CHOdhfr− or NM-H9D8 visualized by SNA binding.

ELISA experiments were used to analyse the sialylation of antibodies isolated from supernatants of NM-F9, NM-H9D8, or NM-H9D8-E6 cells. Purified antibodies of 2 µg/ml in PBS and 50 µl per well were coated to 96 well microtiter plates (Maxisorp) at 4° C. over night, blocked (PBS/BSA), washed and incubated for 1 hour with biotinylated SNA (2 µg/ml, PBS/1% BSA) and washed again. Wells were than incubated with POD-streptavidin, washed and developed with TMB. Reaction was stopped by addition of 2.5N $H_2SO_4$ and the optical density was measured at 450 nm versus 630 nm as reference. FIG. 12 shows that binding of SNA occurs to antibodies expressed in NM-H9D8 or NM-H9D8-E6 cells, but not to antibodies expressed in CHOdhfr− or GT-2x cells. Intensities of binding are different for the individual antibodies what indicates a different sialylation degree caused by the fine structure of the individual antibodies or the availability of the saccharides under the conditions used.

ELISA experiments were performed by coating the purified antibodies expressed in the different cell lines in wells of microtiter plates (2 µg/ml, 50 µl per well) and detecting by appropriate biotinylated lectins SNA and MAL I. Dependence of lectin binding by sialylation was checked by neuraminidase treatment (0.1 U/ml and incubation at room temperature for 1 hour). Results for Cetuximab are illustrated in FIGS. 13A and 13B.

Dot blot analyses were performed to identify differences in sialylation of antibodies expressed in CHOdhfr−, NM-F9, NM-H9D8, and NM-H9D8-E6 cells. 3 µg of purified antibodies were spotted each to nitrocellulose, blocked with PBS/BSA, washed and visualized by SNA which detects 2,6-sialylation. FIG. 14 shows blots of the chimeric antibodies Panko1 and Panko2 isolated from CHOdhfr−, NM-F9, NM-H9D8, or NM-H9D8-E6 cells. 2,6-sialylation is only detectable on antibodies isolated from NM-H9D8 or NM-H9D8-E6 cells.

EXAMPLE 11

Detection of Bioavailability of Antibody Molecule Compositions Expressed in NM-F9, NM-H9D8 and CHOdhfr− Cells A longer bioavailability was measured in nude mice for the sialylated antibody PankoMab expressed in NM-H9D8 compared to the non sialylated antibody PankoMab expressed in NM-F9 cells. 5 µg purified antibody per mouse was i.v. injected for at least 3 mice per group. Blood samples were collected at different time points after injection (5 minutes, 2, 5, 8, 24, 48, 72, and 144 hours after injection), serum was isolated and the samples were stored at −80° C. until analysis. The antibody titer was determined in these samples by ELISA. FIG. 15 shows that chimeric PankoMab isolated from NM-H9D8 cells is longer available than that isolated from NM-F9 cells which is probably caused by the different sialylation of the antibodies.

EXAMPLE 12

Cloning of Vectors to Express hFSH in Eukaryotic Cells

Coding sequences of FSH alpha and FSH beta chain were PCR amplified with specific primers using the BAC clones RZPDB737B122053D (FSHalpha genomic), IRAUp969E0752D (FSHalpha cDNA) and RZPDB737H0619D6 (FSHbeta genomic) obtained from the RZPD, Germany.

```
Primers for FSH alpha chain:
FSHa-wt-f-KpnI:
                                  (SEQ ID NO: 17)
AAAGGTACCATGGATTACTACAGAAAATATG/

FSHa-b-BamHI:
                                  (SEQ ID NO: 18)
AAAGGATCCTTAAGATTTGTGATAATAAC;

Primers for FSH beta chain:
FSHb-wt-f-HindIII:
                                  (SEQ ID NO: 19)
TTTAAGCTTATGAAGACACTCCAGTTTTTC/

FSHb-b-BamHI:
                                  (SEQ ID NO: 20)
TTTGGATCCTTATTCTTTCATTTCACC
```

After amplification the products were cloned via HindIII/BamHI (FSHgenomicbeta) and Kpnl/BamHI (FSHgenomicalpha or FSHcDNAalpha) into the corresponding eukaryotic expression vector. A cDNA sequence was produced by Genesynthesis coding for the FSH beta chain fused to a TCR-leader sequence and cloned into the eukaryotic expression vector (FSHcDNAbeta).

```
Sequence FSHcDNAbeta (TCR-leader sequence
underlined):
                                  (SEQ ID NO: 21)
atggcctgccccggcttcctgtgggccctggtgatcagcacctgcctgga attctccatggctaacagctgcgagctgaccaacatcaccatcgccatcg agaaagaggaatgccggttctgcatcagcatcaacaccacctggtgcgcc ggctactgctacacccgggacctggtgtacaaggaccccgccaggcccaa gatccagaaaacctgcaccttcaaagaactggtgtacgagaccgtgcggg tgcccggctgcgcccaccacgccgacagcctgtacacctaccccgtggcc acccagtgccactgcggcaagtgcgacagcgacagcaccgactgcaccgt gaggggcctgggccccagctactgcagcttcggcgagatgaaagagtga
```

The expression vectors (pEFpuro and pEFdhfrB$_{mutB}$) comprise EF-1 alpha-promoter and HCMV enhancer, SV40 origin, polyadenylation signal, puromycin resistance gene in the vector for the alpha chain, and the murine dihydrofolase gene (dhfr) for CHO cell expression or SEQ ID 1 (Sequence 1#) for NM-F9, GT-2x, K562, NM-H9, NM-D4, or NM-H9D8 expression for selection and gene amplification in the vector for the beta chain.

EXAMPLE 13

Transfection of Eukaryotic Cells to Express Human Recombinant hFSH and Gene Amplification Procedure to Generate High Producing Cell Clones Under Serum Free Conditions (GT-2x and NM-H9D8) or Serum Containing Conditions (CHOdhfr−)

To express hFSH in GT-2x [DSM ACC2858], NM-H9D8 (DSM ACC2806), and CHOdhfr− (ATCC No. CRL-9096) cells were co-transfected with a mixture of above described vectors for alpha and the beta chains (1:1 to 1:3) by lipofection using DMRIE-C or electroporation (Nucleofector; Amaxa) for the suspension cells as GT-2x (FSHcDNAalpha/FSHgenomicbeta) and NM-H9D8 (FSHcDNAalpha/FSHcDNAbeta) and lipofectamin or electroporation for the adherent cell line CHOdhfr– (FSHgenomicalpha/FSHgenomicbeta). These are exemplary combinations used in this setup. Each other combination of a hFSH alpha and a hFSH beta chain expression plasmid leads to comparable results.

Two days post-transfection, growth medium was changed to selection medium (GT-2x and NM-H9D8 in X-Vivo20 medium+0.75 µg/ml puromycin+50 nM methotrexate; CHOdhfr– in DMEM+10% dialysed FCS+2 mM L-glutamine+5 µg/ml puromycin+50 mM methotrexate) for 1 week. First amplification was performed by increasing methotrexate concentration to 100 nM for additional 2 weeks and 200 nM methotrexate for another 2 weeks. Part of amplified cell population was single cell cloned in medium without addition of puromycin and methotrexate. Rest of the cells were subjected to a new round of gene amplification by increasing the methotrexate concentration. In this manner two to three rounds of gene amplification (100, 200, 500 nM methotrexate) were performed. Additionally, best producing clones identified by clone screening and analysis were amplified further similarly.

CHOdhfr–:

Cells of growing clones were washed with PBS and harvested by Accutase treatment. Half of resuspended cells were seeded in a 96-well test plate, the other half was seeded in a 24-well plate for further cultivation. Test plate was cultivated for 20 to 24 h. Supernatant of each well was analysed for antibody titre as described in Determination of specific productivity rate (SPR) and doubling time (g) (see below). Relative cell density was measured using the MTT assay. In detail, cell were incubated with MTT solution for 2 h, solution was discarded and cell lysed by a 0.04 M HCl solution in 2-propanol. After 2 hours plate was moderately mixed and measured using a microtiter plate photometer with 570 nm filter in dual mode versus 630 nm reference filter.

GT-2x and NM-H9D8:

96-well plates were centrifuged and supernatant was discarded. Cells were resuspended in 200 µl fresh medium. Half of resuspended cells were seeded in a 96-well test plate and diluted with 100 µl medium, the other half remains in the cloning plates for further cultivation. After 2 days of cultivation, test plate was centrifuged and 20 µl of supernatant were analysed for antibody titre as described in Determination of specific productivity rate (SPR) and doubling time (g) (see below). Relative cell density was measured using the WST-1 assay by addition of 10 µl WST-1 solution (Roche) in each well. After 1 to 3 hours incubation measurement was performed using a microtiter plate photometer with 450 nm filter in dual mode versus 630 nm reference filter.

Determination of specific productivity rate (SPR) and doubling time (g)

For each clone, $2 \times 10P^{4P}$ cells were seeded per well of a 24-well tissue culture plate in 500 µl growth media. The cells were allowed to grow for 3 days, conditioned media harvested for analysis, and the cells were removed if necessary by Accutase and counted. Specific antibody titres were quantitatively determined from media samples by ELISA. Assay plates were coated with a mouse mAB specific to hFSH beta (ab22473). Bound recombinant hFSH was incubated with goat polyclonal antibody specific to hCG alpha (ab20712) and detected with a donkey anti goat IgG H+L-POD (JacksonImmuno Cat.No 305-035-003). For the quantification, purified recombinant hFSH was used as a standard.

The SPR measured in picograms of specific protein per cell per day (pcd) is a function of both growth rate and productivity, and was calculated by following equations:

$$SPR = \frac{\text{total protein mass}}{\text{integral cell area } (ICA)}$$

$$ICA = \frac{(\text{final cell number} - \text{initial cell number}) \times \text{days in culture}}{\log B_{eB}(\text{final cell number/initial cell number})}$$

Doubling time was calculated by following equation:

$g = \log 2 \times (\text{hours in culture})/\log(\text{final cell number/initial cell number})$ Determination of Average Yield and Maximum Yield for the Cell Lines Following single cell cloning in 96-well plates using limited dilution (0.5 cells per well) as described above, from 200 theoretically plated single clones, the SPR is determined for growing cell clones and the average and deviation is determined, as well as the maximum yield for the different cell lines and different conditions. Table 7 and Table 8 compares the data of hFSH producing cell clones of CHOdhfr–, GT-2x, and NM-H9D8 developed under serum-containing conditions (CHOdhfr–) and serum free conditions (GT-2x and NM-H9D8).

EXAMPLE 14

Isolation of hFSH Molecule Composition

For production and isolation of a hFSH molecule composition according to the invention, the stably transfected cells secreting hFSH were cultivated in serum free medium until a cell density of about 1 to $2 \times 10P^{6P}$ cells/ml was reached. Following removal of the cells from the cell culture supernatant by centrifugation (400×g, 15 min), the chimeric antibody was purified comprising affinity chromatography using a polyclonal antibody to hCGalpha coupled to an NHS activated column (HiTrap NHS-activated HP; GE Healthcare). The purified FSH fraction eluted by sudden pH change was re-buffered in PBS and concentrated using Centriprep centrifuge tubes (cut off 10 kDa, Millipore) and analysed by SDS-PAGE (see FIG. 16).

EXAMPLE 15

Determination the Activity of FSH Molecule Compositions According to the Invention The activity of FSH molecules carrying a different glycosylation pattern can be determined according to the subsequently described methods. In order to select a suitable cell line with the screening method according to the present invention, which provides an optimized glycosylation, the FSH molecule is expressed in different cell lines, thereby obtaining FSH compositions from the individual cell lines depicting a diverging glycosylation pattern with respect to e.g. the sialylation degree, galactosylation and/or fucosylation degree. The FSH molecule/composition having the most favourable activity and hence glycosylation pattern can be determined by at least one of the following methods:

Rat Granulosa Cell Assay:

Granulosa cells were obtained from DES treated hypophysectomised rats. The method for the preparation of the cells is described in detail by Jia and Hsueh 1985.

The obtained cells were cultured in a 24 well scale with ~160000 cells/well in McCoy's 5A medium containing 100 nM DES, 0.125 M 1-methyl-3-isobuthylxanthine, 2 mM Glutamine, 1 µM androstenedione, 100 U/ml penicillin and 100 µg/ml streptomycin, 1 µg/ml bovine insulin and increasing concentrations of rFSH preparations derived from GT-2x and NM-H9D8 cells (0-1 µg/ml) for up to 72 hours. The media were collected 72 h after incubation and stored at −20° C. until quantification of oestradiol by ELISA (Calbiotech # ES071S).

293HEK Assay:

HEK293 cells stably transfected with the hFSH-receptor ($2 \times 10^5$ cells/35 mm culture dish) were exposed to increasing doses of each protein molecule composition of FSH obtained from GT-2x and NM-H9D8 cells in the range of 0-1 µg/ml FSH in the presence of 0.125 mM 1-methyl-3-isobuthylxanthine for 24 h at 37° C. for up to 72 hours. After incubation, total (intra- and extracellular) cAMP concentrations were determined by the cAMP Direct Biotrak™ EIA (GE Healthcare, Cat. no.: RPN225) according to the manufacturer's instructions.

GFSHR-17 Cell Assay:

Cells were cultured with Dulbecco modified Eagle medium Ham F12 (1:1 v:v; Biochrom KG, Berlin, Germany) containing 5% fetal calf serum (Biochrom KG, Berlin, Germany). The cells were plated with $2 \times 10^5$ cell/24 well plate and incubated with the FSH protein molecule compositions obtained from GT-2x and NM-H9D8 cells for 24 h at a range from 0-1 µg/ml for 1-24 hours. The media were collected after incubation and stored at −20° C. until quantification of progesterone by using a progesterone ELISA assay (Biochem Immunosystems, Freiburg, Germany) according to the manufacturer's instructions.

Human Granulosa Cell Assay

Granulosa-lutein cells from follicular aspirates, obtained from women participating an in vitro fertilization program at the University of Munster, were enriched as described by Khan et al., 1990 and seeded into 6-well plates ($1-1.5 \times 10^5$ viable cells per well). The cells were incubated at 37° C. in HAM's F12/Dulbecco's modified essential medium (DMEM) (1:1; ICN Biomedicals, Meckenheim, Germany) supplemented with 10% heat-inactivated fetal calf serum (FCS; Gibco, Eggenstein, Germany), penicillin (50 units/nil), streptomycin (50 pg/ml), gentamycin (100 pg/rnl) and amphotericin (0.6 pg/ml) in an atmosphere of 5% $CO_2$. The cells were exposed to increasing doses of each protein molecule composition of FSH obtained from GT-2x and NM-H9D8 cells in the range of 0-1 µg/ml FSH in the presence of 0.125 mM 1-methyl-3-isobuthylxanthine for 24 h at 37° C. for up to 72 hours. After incubation, total (intra- and extracellular) cAMP concentrations were determined by the cAMP Direct Biotrak™ EIA (GE Healthcare, Cat. no.: RPN225) according to the manufacturer's instructions.

EXAMPLE 16

Glycan Analysis of FSH Compositions Expressed in GT-2x and CHOdhfr− Cells

Western blot analysis was performed to identify the differently sialylated FSH molecule compositions expressed in CHOdhfr−, GT-2x [DSM ACC2858], or NM-H9D8 [DSM ACC2806]. 5 µg of each antibody molecule composition were separated by SDS-Page in a 10% acrylamide gel under reducing conditions. Proteins were transferred to nitrocellulose and visualized by SNA (FIG. 17) which detects 2-6 sialylation.

A detailed glycan analysis can be performed according to example 10 for determination of the sialic acid content, charge distribution, fucose content, galactosylation state and bisecting GlcNAc content.

Definitions According to IUPAC-IUBMB Recommendations (1996)

Neu5Gc: 5-N-glycolyl-α-neuraminic acid
Neu5Ac and NeuNAc: 5-N-acetyl-α-neuraminic acid
Galα1,3Gal: α-D-galactopyranosyl-(1→3)-galactopyranosyl-adjacent saccharide
2,3 linked Neuraminic acid: 5-N-acetyl-α-neuraminyl-(2→3)-adjacent saccharide
2,6 linked neuraminic acid: 5-N-acetyl-α-neuraminyl-(2→6)-adjacent saccharide It is to be understood that this invention is not limited to the particular methodology, protocols and/or reagents as described herein as these may vary. It is also to be understood that the terminology used herein is for the purpose of describing particular embodiments only, and is not intended to limit the scope of the present invention which will be limited only by the appended claims.

SEQ ID:

```
Sequence #1
                                           (SEQ ID NO: 1)
MVRPLNCIVAVSQDMGIGKNGDLPWPPLRNEWKYFQRMTTTSSVEGKQNL

VIMGRKTWFSIPEKNRPLKDRINIVLSRELKEPPRGAHFLAKSLDDALRL

IEQPELASKVDMVWIVGGSSVYQEAMNQPGHLRLFVTRIMQEFESDTFFP

EIDLGKYKLLPEYPGVLSEVQEEKGIKYKFEVYEKKD

Sequence #2
                                           (SEQ ID NO: 2)
MVGSLNCIVAVSQNMGIGKNGDLPWPPLRNESRYFQRMTTTSSVEGKQNL

VIMGKKTWFSIPEKNRPLKGRINLVLSRELKEPPQGAHFLSRSLDDALKL

TEQPELANKVDMVWIVGGSSVYKEAMNHPGHLKLFVTRIMQDFESDTFFP

EIDLEKYKLLPEYPGVLSDVQEEKGIKYKFEVYEKND

Sequence #3
                                           (SEQ ID NO: 3)
MVGSLNCIVAVSQNMGIGKNGDLPWPPLRNEARYFQRMTTTSSVEGKQNL

VIMGKKTWFSIPEKNRPLKGRINLVLSRELKEPPQGAHFLSRSLDDALKL

TEQPELANKVDMVWIVGGSSVYKEAMNHPGHLKLFVTRIMQDFESDTFFP

EIDLEKYKLLPEYPGVLSDVQEEKGIKYKFEVYEKND
```

-continued

```
Sequence #4
                                           (SEQ ID NO: 4)
MVGSLNCIVAVSQNMGIGKNGDLPWPPLRNEGRYFQRMTTTSSVEGKQNL

VIMGKKTWFSIPEKNRPLKGRINLVLSRELKEPPQGAHFLSRSLDDALKL

TEQPELANKVDMVWIVGGSSVYKEAMNHPGHLKLFVTRIMQDFESDTFFP

EIDLEKYKLLPEYPGVLSDVQEEKGIKYKFEVYEKND

Sequence #5
                                           (SEQ ID NO: 5)
MVGSLNCIVAVSQNMGIGKNGDYPWPPLRNEFRYFQRMTTTSSVEGKQNL

VIMGKKTWFSIPEKNRPLKGRINLVLSRELKEPPQGAHFLSRSLDDALKL

TEQPELANKVDMVWIVGGSSVYKEAMNHPGHLKLFVTRIMQDFESDTFFP

EIDLEKYKLLPEYPGVLSDVQEEKGIKYKFEVYEKND

Sequence #6
                                           (SEQ ID NO: 6)
MVGSLNCIVAVSQNMGIGKNGDRPWPPLRNEFRYFQRMTTTSSVEGKQNL

VIMGKKTWFSIPEKNRPLKGRINLVLSRELKEPPQGAHFLSRSLDDALKL

TEQPELANKVDMVWIVGGSSVYKEAMNHPGHLKLFVTRIMQDFESDTFFP

EIDLEKYKLLPEYPGVLSDVQEEKGIKYKFEVYEKND

Sequence #7
                                           (SEQ ID NO: 7)
MVGSLNCIVAVSQNMGIGKNGDFPWPPLRNEFRYFQRMTTTSSVEGKQNL

VIMGKKTWFSIPEKNRPLKGRINLVLSRELKEPPQGAHFLSRSLDDALKL

TEQPELANKVDMVWIVGGSSVYKEAMNHPGHLKLFVTRIMQDFESDTFFP

EIDLEKYKLLPEYPGVLSDVQEEKGIKYKFEVYEKND

Sequence #8
                                           (SEQ ID NO: 8)
MVRPLNCIVAVSQNMGIGKNGDRPWPPLRNEFKYFQRMTTTSSVEGKQNL

VIMGRKTWFSIPEKNRPLKDRINIVLSRELKEPPRGAHFLAKSLDDALRL

IEQPELASKVDMVWIVGGSSVYQEAMNQPGHLRLFVTRIMQEFESDTFFP

EIDLGKYKLLPEYPGVLSEVQEEKGIKYKFEVYEKKD

Sequence #9
                                           (SEQ ID NO: 9)
MVRPLNCIVAVSQNMGIGKNGDYPWPPLRNEFKYFQRMTTTSSVEGKQNL

VIMGRKTWFSIPEKNRPLKDRINIVLSRELKEPPRGAHFLAKSLDDALRL

IEQPELASKVDMVWIVGGSSVYQEAMNQPGHLRLFVTRIMQEFESDTFFP

EIDLGKYKLLPEYPGVLSEVQEEKGIKYKFEVYEKKD

Sequence #10
                                          (SEQ ID NO: 10)
MWLGSLLLLGTVACSISA
```

TABLE 1

|  | CHOdhfr- | NM-F9 |
|---|---|---|
| Production rate (cIgG1) pcd determined after 1st to 4th round of gene amplification (methotrexate) and single cell cloning from theoretically 200 seeded clones (limited dilution) | 1st round (100 nM MTX) Average: 2 +/− 1 pcd; Max: 3 pcd 2nd round (200 nM MTX) Average: 5 +/− 1 pcd; Max: 7 pcd 3rd round (500 nM MTX) | 1st round (100 nM MTX) Average: 5 +/− 1.5 pcd; Max: 13 pcd 2nd round (200 nM MTX) Average: 7.5 +/− 4.5 pcd; Max: 19 pcd 3nd round (500 nM MTX) |

TABLE 1-continued

|  | CHOdhfr- | NM-F9 |
|---|---|---|
|  | Average: 9 +/− 5 pcd; Max: 17 pcd 4th round (1000 nM MTX) Average: 13 +/− 5 pcd; Max: 22 pcd | Average: 12.5 +/− 4.5 pcd; Max: 19 pcd 4nd round (1000 nM MTX) Average: 16.5 +/− 6 pcd; Max: 27 pcd |

TABLE 2

|  | NM-H9D8 |
|---|---|
| Production rate (cIgG1) pcd determined after 1st to 5th round of gene amplification (methotrexate) and single cell cloning from theoretically 200 seeded clones (limited dilution) | 1st round (100 nM MTX) Average: 7 +/− 4 pcd; Max: 14 pcd 2nd round (200 nM MTX) Average: 14 +/− 4 pcd; Max: 23 pcd 3rd round (500 nM MTX) Average: 13 +/− 6 pcd; Max: 31 pcd 4th round (1000 nM MTX) Average: 23 +/− 8 pcd; Max: 34 pcd 5th round (2000 nM MTX) Average: 23 +/− 9 pcd; Max: 38 pcd |

TABLE 3

|  | pmol Neu5Gc | pmol Neu5Ac | pmol Neu5Gc/ μg Protein | pmol Neu5Ac/ μg Protein |
|---|---|---|---|---|
| Erbitux (Merck; SP2/0) | 0.149 | 0.000 | 1.784 | 0.000 |
| CetuxiMab GT-2x | 0.000 | 0.278 | 0.000 | 3.335 |
| CetuxiMab NM-H9D8 | 0.000 | 1.156 | 0.000 | 12.003 |
| cPankoMab CHOdhfr- | 0.000 | 0.477 | 0.000 | 4.921 |
| cPankoMab GT-2x | 0.000 | 0.248 | 0.000 | 2.990 |
| cPankoMab NM-H9D8 | 0.000 | 0.776 | 0.000 | 13.856 |

TABLE 4

|  | A0 | A1 | A2 | A3 | A4 |
|---|---|---|---|---|---|
| Panko1 CHOdhfr- | 75 | 9 | 11 | 4 | 1 |
| Panko1 NM-H9D8 | 43 | 14 | 32 | 10 | 1 |
| Panko1 NM-H9D8-E6 | 40 | 16 | 33 | 10 | 1 |
| cPankoMab CHOdhfr- | 93 | 7 | 0 | 0 | 0 |
| cPankoMab NM-F9 | 99 | 1 | 0 | 0 | 0 |
| cPankoMab NM-H9D8 | 62 | 26 | 11 | 1 | 0 |

TABLE 5

|  | G0[%] | G1[%] | G2[%] | G3[%] |
|---|---|---|---|---|
| Panko1 CHOdhfr- | 22 | 45 | 33 | 0 |
| Panko1 NM-H9D8 | 7 | 8 | 66 | 14 |
| Panko1 NM-H9D8-E6 | 5 | 18 | 58 | 19 |
| cPankoMab CHOdhfr- | 28 | 36 | 35 | 1 |
| cPankoMab NM-F9 | 7 | 26 | 65 | 2 |
| cPankoMab NM-H9D8 | 7 | 32 | 59 | 0 |

TABLE 6

|  | fucosylated | non fucosylated | biantennary + bisecting GlcNAc |
|---|---|---|---|
| Panko1 CHOdhfr- | 100 | 0 | 0 |
| Panko1 NM-H9D8 | 45 | 55 | 5 |
| Panko1 NM-H9D8-E6 | 21 | 79 | 2 |

|  | biantennary | biantennary + bisecting GlcNAc | non fucosylated |
|---|---|---|---|
| cPankoMab-CHO | 99 | 0 | 0 |
| cPankoMab-NM-F9 | 68 | 29 | 6 |
| cPankoMab-NM-H9D8 | 59 | 39 | 1 |

TABLE 7

|  | CHOdhfr- | GT-2X |
|---|---|---|
| Production rate (FSH) pcd determined after 3rd round of gene amplification (methotrexate) and single cell cloning from theoretically 200 seeded clones (limited dilution) | 3rd round (500 nM MTX) Average: <1 pcd; Max: 0.05 pcd | 2nd round (200 nM MTX) Average: 2.5 +/- 2.0 pcd: Max: 6 pcd 3rd round (500 nm MTX) Average: 2.5 +/- 1.3 pcd; Max: 12 pcd |

TABLE 8

|  | NM-H9D8 |
|---|---|
| Production rate (FSH) pcd determined after 2nd round of gene amplification (methotrexate) and single cell cloning from theoretically 200 seeded clones (limited dilution) | 2nd round (200 nM MTX) Average: 2.2 +/- 1.2 pcd; Max: 4 pcd |

TABLE 9

| | | |
|---|---|---|
| No NeuGc | No NeuGc | No NeuGc |
| No detectable terminal Galalpha 1-3 Gal | No detectable terminal Galalpha 1-3 Gal | No detectable terminal Galalpha 1-3 Gal |
| High Galactose as defined in claim 2 and depending claims | High Galactose as defined in claim 2 and depending claims | High Galactose as defined in claim 2 and depending claims |
| Low Fucose as defined in claim 2 and depending claims | Low Fucose as defined in claim 2 and depending claims | Low Fucose as defined in claim 2 and depending claims |
| bisecGlcNAc high Activity, in particular Fc activity higher affinity high yield | bisecGlcNAc high Activity, in particular Fc activity higher affinity high yield | bisecGlcNAc high Activity, in particular Fc activity higher affinity high yield |
| 2-6 NeuNAc 2-3 NeuNAc more sialic acid as defined in claim 2 and depending claims | low sialic acid as defined in claim 2 and depending claims | 2-6 NeuNAc |
| No NeuGc | No NeuGc | No NeuGc |
| No detectable terminal Galalpha 1-3 Gal | No detectable terminal Galalpha 1-3 Gal | No detectable terminal Galalpha 1-3 Gal |
| High Galactose as defined in claim 2 and depending claims | High Galactose as defined in claim 2 and depending claims | High Galactose as defined in claim 2 and depending claims |
| Low Fucose as defined in claim 2 and depending claims | Low Fucose as defined in claim 2 and depending claims | Low Fucose as defined in claim 2 and depending claims |
| bisecGlcNAc high Activity, in particular Fc activity high yield | bisecGlcNAc high Activity, in particular Fc activity high yield | bisecGlcNAc high Activity, in particular Fc activity high yield |
| 2-6 NeuNAc 2-3 NeuNAc more sialic acid as defined in claim 2 and depending claims | low sialic acid as defined in claim 2 and depending claims | 2-6 NeuNAc |
| No NeuGc | No NeuGc | No NeuGc |
| No detectable terminal Galalpha 1-3 Gal | No detectable terminal Galalpha 1-3 Gal | No detectable terminal Galalpha 1-3 Gal |
| High Galactose as defined in claim 2 and depending claims | High Galactose as defined in claim 2 and depending claims | High Galactose as defined in claim 2 and depending claims |
| Low Fucose as defined in claim 2 and depending claims | Low Fucose as defined in claim 2 and depending claims | Low Fucose as defined in claim 2 and depending claims |
| bisecGlcNAc high Activity, in particular Fc activity high yield | bisecGlcNAc high Activity, in particular Fc activity high yield | bisecGlcNAc high Activity, in particular Fc activity high yield |
| 2-6 NeuNAc 2-3 NeuNAc more sialic acid as defined in claim 2 and depending claims | low sialic acid as defined in claim 2 and depending claims | 2-6 NeuNAc |
| No NeuGc | No NeuGc | No NeuGc |
| No detectable terminal Galalpha 1-3 Gal | No detectable terminal Galalpha 1-3 Gal | No detectable terminal Galalpha 1-3 Gal |

TABLE 9-continued

| | | |
|---|---|---|
| High Galactose as defined in claim 2 and depending claims | High Galactose as defined in claim 2 and depending claims | High Galactose as defined in claim 2 and depending claims |
| bisecGlcNAc | bisecGlcNAc | bisecGlcNAc |
| high Activity, in particular Fc activity | high Activity, in particular Fc activity | high Activity, in particular Fc activity |
| high yield | high yield | high yield |
| 2-6 NeuNAc | low sialic acid as defined in claim 2 and depending claims | 2-6 NeuNAc |
| 2-3 NeuNAc more sialic acid as defined in claim 2 and depending claims | | |
| No NeuGc | No NeuGc | No NeuGc |
| No detectable terminal Galalpha 1-3 Gal | No detectable terminal Galalpha 1-3 Gal | No detectable terminal Galalpha 1-3 Gal |
| High Galactose as defined in claim 2 and depending claims | High Galactose as defined in claim 2 and depending claims | High Galactose as defined in claim 2 and depending claims |
| bisecGlcNAc | bisecGlcNAc | bisecGlcNAc |
| high Activity, in particular Fc activity | high Activity, in particular Fc activity | high Activity, in particular Fc activity |
| 2-6 NeuNAc | low sialic acid as defined in claim 2 and depending claims | 2-6 NeuNAc |
| 2-3 NeuNAc more sialic acid as defined in claim 2 and depending claims | | |
| No NeuGc | No NeuGc | No NeuGc |
| No detectable terminal Galalpha 1-3 Gal | No detectable terminal Galalpha 1-3 Gal | No detectable terminal Galalpha 1-3 Gal |
| High Galactose as defined in claim 2 and depending claims | High Galactose as defined in claim 2 and depending claims | High Galactose as defined in claim 2 and depending claims |
| bisecGlcNAc | bisecGlcNAc | bisecGlcNAc |
| high yield | high yield | high yield |
| 2-6 NeuNAc | low sialic acid as defined in claim 2 and depending claims | 6 NeuNAc |
| 2-3 NeuNAc more sialic acid as defined in claim 2 and depending claims | | |
| No NeuGc | No NeuGc | No NeuGc |
| No detectable terminal Galalpha 1-3 Gal | No detectable terminal Galalpha 1-3 Gal | No detectable terminal Galalpha 1-3 Gal |
| High Galactose as defined in claim 2 and depending claims | High Galactose as defined in claim 2 and depending claims | High Galactose as defined in claim 2 and depending claims |
| high Activity, in particular Fc activity | high Activity, in particular Fc activity | high Activity, in particular Fc activity |
| 2-6 NeuNAc | low sialic acid as defined in claim 2 and depending claims | 2-6 NeuNAc |
| 2-3 NeuNAc more sialic acid as defined in claim 2 and depending claims | | |
| No NeuGc | No NeuGc | No NeuGc |
| No detectable terminal Galalpha 1-3 Gal | No detectable terminal Galalpha 1-3 Gal | No detectable terminal Galalpha 1-3 Gal |
| High Galactose as defined in claim 2 and depending claims | High Galactose as defined in claim 2 and depending claims | High Galactose as defined in claim 2 and depending claims |
| high yield | high yield | high yield |
| 2-6 NeuNAc | low sialic acid as defined in claim 2 and depending claims | 2-6 NeuNAc |
| 2-3 NeuNAc more sialic acid as defined in claim 2 and depending claims | | |
| No NeuGc | No NeuGc | No NeuGc |
| No detectable terminal Galalpha 1-3 Gal | No detectable terminal Galalpha 1-3 Gal | No detectable terminal Galalpha 1-3 Gal |
| Low Fucose as defined in claim 2 and depending claims | Low Fucose as defined in claim 2 and depending claims | Low Fucose as defined in claim 2 and depending claims |
| bisecGlcNAc | bisecGlcNAc | bisecGlcNAc |
| high Activity, in particular Fc activity | high Activity, in particular Fc activity | high Activity, in particular Fc activity |
| higher affinity | higher affinity | higher affinity |
| high yield | high yield | high yield |
| 2-6 NeuNAc | low sialic acid as defined in claim 2 and depending claims | 2-6 NeuNAc |
| 2-3 NeuNAc more sialic acid as defined in claim 2 and depending claims | | |
| No NeuGc | No NeuGc | No NeuGc |
| No detectable terminal Galalpha 1-3 Gal | No detectable terminal Galalpha 1-3 Gal | No detectable terminal Galalpha 1-3 Gal |
| Low Fucose as defined in claim 2 and depending claims | Low Fucose as defined in claim 2 and depending claims | Low Fucose as defined in claim 2 and depending claims |
| bisecGlcNAc | bisecGlcNAc | bisecGlcNAc |
| high Activity, in particular Fc activity | high Activity, in particular Fc activity | high Activity, in particular Fc activity |
| high yield | high yield | high yield |
| 2-6 NeuNAc | low sialic acid as defined in claim 2 and depending claims | 2-6 NeuNAc |
| 2-3 NeuNAc more sialic acid as defined in claim 2 and depending claims | | |
| No NeuGc | No NeuGc | No NeuGc |
| No detectable terminal Galalpha 1-3 Gal | No detectable terminal Galalpha 1-3 Gal | No detectable terminal Galalpha 1-3 Gal |
| Low Fucose as defined in claim 2 and depending claims | Low Fucose as defined in claim 2 and depending claims | Low Fucose as defined in claim 2 and depending claims |
| bisecGlcNAc | bisecGlcNAc | bisecGlcNAc |
| high yield | high yield | high yield |
| 2-6 NeuNAc | low sialic acid as defined in claim 2 and depending claims | 2-6 NeuNAc |
| 2-3 NeuNAc more sialic acid as defined in claim 2 and depending claims | | |
| No NeuGc | No NeuGc | No NeuGc |
| No detectable terminal Galalpha 1-3 Gal | No detectable terminal Galalpha 1-3 Gal | No detectable terminal Galalpha 1-3 Gal |
| Low Fucose as defined in claim 2 and depending claims | Low Fucose as defined in claim 2 and depending claims | Low Fucose as defined in claim 2 and depending claims |
| bisecGlcNAc | bisecGlcNAc | bisecGlcNAc |
| high Activity, in particular Fc activity | high Activity, in particular Fc activity | high Activity, in particular Fc activity |
| 2-6 NeuNAc | low sialic acid as defined in claim 2 and depending claims | 2-6 NeuNAc |
| 2-3 NeuNAc more sialic acid as defined in claim 2 and depending claims | | |
| No NeuGc | No NeuGc | No NeuGc |
| No detectable terminal Galalpha 1-3 Gal | No detectable terminal Galalpha 1-3 Gal | No detectable terminal Galalpha 1-3 Gal |
| bisecGlcNAc | bisecGlcNAc | bisecGlcNAc |
| high Activity, in particular Fc activity | high Activity, in particular Fc activity | high Activity, in particular Fc activity |
| high yield | high yield | high yield |

TABLE 9-continued

| | | |
|---|---|---|
| 2-6 NeuNAc<br>2-3 NeuNAc<br>more sialic acid as defined in claim 2 and depending claims | low sialic acid as defined in claim 2 and depending claims | 2-6 NeuNAc |
| No NeuGc<br>No detectable terminal Galalpha 1-3 Gal<br>bisecGlcNAc<br>high Activity, in particular Fc activity<br>2-6 NeuNAc<br>2-3 NeuNAc<br>more sialic acid as defined in claim 2 and depending claims | No NeuGc<br>No detectable terminal Galalpha 1-3 Gal<br>bisecGlcNAc<br>high Activity, in particular Fc activity<br>low sialic acid as defined in claim 2 and depending claims | No NeuGc<br>No detectable terminal Galalpha 1-3 Gal<br>bisecGlcNAc<br>high Activity, in particular Fc activity<br>2-6 NeuNAc |
| No NeuGc<br>No detectable terminal Galalpha 1-3 Gal<br>bisecGlcNAc<br>high yield<br>2-6 NeuNAc<br>2-3 NeuNAc<br>more sialic acid as defined in claim 2 and depending claims | No NeuGc<br>No detectable terminal Galalpha 1-3 Gal<br>bisecGlcNAc<br>high yield<br>low sialic acid as defined in claim 2 and depending claims | No NeuGc<br>No detectable terminal Galalpha 1-3 Gal<br>bisecGlcNAc<br>high yield<br>2-6 NeuNAc |
| No NeuGc<br>No detectable terminal Galalpha 1-3 Gal | No NeuGc<br>No detectable terminal Galalpha 1-3 Gal | No NeuGc<br>No detectable terminal Galalpha 1-3 Gal |
| high Activity, in particular Fc activity<br>2-6 NeuNAc<br>2-3 NeuNAc<br>more sialic acid as defined in claim 2 and depending claims | high Activity, in particular Fc activity<br>low sialic acid as defined in claim 2 and depending claims | high Activity, in particular Fc activity<br>2-6 NeuNAc |
| No NeuGc<br>No detectable terminal Galalpha 1-3 Gal<br>high yield<br>2-6 NeuNAc<br>2-3 NeuNAc<br>more sialic acid as defined in claim 2 and depending claims | No NeuGc<br>No detectable terminal Galalpha 1-3 Gal<br>high yield<br>low sialic acid as defined in claim 2 and depending claims | No NeuGc<br>No detectable terminal Galalpha 1-3 Gal<br>high yield<br>2-6 NeuNAc |

TABLE 10

| Panko 1 | | |
|---|---|---|
| Fuc neg + BisGlcNAc neg. | H9D8 = 54% | H9D8-E6 = 79% |
| Fuc pos + BisGlcNAc pos | H9D8 = 5% | H9D8-E6 = 2% |
| Fuc neg + BisGlcNAc pos | H9D8 = 0% | H9D8-E6 = 0% |
| Panko 2 | | |
| Fuc neg + BisGlcNAc neg. | H9D8 = ~0% | F9 and GT-2X = ~5-6% |
| Fuc pos + BisGlcNAc pos | H9D8 = 36% | F9 and GT-2X = 29% |
| Fuc neg + BisGlcNAc pos | H9D8 = 0% | F9 and GT-2X = 0% |

The invention claimed is:

1. A method for producing a protein molecule composition, comprising
   (a) selecting an immortalized human blood host cell which has been identified as producing a protein molecule composition which (i) comprises no detectable NeuGc, (ii) comprises alpha2-6 linked NeuNAc, and (iii) has an increased sialylation degree with an amount of NeuNAc on the total carbohydrate structures or on the carbohydrate structures at one particular glycosylation site of the protein molecule of said protein molecules in said protein molecule composition which is at least 15% higher compared to the same amount of protein molecules in at least one protein molecule composition of the same protein molecule isolated from CHOdhfr− [ATCC No. CRL-9096] when expressed therein;
   (b) introducing in the host cell at least one nucleic acid encoding at least a part of said protein;
   (c) culturing said host cell under conditions which permit the production of said protein molecule composition; and
   (d) isolating said protein molecule composition.

2. The method according to claim 1, wherein said host cell is selected to produce a protein molecule composition having at least one of the following characteristics:
- (i) it comprises no detectable terminal Galalpha1-3Gal;
- (ii) it comprises at least 2% carbohydrate structures of the total carbohydrate units or of at least one particular carbohydrate chain at a particular glycosylation site of a protein molecule of the protein molecules in said protein molecule composition which contains bisecting GlcNAc;
- (iii) it comprises at least 5% carbohydrate structures of the total carbohydrate units or of at least one particular carbohydrate chain at a particular glycosylation site of a protein molecule of the protein molecules in said protein molecule composition which contains bisecting GlcNAc;
- (iv) it has an increased sialylation degree with an amount of NeuNAc on the total carbohydrate structures or on the carbohydrate structures at one particular glycosylation site of the protein molecule of said protein molecules in said protein molecule composition which is at least 20% higher compared to the same amount of protein molecules in at least one protein molecule composition of the same protein molecule isolated from CHOdhfr− [ATCC No. CRL-9096] when expressed therein;
- (v) it comprises at least 50% carbohydrate structures of the total carbohydrate units or of at least one particular carbohydrate chain at a particular glycosylation site of a protein molecule of the protein molecules in said protein molecule composition, lacking fucose; and
- (vi) it has a higher degree of sialylation than is reached in NM-F9 [DSM ACC2606] or NM-D4 [DSM ACC2605] cells; wherein the NM-F9 [DSM ACC2606] and NM-D4 [DSM ACC2605] cells only reach about 50 to 60% of the sialylation degree that is obtained with said host cell.

3. The method according to claim 1 for producing a protein molecule composition, wherein said host cell is selected to produce a protein composition having at least one of the following glycosylation characteristics:
- (i) it has a galactosylation degree on the total carbohydrate structures or on the carbohydrate structures at one particular glycosylation site of the protein molecule of the protein molecules in said protein molecule composition, that is increased compared to the same amount of protein molecules in at least one protein molecule composition of the same protein molecule isolated from CHOdhfr− [ATCC No. CRL-9096] when expressed therein;
- (ii) it has an amount of G2 structures on the total carbohydrate structures or on the carbohydrate structures at one particular glycosylation site of the protein molecule of said protein molecules in said protein molecule composition which is at least 5% higher compared to the same amount of protein molecules in at least one protein molecule composition of the same protein molecule isolated from CHOdhfr− [ATCC No. CRL-9096] when expressed therein;
- (iii) it has an amount of G0 structures on the total carbohydrate structures or on the carbohydrate structures at one particular glycosylation site of the protein molecule of said protein molecules in said protein molecule composition which is at least 5% lower compared to the same amount of protein molecules in at least one protein molecule composition of the same protein molecule isolated from CHOdhfr− [ATCC No. CRL-9096] when expressed therein;
- (iv) it comprises an amount of fucose on the total carbohydrate structures or on the carbohydrate structures at one particular glycosylation site of the protein molecule of said protein molecules in said protein molecule composition which is at least 5% less compared to the same amount of protein molecules in at least one protein molecule composition of the same protein molecule isolated from CHOdhfr− [ATCC No. CRL-9096] when expressed therein; and
- (v) it has a sialylation pattern which is altered compared to the sialylation pattern of at least one protein molecule composition of the same protein molecule isolated from CHOdhfr− [ATCC No. CRL-9096] when expressed therein, and wherein the protein molecules have at least one of the glycosylation characteristics (i) to (v).

4. The method according to claim 3, wherein said sialylation pattern is characterised by at least one of the following characteristics:
it has an increased sialylation degree with an amount of NeuNAc on the total carbohydrate structures or on the carbohydrate structures at one particular glycosylation site of the protein molecule of the protein molecules in said protein molecule composition which is at least 20% higher compared to the same amount of protein molecules in at least one protein molecule composition of the same protein molecule isolated from CHOdhfr− [ATCC No. CRL-9096] when expressed therein, and/or
it comprises at least 20% more charged N-glycosidically linked carbohydrate chains of the total carbohydrate units or of at least one particular carbohydrate chain at a particular glycosylation site of the protein molecule of the protein molecules in said protein molecule composition compared to the same amount of protein molecules in at least one protein molecule composition of the same protein molecule isolated from CHOdhfr− [ATCC No. CRL-9096] when expressed therein.

5. The method according to claim 1, wherein said host cell is selected to produce a glycoprotein, comprising
at least 10% carbohydrate structures of the total carbohydrate units or of at least one particular carbohydrate chain at a particular glycosylation site of the protein molecule of the protein molecules in said protein molecule composition, lacking fucose; and/or
at least 5% carbohydrate structures of the total carbohydrate units or of at least one particular carbohydrate chain at a particular glycosylation site of the protein molecule of the protein molecules in said protein molecule composition which contains bisecting GlcNAc; and/or
more than 35% G2 structures on the total carbohydrate structures or on the carbohydrate structures at one particular glycosylation site of the protein molecule in said protein molecule composition; and/or
less than 22% G0 structures on the total carbohydrate structures or on the carbohydrate structures at one particular glycosylation site of the protein molecule in said protein molecule composition.

6. The method according to claim 1, wherein said protein molecule composition produced has at least one of the following characteristics:
it has an increased activity and/or increased yield compared to at least one protein molecule composition of the same protein molecule when expressed in the cell line CHOdhfr− [ATCC No. CRL-9096];

it has an improved homogeneity compared to at least one protein molecule composition of the same protein molecule when expressed in the cell line CHOdhfr– [ATCC No. CRL-9096];

it has an increased average or maximum yield which is at least 10% higher than the yield of at least one protein molecule composition from the same protein molecule when expressed in the cell line CHOdhfr– [ATCC No. CRL-9096];

it has an improved homogeneity, which is an improved glycosylation homogeneity compared to at least one protein molecule composition of the same protein molecule when expressed in the cell line CHOdhfr– [ATCC No. CRL-9096];

it has an increased activity compared to at least one protein molecule composition of the same protein molecule when expressed in the cell line CHOdhfr– [ATCC No. CRL-9096];

in case said protein molecule is an antibody molecule, it has an increased Fc-mediated cellular cytotoxicity which is at least 2 times higher than the Fc-mediated cellular cytotoxicity of at least one antibody molecule composition from the same antibody molecule when expressed in the cell line CHOdhfr– [ATCC No. CRL-9096]; and/or in case said protein molecule is an antibody molecule, it has an increased antigen mediated or Fc-mediated binding which is at least 15% higher than the binding of at least one antibody molecule composition from the same antibody molecule when expressed in the cell line CHOdhfr– [ATCC No. CRL-9096].

7. The method according to claim 1, wherein a host cell is used, which is selected from the group consisting of:
(a) host cells having a higher sialylation degree than K562;
(b) host cells having a low or no fucosylation activity;
(c) host cells of human myeloid leukaemia origin;
(d) host cells derived from the cell line K562; and
(e) host cells selected from the group consisting of NM-H9D8 [DSM ACC2806], NM-H9D8-E6 [DSM ACC2807], and NM-H9D8-E6Q12 [DSM ACC2856].

8. The method according to claim 1, wherein a nucleic acid is introduced in the host cell, encoding an antifolate resistant DHFR-variant; and wherein the host cell is cultured with said antifolate.

9. The method according to claim 8, wherein at least one of the following characteristics is fulfilled
(a) the antifolate is methotrexate
(b) the nucleic acid encoding said antifolate resistant DHFR variant encodes a polypeptide having an amino acid sequence selected from the group consisting of SEQ ID No. 1 to 9.

10. The method according to claim 1, wherein the protein is selected from the group consisting of the group of cytokines, cytokine receptors, renin; human growth hormone, bovine growth hormone; growth hormone releasing factor; parathyroid hormone; thyroid stimulating hormone; lipoproteins; alpha-1-antitrypsin; insulin; gonadotrophins calcitonin; glucagon; clotting factors, von Willebrands factor; anti-clotting factors, atrial natriuretic factor; lung surfactant; plasminogen activators, bombesin; hemopoietic growth factor; enkephalinase; a serum albumin; mullerian-inhibiting substance; relaxin; prorelaxin; mouse gonadotropin-associated peptide; vascular endothelial growth factor; protein A and D; neurotrophic factors, platelet-derived growth factor; fibroblast growth factors; epidermal growth factor; insulin-like growth factor-I and -II; insulin-like growth factor binding proteins; osteoinductive factors; superoxide dismutase; T-cell receptors; surface membrane proteins; antibodies, immunoadhesins; and MUC1.

11. The method according to claim 1, wherein said protein is an antibody or a fragment thereof.

12. The method according to claim 11, wherein the antibody is selected from the group consisting of antibodies against ganglioside GD3, antibodies against human interleukin-5 receptor alpha-chain, antibodies against HER2, antibodies against CC chemokine receptor 4, antibodies against CD20, antibodies against CD22, antibodies against neuroblastoma, antibodies against MUC1, antibodies against epidermal growth factor receptor.

13. The method according to claim 11, wherein the antibody is selected from the group consisting of Pankomab, Muromomab, Daclizumab, Basiliximab, Abciximab, Rituximab, Trastuzumab, Gemtuzumab, Alemtuzumab, Ibritumomab, Cetuximab, Bevacizumab, Tositumomab, Pavlizumab, Infliximab, Eculizumab, Epratuzumab, Omalizumab, Efalizumab, Adalimumab, Alemtuzumab, Edrecolomab Basiliximab, Ruplizumab, OKT3, Declizumab, Abciximab, Palivizumab, Tuvirumab, Sevirumab, Oregovomab, Etaracizumab, anti-CC chemokine receptor 4 antibody KM2160, and anti-neuroblastoma antibody chCE7.

14. The method according to claim 11, wherein the antibody is selected from the group consisting of an antibody against MUC1; an antibody against HER2 and an antibody against EGFR.

15. The method according to claim 14, wherein the antibody is selected from the group consisting of PankoMab, Panko 1, Panko 2, Trastuzumab and CetuxiMab.

16. The method according to claim 10, wherein the cytokine is selected from the group consisting of TNF-alpha, TNF-beta, interferon, interferon-alpha, interferon-beta, interferon-gamma, M-CSF, GM-CSF, G-CSF, IL-1, IL-2, IL-3, IL-4, IL-5, IL-6, IL-7, IL-8, IL-9, IL-10, IL-11, IL-12, TGF-alpha, and TGF-beta.

17. The method according to claim 10, wherein the clotting factor is selected from the group consisting of factor VIIIC, factor IX, factor VII, tissue factor, and thrombin.

18. The method according to claim 10, wherein the anti-clotting factor is protein C.

19. The method according to claim 10, wherein the plasminogen activator is urokinase or human urine and tissue type plasminogen activator.

20. The method according to claim 10, wherein the serum albumin is human serum albumin.

21. The method according to claim 10, wherein the antibody is a rheumatoid factor.

22. The method according to claim 10, wherein the neurotrophic factor is selected from the group consisting of neutrophin-3, neutrophin-43, neutrophin-5, neutrophin-6, and nerve growth factor beta.

23. The method according to claim 10, wherein the gonadotrophin is selected from the group consisting of a follicle stimulating hormone, luteinizing hormone, and human chorionic gonadotrophin.

24. The method according to claim 10, wherein the osteoinductive factor is a bone morphogenic protein.

25. The method according to claim 10, wherein the surface membrane protein is selected from the group consisting of CD3, CD4, CD8, CD19, CD55, glycophorin A, and integrin.

26. The method according to claim 1, wherein said protein
(i) is fused to another peptide or polypeptide sequence selected from the group consisting of a linker, an activating molecule and a toxin; or (ii) is an antibody fragment fused to another protein sequence selected from the group consisting of cytokines, co-stimulatory factors, toxins, antibody fragments from other antibodies, multimerisation sequences, and sequences for detection, purification, secretion or stabilization; or (iii) is an antibody or antibody fragment coupled to an effector molecule which mediates a therapeutic effect selected from the group consisting of an immune effector molecule, a toxin and a radioisotope.

27. The method according to claim 1, wherein the protein is selected from the group consisting of erythropoietin, IL-1, IL-2, IL-3, IL-4, IL-5, IL-6, IL-7, IL-8, IL-9, IL-10, IL-11, IL-12, M-CSF, GM-CSF, and G-CSF.

28. The method according to claim 1, wherein the protein is selected from the group consisting of CD proteins; immunotoxins; colony stimulating factors, transforming growth factors interferons and interleukins.

29. The method according to claim 28, wherein the transforming growth factor is TGF-alpha or TGF-beta.

30. The method according to claim 28, wherein the interferon is selected from the group consisting of interferon-alpha, interferon-beta, and interferon-gamma.

31. The method according to claim 28, wherein the interleukin is selected from the group consisting of IL-1, IL-2, IL-3, IL-4, IL-5, IL-6, IL-7, IL-8, IL-9, IL-10, IL-11, and IL-12.

32. The method according to claim 28, wherein the CD protein is selected from the group consisting of CD3, CD4, CD8, CD19, and CD55.

33. A method for producing a protein molecule composition, comprising
(a) introducing in a host cell which is an immortalized human blood cell at least one nucleic acid encoding at least a part of said protein; and
(b) culturing said host cell under conditions which permit the production of said protein molecule composition; and
(c) isolating said protein molecule composition;
wherein the host cell is selected to produce a protein composition comprising protein molecules having the following characteristic glycosylation combinations:
(a)
it comprises no detectable NeuGc
it comprises no detectable Galalpha1-3Gal
it comprises a galactosylation pattern as defined in claim 3
it has a fucose content as defined in claim 3
it comprises bisecGlcNAc
it comprises an increased amount of sialic acid compared to a protein composition of the same protein molecule when expressed in the cell line CHOdhfr− [ATCC No. CRL-9096] or compared to the sialylation deficient cell line NM-F9 [DSM ACC2606] or NM-D4 [DSM ACC2605];
or
(b)
it comprises no detectable NeuGc
it comprises no detectable Galalpha1-3Gal
it comprises a galactosylation pattern as defined in claim 3
it has a fucose content as defined in claim 3
it comprises bisecGlcNAc
it comprises 2-6 NeuNAc.

34. An immortalized human blood cell, capable of producing a protein molecule composition having the following glycosylation characteristics:
(i) it comprises no detectable NeuGc;
(ii) it comprises alpha2-6 linked NeuNAc;
(iii) it has an increased sialylation degree with an amount of NeuNAc on the total carbohydrate structures or on the carbohydrate structures at one particular glycosylation site of the protein molecule of said protein molecules in said protein molecule composition which is at least 15% higher compared to the same amount of protein molecules in at least one protein molecule composition of the same protein molecule isolated from CHOdhfr− [ATCC No. CRL-9096] when expressed therein; and
(iv) it comprises at least 2% carbohydrate structures of the total carbohydrate units or of at least one particular carbohydrate chain at a particular glycosylation site of a protein molecule of the protein molecules in said protein molecule composition which contains bisecting GlcNAc.

35. The cell according to claim 34, wherein said protein molecule composition further has at least one of the following characteristics:
(i) it comprises no detectable terminal Galalpha1-3Gal;
(ii) it comprises at least 5% carbohydrate structures of the total carbohydrate units or of at least one particular carbohydrate chain at a particular glycosylation site of a protein molecule of the protein molecules in said protein molecule composition which contains bisecting GlcNAc;
(iii) it has an increased sialylation degree with an amount of NeuNAc on the total carbohydrate structures or on the carbohydrate structures at one particular glycosylation site of the protein molecule of said protein molecules in said protein molecule composition which is at least 20% higher compared to the same amount of protein molecules in at least one protein molecule composition of the same protein molecule isolated from CHOdhfr− [ATCC No. CRL-9096] when expressed therein;
(iv) it comprises at least 50% carbohydrate structures of the total carbohydrate units or of at least one particular carbohydrate chain at a particular glycosylation site of a protein molecule of the protein molecules in said protein molecule composition, lacking fucose; and/or
(v) it has a higher degree of sialylation than is reached in NM-F9 [DSM ACC2606] or NM-D4 [DSM ACC2605] cells; wherein the NM-F9 [DSM ACC2606] and NM-D4 [DSM ACC2605] cells only reach about 50 to 60% of the sialylation degree that is obtained with said host cell.

36. The isolated cell according to claim 34, selected from the group consisting of NM-H9D8 [DSM ACC 2806], NM-H9D8-E6 [DSM ACC 2807], and NM-H9D8-E6Q12 [DSM ACC 2856].

37. The cell according to claim 34, comprising at least one nucleic acid encoding a protein molecule or at least one part thereof, and at least one nucleic acid comprising at least one nucleic acid sequence encoding at least one polypeptide having an amino acid sequence selected from the group consisting of SEQ ID No: 1 to 9.

* * * * *